US008541471B2

(12) United States Patent
Hansen et al.

(10) Patent No.: US 8,541,471 B2
(45) Date of Patent: Sep. 24, 2013

(54) WATER-SOLUBLE STRONTIUM SALTS FOR USE IN TREATMENT OF CARTILAGE AND/OR BONE CONDITIONS

(75) Inventors: Christian Hansen, Vedbaek (DK); Henrik Nilsson, København K (DK); Stephan Christgau, Gentofte (DK); Jens E. T. Andersen, Vedbaek (DK)

(73) Assignee: Osteologix A/S, Copenhagen (DK)

( * ) Notice: Subject to any disclaimer, the term of this patent is extended or adjusted under 35 U.S.C. 154(b) by 771 days.

(21) Appl. No.: 12/535,053

(22) Filed: Aug. 4, 2009

(65) Prior Publication Data

US 2010/0048697 A1 Feb. 25, 2010

Related U.S. Application Data

(63) Continuation of application No. 11/269,289, filed on Nov. 7, 2005, now Pat. No. 7,595,342, which is a continuation-in-part of application No. PCT/DK2004/000328, filed on May 6, 2004, application No. 12/535,053, which is a continuation-in-part of application No. PCT/DK2005/000140, filed on Feb. 28, 2005, and a continuation-in-part of application No. PCT/DK2005/000404, filed on Jun. 17, 2005, and a continuation-in-part of application No. PCT/DK2005/000401, filed on Jun. 17, 2005.

(60) Provisional application No. 60/528,442, filed on Dec. 9, 2003.

(30) Foreign Application Priority Data

| May 7, 2003 | (DK) | 2003 00691 |
| Jun. 20, 2003 | (DK) | 2003 00932 |
| Dec. 9, 2003 | (DK) | 2003 01820 |

(51) Int. Cl.
*A61K 31/19* (2006.01)

(52) U.S. Cl.
USPC ........................................................ 514/574

(58) Field of Classification Search
None
See application file for complete search history.

(56) References Cited

U.S. PATENT DOCUMENTS

| 3,478,073 A | 11/1969 | Rydh |
| 4,056,567 A | 11/1977 | Lamberti et al. |
| 4,230,700 A | 10/1980 | Francis |
| 4,921,971 A | 5/1990 | Krimmer et al. |
| 4,939,164 A | 7/1990 | Wierzbicki et al. |
| 5,075,336 A | 12/1991 | Czernecki et al. |
| 5,128,367 A | 7/1992 | Wierzbicki et al. |
| 5,380,738 A | 1/1995 | Normal et al. |
| 5,399,357 A | 3/1995 | Akiyama et al. |
| 5,475,021 A | 12/1995 | Marnett et al. |
| 5,585,504 A | 12/1996 | Desmond et al. |
| 5,620,999 A | 4/1997 | Weier et al. |
| 5,633,272 A | 5/1997 | Talley et al. |
| 5,643,933 A | 7/1997 | Talley et al. |
| 5,668,161 A | 9/1997 | Talley et al. |
| 5,681,842 A | 10/1997 | Dellaria et al. |
| 5,686,460 A | 11/1997 | Nicolai et al. |
| 5,686,470 A | 11/1997 | Weier et al. |
| 5,696,431 A | 12/1997 | Giannopoulos et al. |
| 5,707,980 A | 1/1998 | Knutson |
| 5,719,163 A | 2/1998 | Norman et al. |
| 5,750,558 A | 5/1998 | Brooks et al. |
| 5,753,688 A | 5/1998 | Talley et al. |
| 5,756,530 A | 5/1998 | Lee et al. |
| 5,756,531 A | 5/1998 | Brooks et al. |
| 5,760,068 A | 6/1998 | Talley et al. |
| 5,776,967 A | 7/1998 | Kreft et al. |
| 5,776,984 A | 7/1998 | Dellaria et al. |
| 5,783,597 A | 7/1998 | Beers et al. |
| 5,807,873 A | 9/1998 | Nicolai et al. |
| 5,824,699 A | 10/1998 | Kreft et al. |
| 5,830,911 A | 11/1998 | Failli et al. |
| 5,840,924 A | 11/1998 | Desmond et al. |
| 5,851,556 A | 12/1998 | Breton et al. |
| 5,856,356 A | 1/1999 | Tsouderos et al. |
| 5,859,257 A | 1/1999 | Talley et al. |
| 5,866,168 A | 2/1999 | De Lacharriere et al. |
| 5,883,267 A | 3/1999 | Rossen et al. |
| 5,905,089 A | 5/1999 | Hwang et al. |
| 5,908,852 A | 6/1999 | Talley et al. |

(Continued)

FOREIGN PATENT DOCUMENTS

| DE | 102 25 420 | 12/2003 |
| EP | 0 390 456 | 3/1990 |

(Continued)

OTHER PUBLICATIONS

Berge et al. Journal of Pharmaceutical Sciences, 1977, 66(1), 1-19.*
Gastineau et al., "Metabolic Studies of a Patient with Osteoporosis and Diabetes Mellitus," *Proceedings of the Staff Meeting of The Mayo Clinic*, vol. 34(7), pp. 165-172 (1959).
U.S. Appl. No. 10/556,149, filed Nov. 4, 2008, Office Action mailed.

(Continued)

*Primary Examiner* — Yevegeny Valenrod

(74) *Attorney, Agent, or Firm* — Foley & Lardner LLP

(57) ABSTRACT

Compounds and pharmaceutical compositions for use in the treatment and/or prophylaxis of cartilage and/or bone conditions and for methods of treating such condition. The compounds are salts of strontium that have a water-solubility of from about 1 g/l to about 100 g/l at room temperature, especially amino acid salts of strontium or dicarboxylic acid salts of strontium. Examples of novel water-soluble strontium salts are e.g. strontium glutamate and strontium alpha-ketoglutarate. The present invention also relates to an improved method for preparing the strontium salt of glutamic acid.

58 Claims, 21 Drawing Sheets

(56) References Cited

U.S. PATENT DOCUMENTS

| | | |
|---|---|---|
| 5,908,858 A | 6/1999 | Kimura et al. |
| 5,925,631 A | 7/1999 | Black et al. |
| 5,935,990 A | 8/1999 | Khanna et al. |
| 5,945,538 A | 8/1999 | Kameswaran |
| 5,945,539 A | 8/1999 | Haruta et al. |
| 5,972,986 A | 10/1999 | Seibert et al. |
| 5,980,905 A | 11/1999 | de la Harpe et al. |
| 5,985,902 A | 11/1999 | Talley et al. |
| 5,990,148 A | 11/1999 | Isakson et al. |
| 5,994,381 A | 11/1999 | Haruta et al. |
| 6,001,843 A | 12/1999 | Dube et al. |
| 6,002,014 A | 12/1999 | Haruta et al. |
| 6,025,353 A | 2/2000 | Masferrer et al. |
| 6,028,072 A | 2/2000 | Lee et al. |
| 6,046,191 A | 4/2000 | Hamley et al. |
| 6,077,869 A | 6/2000 | Sui et al. |
| 6,080,876 A | 6/2000 | Dorziotis et al. |
| 6,083,969 A | 7/2000 | Ferro et al. |
| 6,136,839 A | 10/2000 | Isakson et al. |
| 6,207,335 B1 | 3/2001 | Michel et al. |
| 6,232,497 B1 | 5/2001 | Pischel |
| 6,245,797 B1 | 6/2001 | Winokur |
| 6,365,152 B1 | 4/2002 | McKinney |
| 7,091,364 B2 | 8/2006 | Vaysse-Ludot et al. |
| 7,105,683 B2 | 9/2006 | Vaysse-Ludot et al. |
| 7,214,805 B2 | 5/2007 | Vaysse-Ludot et al. |
| 7,241,460 B2 | 7/2007 | Jellum et al. |
| 7,273,523 B2 | 9/2007 | Wenz |
| 7,589,235 B2 | 9/2009 | Christgau et al. |
| 7,595,342 B2 | 9/2009 | Hansen et al. |
| 2002/0018748 A1 | 2/2002 | Satz et al. |
| 2002/0051822 A1 | 5/2002 | Atherton et al. |
| 2006/0122274 A1 | 6/2006 | Hansen et al. |
| 2006/0216358 A1 | 9/2006 | Hansen et al. |
| 2006/0275503 A1 | 12/2006 | Hansen et al. |
| 2008/0167513 A1 | 7/2008 | Hansen et al. |
| 2008/0221213 A1 | 9/2008 | Christgau et al. |
| 2008/0317849 A1 | 12/2008 | Christgau et al. |
| 2009/0035315 A1 | 2/2009 | Christgau et al. |
| 2009/0137678 A1 | 5/2009 | Christgau et al. |

FOREIGN PATENT DOCUMENTS

| | | |
|---|---|---|
| EP | 0 381 445 | 8/1990 |
| EP | 0 404 558 | 12/1990 |
| EP | 0 415 850 | 3/1991 |
| EP | 0 737 471 A1 | 10/1996 |
| EP | 0 745 596 A1 | 12/1996 |
| EP | 0 813 869 | 12/1997 |
| EP | 0 937 722 A1 | 8/1999 |
| EP | 1 006 114 A1 | 6/2000 |
| EP | 1 534 305 | 10/2006 |
| FR | 2665896 | 2/1992 |
| GB | 241266 | 10/1925 |
| GB | 729376 | 5/1955 |
| GB | 990 957 | 5/1965 |
| JP | 48000441 A | 1/1973 |
| WO | WO 96/36617 A1 | 11/1991 |
| WO | WO 94/15932 A1 | 7/1994 |
| WO | WO 94/27980 A1 | 12/1994 |
| WO | WO 95/11883 A1 | 5/1995 |
| WO | WO 95/15315 A1 | 6/1995 |
| WO | WO 95/15316 A1 | 6/1995 |
| WO | WO 95/15317 A1 | 6/1995 |
| WO | WO 95/15318 A1 | 6/1995 |
| WO | WO 95/21817 A1 | 8/1995 |
| WO | WO 95/30652 A1 | 11/1995 |
| WO | WO 95/30656 A1 | 11/1995 |
| WO | WO 96/03385 A1 | 2/1996 |
| WO | WO 96/03387 A1 | 2/1996 |
| WO | WO 96/03388 A1 | 2/1996 |
| WO | WO 96/03392 A1 | 2/1996 |
| WO | WO 96/09293 A1 | 3/1996 |
| WO | WO 96/09304 A1 | 3/1996 |
| WO | WO 96/16934 A1 | 6/1996 |
| WO | WO 96/19462 A1 | 6/1996 |
| WO | WO 96/19463 A1 | 6/1996 |
| WO | WO 96/24584 A1 | 8/1996 |
| WO | WO 96/24585 A1 | 8/1996 |
| WO | WO 96/25405 A1 | 8/1996 |
| WO | WO 96/31509 A1 | 10/1996 |
| WO | WO 96/38418 A1 | 12/1996 |
| WO | WO 96/38442 A1 | 12/1996 |
| WO | WO 96/41626 A1 | 12/1996 |
| WO | WO 96/41645 A1 | 12/1996 |
| WO | WO 97/03953 A1 | 2/1997 |
| WO | WO 97/11704 A1 | 3/1997 |
| WO | WO 97/25045 A1 | 7/1997 |
| WO | WO 97/27181 A1 | 7/1997 |
| WO | WO 97/29776 A1 | 8/1997 |
| WO | WO 97/34882 A1 | 9/1997 |
| WO | WO 97/37984 A1 | 10/1997 |
| WO | WO 97/38986 A1 | 10/1997 |
| WO | WO 97/41100 A1 | 11/1997 |
| WO | WO 97/44027 A1 | 11/1997 |
| WO | WO 97/44028 A1 | 11/1997 |
| WO | WO 97/45420 A1 | 12/1997 |
| WO | WO 98/03484 A1 | 1/1998 |
| WO | WO 98/04527 A1 | 2/1998 |
| WO | WO 98/05639 A1 | 2/1998 |
| WO | WO 98/06708 A1 | 2/1998 |
| WO | WO 98/07714 A1 | 2/1998 |
| WO | WO 98/11080 A1 | 3/1998 |
| WO | WO 98/21195 A1 | 5/1998 |
| WO | WO 98/22442 A2 | 5/1998 |
| WO | WO 98/32732 A1 | 7/1998 |
| WO | WO 98/33769 A1 | 8/1998 |
| WO | WO 98/35657 | 8/1998 |
| WO | WO 98/39330 A1 | 9/1998 |
| WO | WO 98/41511 A1 | 9/1998 |
| WO | WO 98/41516 A1 | 9/1998 |
| WO | WO 98/43649 A2 | 10/1998 |
| WO | WO 98/43966 A1 | 10/1998 |
| WO | WO 98/46594 A1 | 10/1998 |
| WO | WO 98/47509 A1 | 10/1998 |
| WO | WO 98/47890 A1 | 10/1998 |
| WO | WO 98/50033 A1 | 11/1998 |
| WO | WO 98/50075 A1 | 11/1998 |
| WO | WO 98/52937 A2 | 11/1998 |
| WO | WO 99/01115 A1 | 1/1999 |
| WO | WO 99/05104 A1 | 2/1999 |
| WO | WO 99/10331 A1 | 3/1999 |
| WO | WO 99/10332 A1 | 3/1999 |
| WO | WO 99/11605 A1 | 3/1999 |
| WO | WO 99/12930 A1 | 3/1999 |
| WO | WO 99/14194 A1 | 3/1999 |
| WO | WO 99/14195 A1 | 3/1999 |
| WO | WO 99/15205 A1 | 4/1999 |
| WO | WO 99/18960 A1 | 4/1999 |
| WO | WO 99/20589 A1 | 4/1999 |
| WO | WO 99/21585 A1 | 5/1999 |
| WO | WO 99/22720 A2 | 5/1999 |
| WO | WO 99/23087 A1 | 5/1999 |
| WO | 99/33796 A1 | 7/1999 |
| WO | WO 99/34772 | 7/1999 |
| WO | WO 99/35130 A1 | 7/1999 |
| WO | WO 99/41224 A1 | 8/1999 |
| WO | WO 99/59634 A1 | 11/1999 |
| WO | WO 99/59635 A1 | 11/1999 |
| WO | WO 99/61016 A1 | 12/1999 |
| WO | WO 99/62884 A1 | 12/1999 |
| WO | WO 99/64415 A1 | 12/1999 |
| WO | WO 00/00200 A1 | 1/2000 |
| WO | WO 00/01380 A1 | 1/2000 |
| WO | WO 00/01692 | 1/2000 |
| WO | WO 00/08024 A1 | 2/2000 |
| WO | WO 00/10993 A1 | 3/2000 |
| WO | WO 00/23433 A1 | 4/2000 |
| WO | WO 00/24719 A1 | 5/2000 |
| WO | WO 00/26216 A1 | 5/2000 |
| WO | WO 00/29022 A1 | 5/2000 |
| WO | WO 00/29023 A1 | 5/2000 |
| WO | WO 00/37107 A2 | 6/2000 |
| WO | WO 00/38730 A2 | 7/2000 |
| WO | WO 00/38786 A2 | 7/2000 |

| WO | WO 00/40087 A1 | 7/2000 |
| --- | --- | --- |
| WO | WO 00/48583 A2 | 8/2000 |
| WO | WO 00/51685 A1 | 9/2000 |
| WO | WO 00/52008 A1 | 9/2000 |
| WO | WO 00/53149 A2 | 9/2000 |
| WO | WO 00/68215 A1 | 11/2000 |
| WO | WO 02/62351 A1 | 8/2002 |
| WO | WO 03/03664 A1 | 1/2003 |
| WO | WO 03/028742 | 4/2003 |
| WO | WO 03/043626 | 5/2003 |
| WO | WO 03/75741 A2 | 9/2003 |
| WO | WO 2004/17952 A1 | 3/2004 |
| WO | WO 2004/043455 A1 | 5/2004 |
| WO | WO 2004/084920 | 10/2004 |
| WO | WO 2004/098617 | 11/2004 |
| WO | WO 2004/098618 | 11/2004 |
| WO | WO 2004/098619 | 11/2004 |
| WO | WO 2005/049038 | 6/2005 |
| WO | WO 2005/082385 | 9/2005 |
| WO | WO 2005/108339 | 11/2005 |
| WO | WO 2005/123098 | 12/2005 |
| WO | WO 2005/123192 | 12/2005 |
| WO | WO 2005/123193 | 12/2005 |
| WO | WO 2006/089546 | 8/2006 |
| WO | WO 2007/003200 | 1/2007 |

OTHER PUBLICATIONS

U.S. Appl. No. 10/556,150, filed Jun. 24, 2008, Office Action mailed.
Aug. 3, 2007, Communication of a Notice of Opposition in European Patent No. 1 534 305.
Mar. 5, 2008, Response of Patent Proprietor to Notice of Opposition in European Patent No. 1 534 305.
Jul. 18, 2008, Summons to Attend Oral Proceedings Pursuant to Rule 115(1) EPC in EP 1 534 305.
Dec. 19, 2008, Response of Patent Proprietor to Summons to Oral Proceedings in Opposition to European Patent No. 1 534 305.
Mar. 19, 2009, Decision Rejecting Opposition to European Patent No. 1 534 305.
[No author named] "Calcium, phosphorus, and strontium metabolism in infants," Nutr Rev Sep. 1969;27(9):254-6.
[No author named] "Influence of stable strontium on bone growth and strength," Nutr Rev Oct. 1959;17:312-3.
Albertsson et al., "An x-ray and neutron study of a gel-brown phase of calcium malonate dihydrate," Acta Cryst 1978;B34:2737-43.
Alda et al., "Transport of calcium, magnesium and strontium by human serum proteins," Rev Esp Fisiol Jun. 1985;41(2):145-9.
Ammann et al., "Strontium ranelate improves bone resistance by increasing bone mass and improving architecture in intact female rats," J Bone Miner Res Dec. 2004;19(12):2012-20.
Anderson et al., "Solubility of various forms of strontium titanate in lungs: in vitro and in vivo studies," Health Phys Jun. 1999;76(6):628-34.
Anderson et al., "Strontium retention as a function of age in the dog," Rad Res 1968;34:153-69.
Apostoaei, "Absorption of strontium from the gastrointestinal tract into plasma in healthy human adults," Health Phys Jul. 2002;83(1):56-65.
Appleton, "Changes in the plasma electrolytes and metabolites of the rat following acute exposure to sodium fluoride and strontium chloride," Arch Oral Biol Apr. 1995;40(4):265-8.
Ardissino et al., "No difference in intestinal strontium absorption after oral or IV calcitriol in children with secondary hyperparathyroidism. The European Study Group on Vitamin D in Children with Renal Failure," Kidney Int Sep. 2000;58(3):981-8.
Armbrecht et al., "Effect of 1,25-dihydroxyvitamin D3 on intestinal calcium absorption in strontium-fed rats," Arch Biochem Biophys Feb. 1979;192(2):466-73.
Ashrafi et al., "Pre- and posteruptive effects of low doses of strotium on dental caries in the rat," Caries Res 1980;14(5):341-6.
Bader et al., "The effect of hydroxylamine, mercaptans, divalent metals and chelators on (Na+ plus K+)-ATPase. A possible control mechanism," Biochim Biophys Acta Mar. 18, 1970;198(3):583-93.
Barbara et al., "Normal matrix mineralization induced by strontium ranelate in MC3T3-E1 osteogenic cells," Metabolism Apr. 2004;53(4):532-7.

Barlow, "Strontium and Osteoporosis," J. of the British Menopause Society, Mar. 2003; 9(1) 7.
Barry et al., "The hemodynamic effects of strontium chloride in the intact dog," Proc Soc Exp Biol Med Oct. 1972;141(1):52-8.
Barto et al., "Sensitive method for analysis of strontium in human and animal plasma by graphite furnace atomic absorption spectrophotometry," Clin Chem Aug. 1995;41(8 Pt 1):1159-63.
Berger et al., "[On mechanism of strontium deposition in bone tissue]," Acta Histochem Dec. 24, 1965;22(5):298-308, (in German, w/ English Abstract).
Best et al., "Strontium ions induce production of thromboxane B2 and secretion of 5-hydroxytryptamine in washed human platelets," Biochem Pharmacol Mar. 15, 1981;30(6):635-7.
Bianchi et al., "No difference in intestinal strontium absorption after an oral or an intravenous 1,25(OH)2D3 bolus in normal subjects. For the European Study Group on Vitamin D in children with renal failure," J Bone Miner Res Oct. 1999;14(10):1789-95.
Blake et al., "A reivw of strontium ranelate and its effect on DXA scans," J. of Clin. Densitometry, 10(2), pp. 113-119 (2007).
Blumsohn, "Stable strontium absorption as a measure of intestinal calcium absorption: comparison with the double-radiotracer calcium absorption test," Clin Sc 1994;87:363-8.
Boivin et al., "Effects of bisphosphonates on matrix mineralization," J Musculoskelet Neuronal Interact Dec. 2002;2(6):538-43.
Boivin et al., "Strontium distribution and interactions with bone mineral in monkey iliac bone after strontium salt (S 12911) administration," J Bone Miner Res Sep. 1996;11(9):1302-11.
Brandi, "New perspectives in the prevention and treatment of glucocorticoid-induced osteoporis," Clin and Experimental Rheum 2000;18(5):S74-8.
Briggman et al., "The crystal structures of calcium malonate dihydrate and strontium malonate," Acta Cryst (1977);B333:1900-06.
Brown et al., "Is the calcium receptor a molecular target for the actions of strontium on bone?," Osteoporosis Int 2003;14(3):S25-34.
Buehler et al., "Strontium ranelate inhibits bone resorption while maintaining bone formation in alveolar bone in monkeys (*Macaca fascicularis*)," Bone Aug. 2001;29(2):176-9.
Burguera et al., "Age amd sex-related calcium and strontium concentrations in different types of human bones," Trace Elements and Electrolytes 2002;19(3):143-51.
Burton et al., "Discrimination between strontium and calcium in their passage from diet to the bone of adult man," Nature Mar. 3, 1962;193:846-7.
Cabrera et al., "Strontium and bone," J Bone Miner Res May 1999;14(5):661-8.
Canalis et al., "The divalent strontium salt S12911 enhances bone cell replication and bone formation in vitro," Bone Jun. 1996;18(6):517-23.
Carafoli, "In vivo effect of uncoupling agents on the incorporation of calcium and strontium into mitochondria and other subcellular fractions of rat liver," J Gen Physiol Aug. 1967;50(7):1849-64.
Christopffersen et al., "Effects of strontium ions on growth and dissolution of hydroxyapatite and on bone mineral detection," Bone Jan. 1997;20(1):47-54.
Cohn et al., "Kinetics of strontium and calcium skeletal metabolism in the rat," Riv Patol Nerv Ment Aug. 1966;87(4):79-83.
Cole et al., "The toxicity of strontium and calcium," J Pharmcol Exp Ther 1941;404(71):1-5.
Creger et al., "Strontium and bone development under conditions of suboptimal vitamin D," Calc Tissue Res 1971;8(1):83-6.
D'Haese et al., "Increased bone strontium levels in hemodialysis patients with osteomalacia," Kidney Int Mar. 2000;57(3):1107-14.
D'Haese et al., "Measurement of strontium in serum, urine, bone, and soft tissues by Zeeman atomic absorption spectrometry," Clin Chem Jan. 1997;43(1):121-8.
Dahl et al., "Incorporation and distribution of strontium in bone," Bone Apr. 2001;28(4):446-53.
Delannoy et al., "Long-term treatment with strontium ranelate increases vertebral bone mass without deleterious effect in mice," Metabolism Jul. 2002;51(7):906-11.
Doggrell, "Present and future pharmacotherapy for osteoporosis," Drugs Today (Barc) Aug. 2003;39(8):633-57.

Eisenberg, "Effect of intravenous phosphate on serum strontium and calcium," N. Engl J Med Apr. 16, 1970;282(16):889-92.

Eisenberg, "Effects of androgens, estrogens and corticoids on strontium kinetics in man," J Clin Endocrinol Metab May 1966;26(5):566-72.

Ferraro et al., "The effect of strontium chloride upon alveolar bone," J Periodontol Jun. 1980;51(6):345-7.

Foreman et al., "Proceedings: Activation of anaphylactic histamine release by calcium and strontium ions," Br J Pharmacol Feb. 1972;44(2):326P.

Fujita et al., "Retention and excretion of strontium-85 in mice, rats and rabbits—extrapolation to long-term retention in humans, " Health Phys Apr. 1965;11:271-81.

Gastineau et al., "Metabolic studies of a patient with osteoporosis and diabetes mellitus: effects of testosterone enanthate and strontium laciate," Mayo Med Ventures Mar. 1960;35(2):105-11.

Ghosh et al., "Clastogenic activity of strontium chloride on bone marrow cells in vivo," Biol Trace Elem Res Apr. 1990;25(1):51-6.

Gibbons et al., "The passage of calcium and strontium across the gut of the anaesthetized goat," J Physiol Apr. 1972;222(2):397-406.

Gruden, "The effect of lactose and iron on strontium absorption," Experientia Sep. 15, 1984;40(9):941-2.

Grynpas et al., "Effects of low doses of strontium on bone quality and quantity in rats," Bone 1990;11(5):313-9.

Grynpas et al., "Strontium increases vertebral bone volume in rats at a low dose that does not induce detectable mineralization defect," Bone Mar. 1996;18(3):253-9.

Gusmano et al., "Evaluation of the parameters of strontium metabolism in the rat as a function of age," Radiat Res Mar. 1968;33(3):540-53.

Gutteridge et al., "Delayed strontium absorption in post-menopausal osteoporosis and osteomalacia," Clin Sci Apr. 1968;34(2):351-63.

Hahn, "Strontium is a potent and selective inhibitor of sensory irritation," Dermatol Surg Sep. 1999;25(9):689-94.

Harrison et al., "The metabolism of strontium in man," Clin Sci (Lond) Nov. 1955;14(4):681-95.

Harrison et al., "Bone metabolism in rats, studied with stable strontium," J Endocrinol Nov. 1960;21:191-6.

Harrison et al., "On the mechanism of skeletal fixation of strontium. Parts I and II," Archives BioChem 1959;80:97-113.

Hendrix et al., "Competition between calcium, strontium, and magnesium for absorption in the isolated rat intestine," Clin Chem Dec. 1963;12:734-44.

Hibbins, "Strontium and strontium compounds," Kirk-Othmer Encyclopedia of Chemical Technology, 4$^{th}$ ed. 1997;22:947-55.

Houston et al., "The systemic treatment of bone metastases," Clin Orthop Relat Res Mar. 1995;(312):95-104.

International Search Report of International Application No. PCT/DK2004/00327, mailed Feb. 14, 2005.

International Search Report of International Application No. PCT/DK2004/000326, mailed Feb. 23, 2005.

International Search Report of International Application No. PCT/DK2004/000328, mailed Feb. 4, 2005.

International Search Report of International Application No. PCT/DK2005/000710, mailed Feb. 7, 2006.

Johnson et al., "The exchangeability of calcium and strontium of bone in vitro," Calcif Tissue Res. 1970;6(2):103-12.

Johnson et al., "The incorporation and removal of large amounts of strontium by physiologic mechanisms in mineralized tissues," Calcif Tissue Res 1968;2(3):242-52.

Kroes et al., "Short-term toxicity of strontium chloride in rats," Toxicology Feb. 1977;7(1):11-21.

Leeuwenkamp et al., "Human pharmacokinetics of orally administered strontium.," Calcif Tissue Int Sep. 1990;47(3):136-41.

Lehnerdt, [On the question of replacing calcium in the bone system by strontium Second Report. Feeding of strontium to suckling animals, the influence of strontium on the bonei system of the weaned young] 215-47 (in German, w/ English translation).

Lloyd, "Relative binding of strontium and calcium in protein and non-protein fractions of serum in the rabbit," Nature. Jan. 27, 1968;217(126):355-6.

Loeser et al., "A study of the toxicity of strontium and comparison with other cations employed in therapeutics," J Lab Clin Med 1930;15:35-41.

MacDonald et al., "The skeletal deposition of non-radioactive strontium," J Biol Chem Jan. 1951;188(1):137-43.

Maltby et al., "Exchange of potassium and strontium in adult bone," Am J Physiol Apr. 1982;242(4):H705-12.

Marie et al., "An uncoupling agent containing strontium prevents bone loss by depressing bone resorption and maintaining bone formation in estrogen-deficient rats," J Bone Miner Res May 1993;8(5):607-15.

Marie et al., "Effect of low doses of stable strontium on bone metabolism in rats," Miner Electrolyte Metab 1985;11(1):5-13.

Marie et al., "Histomorphometry of bone changes in stable strontium therapy," Envron. Health 1985;19:193-208.

Marie et al., "Mechanisms of action and therapeutic potential of strontium in bone," Calcif Tissue Int Sep. 2001;69(3):121-9.

Marie et al., Short-term effects of fluoride and strontium on bone formation and resorption in the mouse, Metabolism. Jun. 1986;35(6):547-51.

Marie, P.J., "Effects of Strontium on Bone Tissue and Bone Cells," Therapeutic Uses of Trace Elements, Ed. Neve, et al., Plenum Press, New York, pp. 277-282 (1996).

Matsumoto, "Effect of strontium chloride on bone resorption induced by prostaglandin E2 in cultured bone," Arch Toxicol 1988;62(2-3):240-1.

McCaslin et al., "The effect of strontium lactate in the treatment of osteoporosis," Staff Meeting at the Mayo Clinic 1959;34(13):329-34.

Meunier et al., "Design and methodology of the phase 3 trials for the clinical development of strontium ranelate in the treatment of women with postmenopausal osteoporosis," Osteoporos Int. 2003;14 Suppl 3:S66-76.

Meunier et al., "Strontium ranelate: dose-dependent effects in established postmenopausal vertebral osteoporosis—a 2-year randomized placebo controlled trial," J Clin Endocrinol Metab. May 2002;87(5):2060-6.

Meunier et al., "The effects of strontium ranelate on the risk of vertebral fracture in women with postmenopausal osteoporosis," N Engl J Med Jan. 29, 2004;350(5):459-68.

Morohashi et al., "Effects of strontium on calcium metabolism in rats. II. Strontium prevents the increased rate of bone turnover in ovariectomized rats" Jpn J Pharmacol Jun. 1995;68(2):153-9.

Müller et al., "The course in time of the strontium retention in man," Health Phys 14(4):285-292 (1968).

Newton et al., "Metabolism of Ca and Sr in late adult life," Health Phys. 59(4):433-42 (1990).

Nielsen et al., "Influence of strontium on bone mineral density and bone mineral content measurements by dual X-ray absorptiometry," J Clin Densitom 1999 Winter;2(4):371-9.

Palmer et al., "Discrimination in intestinal absorption of strontium and calcium," Proc Soc Exp Biol Med Nov. 1961;108:296-300.

Palmer et al., "Strontium-calcium interrelationships in the growing rat," Am J Physiol Sep. 1964;207:561-6.

Price et al., "Hydrothermal crystallisation and x-ray structure of anhydrous strontium oxalate," Polyhedron 1999;18:2499-2503.

PROELOS® Leaflet 2008 from www.servier.com.

Reginster et al., "Strontium ranelate: a new paradigm in the treatment of osteoporosis," Drugs Today (Barc). Feb. 2003;39(2):89-101.

Reginster et al., "Prevention of early postmenopausal bone loss by strontium ranelate: the randomized, two-year, double-masked, dose-ranging, placebo-controlled PREVOS trial," Osteoporos Int Dec. 2002;13(12):925-31.

Reginster et al., "Strontium ranelate phase 2 dose-ranging studies: PREVOS and STRATOS studies," Osteoporos Int 2003;14 Suppl 3:S56-65.

Reginster et al., "*Strontium ranelate: a new paradigm in the treatment of osteoporosis*," Expert Opin. Investig. Drugs, 13(7) 857-864 (2004).

Reginster,"*Strontium ranelate* in osteoporosis," Curr Pharm Des 2002;8(21):1907-16.

Reid et al., "The assessment of intestinal calcium absorption using stable strontium," Calcif Tissue Int. May 1986;38(5):303-5.

Schmidbaur et al., "Metal ion binding by amino acids: strontium and barium L-asspartate trijudrate SR/BA(L-ASP) 3h20," Chemische Berichte, Verlas Chemie GMBH 1990;123(8):1599-602.

Schmidbaur et al., "Preparation and crystal structures of magnesium, strontium, and barium 1-glutamate hydrates," Chem Ber 1989;122:1433-8.

Schoenberg, "Extent of strontium substitution for calcium in hydroxyapatite," Biochim Biophys Acta. Jul. 23, 1963;75:96-103.

Schroeder et al., "Trace metals in man: strontium and barium," J Chronic Dis Sep. 1972;25(9):491-517.

Schrooten et al., "Strontium causes osteomalacia in chronic renal failure rats," Kidney Int Aug. 1998;54(2):448-56.

Shorr et al., "The usefulness of strontium as an adjuvant to calcium in the remineralization of the skeleton in man," Bull Hosp Joint Dis Apr. 1952;13(l):59-66.

Skoryna, "Effects of oral supplementation with stable strontium," Can Med Assoc J Oct. 1, 1981;125(7):703-12.

Sorbera et al., "*Strontium ranelate* treatment and prevention of osteoporosis bone resorption inhibitor bone formation stimulant," Drug Fut Apr. 2003;28(4):328-35.

Storey, "Calcium and strontium changes in bone associated with continuous administration of stable strontium to rats," Arch Biochem Biophys Mar. 20, 1968;124(1):575-81.

Storey, "Strontium 'rickets': bone, calcium and strontium changes," Australas Ann Med Aug. 1961;10:213-22.

Svensson et al., "The effect of strontium and manganese on freshly isolated chondrocytes," Acta Pathol Microbiol Immunol Scand [A] May 1985;93(3):115-20.

Ten Bolscher et al., "Oestrogen has no short-term effect on intestinal strontium absorption in healthy postmenopausal women," Clin Endocrinol (Oxf) Mar. 1999;50(3):387-92.

Ten Bolscher et al., "Strontium as a marker for intestinal calcium absorption: the stimulatory effect of calcitriol," Clin Chem 2000;46(2):248-51.

Uriu et al., "Uncoupling between bone formation and resorption in ovariectomized rats with chronic cadmium exposure," Toxicol Appl Pharmacol May 1, 2000;164(3):264-72.

Warren et al., "Metabolic balances of strontium in man," Clin Orthop Relat Res Jun. 1976;(117):307-20.

Office Action dated Jul. 6, 2007 issued for U.S. Appl. No. 11/269,289.

Office Action dated Nov. 13, 2007 issued for U.S. Appl. No. 11/269,289.

Office Action dated Aug. 22, 2008 issued for U.S. Appl. No. 11/269,289.

Notice of Allowance and Notice of Allowability dated May 22, 2008 issued for U.S. Appl. No. 11/269,289.

Supplemental Notice of Allowability dated Jul. 7, 2009 issued for U.S. Appl. No. 11/269,289.

Huriet et al., 1973, "Depistage Isotopique de l'Osteonecrose," Nouvelle Presse Medicale, Press Medicale, Paris, Fr. 2(9):83, as cited in the International Search Report mailed Jul. 26, 2005 of International Application No. PCT/DK2005/000140 (Reference C142).

Adams et al., 1999, "Resolution of Vitamin D Insufficiency in Osteopenic PatientsRresults in Rapid Recovery of Mineral Density," J. Clin. Endocrinol. Metab. 84:2729-2730.

Allen et al., 2005, "Ansel's Pharmaceutical Dosage Forms and Drug Delivery Systems," 8th edition, p. 130.

Astrand et al., 2002, "Systemic alendronate prevents resorption of necrotic bone during revascularizaton. A bone chamber study in rats," BMC Musculoskeletal Disorders 3(19):1-5.

Bacce et al., 2001, "Thermal decomposition and rehydration of strontium oxalate: morphoplogical evalution." International Journal of Inorganic Materials 3:443-452.

Barlow, 2003, "Strontium and Osteoporosis," Journal of the British Menopause Society, Mar. 2003 9(1):7.

Beers et al., 1999, "The Merck manual of diagnosis and therapy," 17th Edn, 1999, Merck Research Laboratories:453-454.

Briggman et al. 1977. "The Crystal Structures of Calcium Malonate Dihydrate and Strontium Malonate," Acta Cryst. B33:1900-1906.

Brousse, 2000. "Complications osteoarticulaires de la corticotherapie." Hepato-Gastro 7(3):173-178; as cited in the International Search Report mailed Jul. 26, 2005 of International Application No. PCT/DK2005/000140 (Reference C 142).

CAS Registry No. 135459-87-9.

Christgau et al., 2004, "Osteoarthritic patients with high cartilage turnover show increased responsiveness to the cartilage protecting effects of glucosamine sulphate," Clin. Exp. Rheumatol. 22:36-42.

Diastrophic dysplasia—Genetics Home Reference: [online] retrieved from the internet on Oct. 19, 2012; retrieved from http://ghr.nlm.nih.gov/condition/diastrophic-dysplasia: 4 pages.

European Search Report of European Application No. EP 04 73 1315, dated May 9, 2006.

Forsblad D'Elia et al., 2004, "Hormone replacement therapy, calcium and vitamin $D_3$ versus calcium and vitamin $D_3$ alone decreases markers of cartilage and bone metabolism in rheumatoid arthritis: a randomized controlled trial [ISRCTN46523456]," Arthritis Res. Ther. 6(5):R457-R468.

Greenberg, 2004, "Intravenous bisphosphonates and osteonecrosis," Oral Surg. Oral Med. Oral Pathol. Oral Radiol. Endod. 98(3):259-260.

Guay, 2001, "Adjunctive Agents in the Management of Chronic Pain," Pharmacotherapy 21(9):1070-1081.

Guo, 2003, "Drugs for Treating Osteoporosis and Promoting Bone Formation," Chin. J. Bone Tumor & Bone Disease 2(2):69-72 & 78 (English translation provided).

Henrotin et al., 2001, "Strontium Ranelate Increases Cartilage Matrix Formation," J. Bone Miner. Res. 16(2):299-308.

Huskisson et al., 1995, "Effects of Antiinlammatory Drugs on the Progression of Osteoarthritis of the Knee," J. Rheumatol. 22(10):1941-1946.

International Search Report for PCT Application No. PCT/DK2005/00307, mailed Nov. 24, 2005.

International Search Report of International Application No. PCT/DK2005/000140, mailed Jul. 26, 2005.

Sweetman, 2002, "Naproxen Sodium," Martindale—The complete drug Reference (33rd Edition), Pharmaceutical Press, London, p. 61.

Neuman, 1977, "Les anti-arthrosiques," ARS Medici 32(24), 2113-2118, as cited in Feb. 5, 2008 Communication from EPO for European Application No. 05748542.7 (enclosed).

Nordstrom et al., 1998, "Anti-collagenolytic mechanism of action of doxycycline treatment in rheumatoid arthritis," Rheumatol. Int. 17(5):175-180.

Notice of Allowance and Notice of Allowability mailed May 5, 2009 for U.S. Appl. No. 11/579,773.

Office Action mailed Jan. 23, 2008 for U.S. Appl. No. 10/556,150.

Office Action mailed May 13, 2008 for U.S. Appl. No. 11/579,773.

Office Action mailed May 15, 2008 for U.S. Appl. No. 10/556,149.

Office Action mailed Sep. 30, 2008 for U.S. Appl. No. 11/579,773.

Office Action mailed Apr. 11, 2012 for U.S. Appl. No. 12/434,971.

Pelletier et al., 1989. "In Vitro Effects of Tiaprofenic Acid, Sodium Salicylate and Hydrocortisone on the Proteoglycan Metabolism of Human Osteoarthritic Cartilage," J. Rheumatol. 16(5):646-655.

Pelletier et al., 1994, "Intraarticular injections with methylprednisolone acetate reduce osteoarthritic lesions in parallel with chondrocyte stromelysin synthesis in experimental osteoarthritis," Arthritis & Rheumatism 37(3):414-423.

Pelletier et al., 1995, "The In Vivo Effects of Intraarticular Corticosteroid Injections on Cartilage Lesions, Stromelysin, Interleukin-1, and Oncogene Protein Synthesis in Experimental Osteoarthritis," Laboratory Investigation 72(5):578-586.

Poole. 1999. "An introduction to the pathophysiology of osteoarthritis," Frontiers in Bioscience 4:d662-670.

Preliminary Amendment filed Nov. 7, 2005 for U.S. Appl. No. 10/556,149.

Preliminary Amendment filed Nov. 7, 2005 for U.S. Appl. No. 10/556,150.

Preliminary Amendment filed Aug. 24, 2005 for U.S. Appl. No. 10/590,892.

Preliminary Amendment filed Jan. 4, 2008 for U.S. Appl. No. 11/994,695.

Reginster, 2003, "Strontium Ranelate," Drugs of the Future 28(4):328-335.

Richards, 2004, "Matrix Catabolism in Arthritis: Priming the Guns with Oncostatin M," Rheumatol. 31(12):2326-2328.

Robinson et al., 2004, "Bisphophonates—A word of caution," Ann. Acad. Med. 33(4 Suppl):48S-49S.

Soerdjbalie-Maikoe et al., 2002, "Strontium-89 (Metastron) and the bisphosphonate olpadronate reduce the incidence of spinal cord compression in patients with hormone-refractory prostate cancer metastatic to the skeleton," Eur. J. Nucl. Med. 29:494-498.

Sreekanth et al., 2000, "Doxycycline in the Treatment of Rheumatoid Arthriris—A Pilot Study," J. Assoc. Physicians India 48(8):804-807.

"X-linked spondyloepiphyseal dysplasia tarda—Genetics Home Reference": [online] retrieved from the internet on Nov. 2, 2008; retrieved from http://ghr.nlm.nih.gov/condition=xlinkedspondyloepiphysealdysplasiatarda/show/print; 4 pages.

Yu et al., 1992, "Reduction of the severity of canine osteoarthritis by prophylactic treatment with oral doxycycline," Arthritis Rheum. 35(10):1150-1159.

\* cited by examiner

α-ketogluterate

L-aspartate

Chloride

L-glutamate

Malonate

Pre-dose

α-ketogluterate

Glutamate

WATER-SOLUBLE STRONTIUM SALTS FOR USE IN TREATMENT OF CARTILAGE AND/OR BONE CONDITIONS

CROSS-REFERENCE TO RELATED APPLICATIONS

This application is a continuation of U.S. patent application Ser. No. 11/269,289 filed Nov. 7, 2005 now U.S. Pat. No. 7,595,342 which is a continuation-in-part of International Application No. PCT/DK2004/000328, filed May 6, 2004, which claims the benefit of Provisional Application No. 60/528,442, filed Dec. 9, 2003, and also claims the benefit of priority of Denmark Application No. PA 2003 01820, filed Dec. 9, 2003, and also claims the benefit of Denmark Application No. PA 2003 00932, filed Jun. 20, 2003, and also claims the benefit of Denmark Application No. PA 2003 00691, filed May 7, 2003, the disclosures all of which are hereby incorporated by reference in their entireties. This application is also a continuation-in-part of International Application No. PCT/DK2005/000140, filed Feb. 28, 2005, and also a continuation-in-part of PCT/DK2005/000404, filed Jun. 17, 2005, and also a continuation-in-part of PCT/DK2005/000401, filed Jun. 17, 2005, the disclosures all of which are hereby incorporated by reference in their entireties.

FIELD OF THE INVENTION

The present invention relates to compounds and pharmaceutical compositions for use in the treatment and/or prophylaxis of cartilage and/or bone conditions and for methods of treating such conditions. The compounds are salts of strontium that have a water-solubility of from about 1 g/l to about 100 g/l at room temperature, especially amino acid salts of strontium or dicarboxylic acid salts of strontium. Examples of novel water-soluble strontium salts are e.g. strontium aspartate and strontium alpha-ketoglutarate.

The present invention also relates to an improved method for preparing the strontium salt of glutamic acid.

BACKGROUND OF THE INVENTION

Osteoporosis is the most common form of metabolic bone disease in humans. It is a condition, which affects a very large number of people all over the world, and as the number of elderly people is set to rise dramatically in the coming decades in most countries, the prevalence and impact of osteoporosis will also increase. The disease is characterized pathologically by an absolute decrease in the amount of bone mass and the structural quality of bone, and clinically by increased susceptibility to fractures. In fact, osteoporosis is the most significant underlying cause of skeletal fractures in late middle aged and elderly women.

In general, there are two types of osteoporosis: primary and secondary. Secondary osteoporosis is the result of an identifiable disease process or agent. However, approximately 90% of all osteoporosis cases are idiopathic primary osteoporosis. Such primary osteoporosis includes postmenopausal osteoporosis, age-associated osteoporosis (affecting a majority of individuals over the age of 70 to 80), and idiopathic osteoporosis affecting middle-aged and younger men and women.

The mechanism of bone loss in osteoporosis is believed to involve an imbalance in the process of bone remodeling. Bone remodeling occurs throughout life, renewing the skeleton and maintaining the strength of bone. This remodeling is mediated by specialized cells of the bone tissue, called "osteoclasts" and "osteoblasts". Osteoclasts (bone dissolving or resorbing cells) are responsible for the resorption of a portion of bone within the bone matrix, during the resorption process. After resorption, the osteoclasts are followed by the appearance of osteoblasts (bone forming cells), which then refill the resorbed portion with new bone.

The formation of the two cell types as well as their activity in bone is usually tightly coupled and well regulated in order to maintain the skeletal balance and structural integrity of the bones. However, in people with osteoporosis an imbalance in this remodeling process develops, resulting in loss of bone at a rate faster than the accretion of bone.

The single most important risk factor for osteoporosis is oestrogen deficiency occurring naturally at the menopause. The decline in endogenous oestrogen production leads to an elevated metabolic activity in the bone tissue where the increase in osteoclast mediated bone resorption surpasses the more modest increase in bone formation resulting in a net loss of bone. The actual number of people affected will grow at a rate greater than simple population growth rates, because the aging of the population is disproportionately increasing the older segment of the population, while the age for the onset of menopause has remained constant. In the last decades there has also been a substantial advance in the ability to predict and monitor osteoporosis, as methods for measurement of bone mineral density (BMD) has improved and new specific biochemical markers of bone resorption and formation has been developed and made available for routine clinical use. New pharmaceutical agents for treatment and/or prevention of osteoporosis have also been developed. The majority of these treatments are either based on substituting the lost endogenous estrogen either in the form of hormone replacement therapy (HRT) or selective estrogen receptor modulators (SERM), or they belong to the class of compounds called bisphosphonates. SERM's and especially HRT is associated with significant side effects, such as increased risk of cancer and cardiovascular disease, whereas bisphosphonates in addition to a potent antiresorptive effect also decreases bone formation to a similar extent, implying that they loose their therapeutic effect after few years of treatment. Thus, there is a need for agents, which are effective in the treatment and/or prophylaxis of osteoporosis.

SUMMARY OF THE INVENTION

In one aspect, the invention relates to use of a strontium salt having a water-solubility at room temperature in a range of from about 1 g/l to about 100 g/l in medicine. In some embodiments of the use, the strontium salt is formed between strontium and an organic or inorganic acid. In certain embodiments, the organic acid is a mono-, di-, tri- or quatro-carboxylic acid. In specific embodiments of the use, the organic acid is an amino carboxylic acid. In specific embodiments, the amino carboxylic acid has a linear or branched carbon chain of from 2 to 25 carbon atoms and one or more amino groups attached thereto. The amino carboxylic acid is a natural or synthetic amino acid.

In some embodiments of the use, the salt comprises strontium glutamate, strontium aspartate, strontium malonate, strontium maleate, strontium ascorbate, strontium threonate, strontium lactate, strontium pyruvate, strontium alpha-ketoglutarate or strontium succinate. In specific embodiments, the salt comprises strontium D-glutamate, strontium L-glutamate, strontium D-aspartate, strontium L-aspartate, strontium D-threonate or strontium L-threonate.

In some embodiments, the invention relates to use of a strontium salt having a water-solubility at room temperature in a range of from about 1 g/l to about 100 g/l for the preparation of a pharmaceutical composition for the treatment of and/or prophylaxis of a cartilage and/or bone disease and/or conditions resulting in a dysregulation of cartilage and/or bone metabolism in a mammal, such as, e.g., a human female or male adult, adolescent or a child, such as, e.g., osteoporosis, osteoarthritis, osteopetrosis, osteopenia and Paget's disease, hypercalcemia of malignancy, periodontal disease, hyperparathyroidism, periarticular erosions in rheumatoid arthritis, osteodystrophy, myositis ossificans, Bechterew's disease, malignant hypercalcemia, osteolytic lesions produced by bone metastasis, bone pain due to bone metastasis, bone loss due to sex steroid hormone deficiency, bone abnormalities due to steroid hormone treatment, bone abnormalities caused by cancer therapeutics, osteomalacia, Bechet's disease, hyperostosis, metastatic bone disease, immobilization-induced osteopenia or osteoporosis, or glucocorticoid-induced osteopenia or osteoporosis, osteoporosis pseudoglioma syndrome, idiopathic juvenile osteoporosis, for the improvement of fracture healing after traumatic or atraumatic fracture, and for the maintenance or increase of energy level, for building up or strengthening muscle tissues and for weight gain. The strontium salt used may be, for example, any of those described above.

In specific embodiments of the use, the salt is administered using a pharmaceutical composition designed for oral or parenteral administration. For instance, in specific embodiments, the pharmaceutical composition is in the form of tablets, capsules, sachets, powders, pellets, granules, granulates, mixtures, syrups, solutions, suspensions, emulsions, or the like, for oral administration. In certain embodiments, the pharmaceutical composition is in the form of a solution, suspension or emulsion, or the like, for intravenous, intramuscular, intraartricular or subcutaneous injection. In specific embodiments, the pharmaceutical composition is in the form of a toothpaste or a mouthwash intended for application to the teeth or to the oral mucosa.

In another aspect, the invention relates to a strontium salt having a water-solubility at room temperature in a range of from about 1 g/l to about 100 g/l with the proviso that the salt is not strontium L-aspartate trihydrate or strontium L-glutamate hexahydrate as defined by the properties disclosed in FIGS. 1-3 and Tables 2-5.

In some embodiments, the salt is formed between strontium and an organic or inorganic acid. In certain embodiments, the organic acid is a mono-, di-, tri- or tetra-carboxylic acid. In certain embodiments, the organic acid is an amino carboxylic acid. The amino carboxylic acid can have, for example, a linear or branched carbon chain of from 2 to 25 carbon atoms and one or more amino groups attached thereto. The amino carboxylic acid is a natural or synthetic amino acid.

In some embodiments, the salt comprises strontium glutamate, strontium aspartate, strontium malonate, strontium maleate, strontium ascorbate, strontium threonate, strontium lactate, strontium pyruvate, strontium alpha-ketoglutarate or strontium succinate. In certain embodiments, the salt comprises strontium D-glutamate, strontium D-aspartate, strontium D-threonate or strontium L-threonate. In a specific embodiment, the salt is strontium L-glutamate prepared by reacting strontium chloride with L-glutamic acid as described in Example 4 and having the X-ray diffraction pattern as shown herein.

In another aspect, the invention relates to a method for the treatment of and/or prophylaxis of a cartilage and/or bone disease and/or conditions resulting in a dysregulation of cartilage and/or bone metabolism in a mammal, such as, e.g., a human female or male adult, adolescent or a child, such as, e.g., osteoporosis, osteoarthritis, osteopetrosis, osteopenia and Paget's disease, hypercalcemia of malignancy, periodontal disease, hyperparathyroidism, periarticular erosions in rheumatoid arthritis, osteodystrophy, myositis ossificans, Bechterew's disease, malignant hypercalcemia, osteolytic lesions produced by bone metastasis, bone pain due to bone metastasis, bone loss due to sex steroid hormone deficiency, bone abnormalities due to steroid hormone treatment, bone abnormalities caused by cancer therapeutics, osteomalacia, Bechet's disease, hyperostosis, metastatic bone disease, immobilization-induced osteopenia or osteoporosis, or glucocorticoid-induced osteopenia or osteoporosis, osteoporosis pseudoglioma syndrome, idiopathic juvenile osteoporosis, for the improvement of fracture healing after traumatic or atraumatic fracture, and for the maintenance or increase of energy level, for building up or strengthening muscle tissues and for weight gain, the method comprising administering to a subject in need thereof an effective amount of a strontium salt that has a water-solubility of from about 1 g/l to about 100 g/l at room temperature. In certain embodiments, the strontium salt can be any of those as described above.

In some embodiments of the method, the daily dose of ionic strontium is at least about 0.01 g, such as, e.g. at least about 0.025 g, at least about 0.050 g, at least about 0.075 g, at least about 0.1 g, at least about 0.2 g, at least about 0.3 g, at least about 0.4 g or at least about 0.5 g or from about 0.01 g to about 2 g such as, e.g., from about 0.1 g to about 2 g, from about 0.3 g to about 2 g or from about 0.3 g to about 1 g.

In some embodiments of the method, the administration takes place one or more times daily. For instance, the administration can take place from 2-5 times daily. In a specific embodiment, the administration takes place at bedtime.

In some embodiments of the method, the peak concentration of strontium after oral administration is delayed compared to that of strontium chloride. In a specific embodiment, the peak concentration of strontium is reached at least 2.5 hours after oral administration.

In a specific aspect, the invention relates to a method for the treatment of and/or prophylaxis of a bone disease and/or condition resulting in a dysregulation of bone metabolism in a mammal (e.g., a human) in need thereof, the method comprising administering a therapeutically effective amount or prophylactically effective amount of strontium malonate to the mammal. The bone disease or condition may be, for instance, osteoporosis, osteoarthritis, osteopetrosis, osteopenia and Paget's disease, hypercalcemia of malignancy, periarticular erosions in rheumatoid arthritis, osteodystrophy, myositis ossificans, Bechterew's disease, malignant hypercalcemia, osteolytic lesions produced by bone metastasis, bone loss due to sex steroid hormone deficiency, bone abnormalities due to steroid hormone treatment, bone abnormalities caused by cancer therapeutics, osteomalacia, Bechet's disease, hyperostosis, metastatic bone disease, immobilization-induced osteopenia or osteoporosis, or glucocorticoid-induced osteopenia or osteoporosis, osteoporosis pseudoglioma syndrome, idiopathic juvenile osteoporosis, or for the improvement of fracture healing after traumatic or atraumatic fracture. In a specific embodiment, the bone disease is osteoporosis.

In some embodiments of the method, the water solubility of the strontium malonate at room temperature is in a range of from about 1 g/l to about 100 g/l.

In some embodiments of the method, the strontium malonate is administered orally. In certain embodiments, the strontium malonate is administered at bedtime.

Another specific aspect of the invention relates to a method for the treatment of and/or prophylaxis of a disorder and/or condition resulting in a dysregulation of a disorder and/or condition selected from the group consisting of periodontal disease, hyperparathyroidism and bone pain due to bone metastasis in a mammal in need thereof, the method comprising administering a therapeutically effective amount or prophylactically effective amount of strontium malonate to the mammal.

In another aspect, the invention relates to a pharmaceutical composition comprising a strontium salt having a water-solubility from about 1 g/l to about 100 g/l at room temperature together with one or more pharmaceutically acceptable excipients. In some embodiments of the pharmaceutical composition, the strontium salt can be any of those described above.

In a specific aspect, the invention relates to a pharmaceutical composition comprising a therapeutically effective amount of strontium malonate for the treatment of and/or prophylaxis of a bone disease and/or condition resulting in a dysregulation of bone metabolism in a mammal, and one or more pharmaceutically acceptable excipients. In some embodiments, the water solubility of the strontium malonate at room temperature is in a range of from about 1 g/l to about 100 g/l.

In some embodiments, the pharmaceutical composition is in the form of an oral composition. For instance, the pharmaceutical composition may be in the form of tablets, capsules, sachets, powders, pellets, granules, granulates, syrups, solutions, suspensions or emulsions. In specific embodiments, the pharmaceutical composition is in the form of a tablet or capsule.

In certain embodiments of the pharmaceutical composition, the composition is in the form of a tablet, comprising at least 75% w/w of strontium malonate. The pharmaceutical composition may comprise, for instance, from about 75% w/w to about 90% w/w of strontium malonate; from about 5% w/w to about 15% w/w of filler; from about 1% w/w to about 8% w/w of binder; and from about 0.5% w/w to about 5% w/w of lubricant. In a specific embodiment, the filler comprises microcrystalline cellulose and colloidal anhydrous silica; the binder comprises polyvidone; and the lubricant comprises magnesium stearate and colloidal anhydrous silica.

In other embodiments of the pharmaceutical composition comprising strontium malonate, the composition comprises no more than 25% w/w of the one or more pharmaceutically acceptable excipients. For instance, the tablet may comprise from about 10 to about 25% w/w of the one or more pharmaceutically acceptable excipients.

In some embodiments of the pharmaceutical composition comprising strontium malonate, the composition comprises from about 0.02 g to about 4.3 g of strontium malonate. For instance in certain embodiments, the pharmaceutical composition comprises from about 0.6 g to about 4.3 g, from about 0.6 g to about 2.2 g, or from about 0.2 g to about 4.3 g of strontium malonate.

In yet another aspect, the invention relates to the preparation of a strontium salt having a water-solubility of from about 1 g/l to about 100 g/l at room temperature, the method comprising reacting strontium hydroxide with the appropriate acid (anion) in an aqueous medium at a temperature of about 90° C. or more, e.g., 100° C. or more, about 120° C. or more, or about 125° C. or more for a time period of at the most about 60 min such as, at the most about 30 min or at the most about 20 min such as about 15 min. In a specific embodiment of the method, the molar ratio between strontium hydroxide and the organic anion is at least 1:1, preferably above 1.1:1.

In another aspect, the invention relates to a method for the treatment of and/or prophylaxis of a bone disease and/or condition resulting in a dysregulation of bone metabolism in a subject, comprising administering a strontium salt to the subject, wherein the strontium salt provides a maximum plasma concentration of strontium from about 4 to about 24 hours after administration to said subject. In a specific embodiment, the strontium salt is not strontium ranelate. In certain embodiments, the administration comprises oral administration of the strontium salt to the subject. The administration may, for example, include administration of a tablet to the subject.

In some embodiments, the strontium salt provides a maximum plasma concentration of strontium from about 5.5 to 24 hours, e.g., from about 5.5 to about 10 hours, after administration to the subject. In other embodiments, the strontium salt provides a maximum plasma concentration from about 4 to about 8 hours, or from about 5 to about 10 hours, after administration to said subject.

In some embodiments of the method of treatment, the bone disease or condition comprises osteoporosis, osteoarthritis, osteopetrosis, osteopenia, Paget's disease, hypercalcemia of malignancy, periarticular erosions in rheumatoid arthritis, osteodystrophy, myositis ossificans, Bechterew's disease, malignant hypercalcemia, osteolytic lesions produced by bone metastasis, bone loss due to sex steroid hormone deficiency, bone abnormalities due to steroid hormone treatment, bone abnormalities caused by cancer therapeutics, osteomalacia, Bechet's disease, hyperostosis, metastatic bone disease, immobilization-induced osteopenia or osteoporosis, or glucocorticoid-induced osteopenia or osteoporosis, osteoporosis pseudoglioma syndrome, idiopathic juvenile osteoporosis, or fracture healing after traumatic or atraumatic fracture.

In certain embodiments of the method, the maximum plasma concentration of strontium is at least 1.5 times higher than the plasma concentration of strontium at 2 hours after administration to the subject. In a specific embodiment of the method, the maximum plasma concentration of strontium in the subject is from about 2 mg/L to about 10 mg/L.

In some embodiments of the method, the strontium salt administered provides a dose from about 0.01 to about 2 g of strontium. For example, in some embodiments, the strontium salt administered provides a dose from about 0.1 to about 2 g of strontium.

In a specific embodiment of the method, the strontium salt is strontium malonate.

In another embodiment, the invention relates to a method for the treatment of and/or prophylaxis of a bone disease and/or condition resulting in a dysregulation of bone metabolism in a subject, comprising administering to the subject a pharmaceutical composition comprising a strontium salt and one or more pharmaceutically acceptable excipients, wherein the pharmaceutical composition provides a maximum plasma concentration of strontium from about 4 to about 24 hours after administration to said subject. In a specific embodiment, the strontium salt is not strontium ranelate. In certain embodiments, the administration comprises oral administration of the pharmaceutical composition to said subject. The pharmaceutical composition may be, for example, a tablet.

In some embodiments of the method, the pharmaceutical composition provides a maximum plasma concentration of strontium from about 5.5 to 24 hours, e.g., from about 5.5 to about 10 hours, after administration to the subject. In other embodiments, the pharmaceutical composition provides a maximum plasma concentration from about 4 to about 8 hours, or from about 5 to about 10 hours, after administration to said subject.

In some embodiments of the method of treatment, the bone disease or condition comprises osteoporosis, osteoarthritis, osteopetrosis, osteopenia, Paget's disease, hypercalcemia of malignancy, periarticular erosions in rheumatoid arthritis, osteodystrophy, myositis ossificans, Bechterew's disease, malignant hypercalcemia, osteolytic lesions produced by bone metastasis, bone loss due to sex steroid hormone deficiency, bone abnormalities due to steroid hormone treatment, bone abnormalities caused by cancer therapeutics, osteomalacia, Bechet's disease, hyperostosis, metastatic bone disease, immobilization-induced osteopenia or osteoporosis, or glucocorticoid-induced osteopenia or osteoporosis, osteoporosis pseudoglioma syndrome, idiopathic juvenile osteoporosis, or fracture healing after traumatic or atraumatic fracture.

In certain embodiments of the method, the maximum plasma concentration of strontium is at least 1.5 times higher than the plasma concentration of strontium at 2 hours after administration to said subject. In a specific embodiment of the method, the maximum plasma concentration of strontium is from about 2 mg/L to about 10 mg/L.

In some embodiments of the method, the pharmaceutical composition administered provides a dose from about 0.01 to about 2 g of strontium. For example, in some embodiments, the pharmaceutical composition administered provides a dose from about 0.1 to about 2 g of strontium.

In another aspect, the invention relates to a method for the treatment of and/or prophylaxis of a bone disease and/or condition resulting in a dysregulation of bone metabolism in a subject, comprising administering to the subject a pharmaceutical composition comprising strontium malonate and one or more pharmaceutically acceptable excipients, wherein the pharmaceutical composition provides a maximum plasma concentration of strontium from about 4 to about 24 hours after administration to the subject. In certain embodiments, the administration comprises oral administration of the pharmaceutical composition to the subject. The pharmaceutical composition may be, for example, a tablet.

In some embodiments of the method, the pharmaceutical composition provides a maximum plasma concentration of strontium from about 5.5 to 24 hours, e.g., from about 5.5 to about 10 hours, after administration to the subject. In other embodiments, the pharmaceutical composition provides a maximum plasma concentration from about 4 to about 8 hours, or from about 5 to about 10 hours, after administration to said subject.

In certain embodiments of the method, the bone disease or condition comprises osteoporosis, osteoarthritis, osteopetrosis, osteopenia, Paget's disease, hypercalcemia of malignancy, periarticular erosions in rheumatoid arthritis, osteodystrophy, myositis ossificans, Bechterew's disease, malignant hypercalcemia, osteolytic lesions produced by bone metastasis, bone loss due to sex steroid hormone deficiency, bone abnormalities due to steroid hormone treatment, bone abnormalities caused by cancer therapeutics, osteomalacia, Bechet's disease, hyperostosis, metastatic bone disease, immobilization-induced osteopenia or osteoporosis, or glucocorticoid-induced osteopenia or osteoporosis, osteoporosis pseudoglioma syndrome, idiopathic juvenile osteoporosis, or fracture healing after traumatic or atraumatic fracture.

In certain embodiments of the method, the maximum plasma concentration of strontium is at least 1.5 times higher than the plasma concentration of strontium at 2 hours after administration to the subject. In a specific embodiment of the method, the maximum plasma concentration of strontium is from about 2 mg/L to about 10 mg/L.

In some embodiments of the method, the pharmaceutical composition administered provides a dose from about 0.01 to about 2 g of strontium. For example, in some embodiments, the pharmaceutical composition administered provides a dose from about 0.1 to about 2 g of strontium.

In yet another embodiment, the invention relates to a pharmaceutical composition comprising a strontium salt and one or more pharmaceutically acceptable excipients, wherein the pharmaceutical composition provides a maximum plasma concentration of strontium from about 4 to about 24 hours after administration of the pharmaceutical composition to a subject. In a specific embodiment, the strontium salt is not strontium ranelate.

In certain embodiments, the pharmaceutical composition provides a maximum plasma concentration of strontium from about 5.5 to 24 hours, e.g., from about 5.5 to about 10 hours, after administration to the subject. In other embodiments, the pharmaceutical composition provides a maximum plasma concentration from about 4 to about 8 hours, or from about 5 to about 10 hours, after administration to said subject.

In some embodiments of the pharmaceutical composition, the maximum plasma concentration of strontium is at least 1.5 times higher than the plasma concentration of strontium at 2 hours after administration of the pharmaceutical composition to the subject. In a specific embodiment, the maximum plasma concentration of strontium is from about 2 mg/L to about 10 mg/L.

In certain embodiments, the pharmaceutical composition comprises from about 0.01 to about 2 g of strontium. For instance, the pharmaceutical composition may comprise from about 0.1 to about 2 g of strontium.

In a specific embodiment, the pharmaceutical composition comprises a tablet.

In another aspect, the invention relates to a pharmaceutical composition comprising strontium malonate and one or more pharmaceutically acceptable excipients, wherein the pharmaceutical composition provides a maximum plasma concentration of strontium from about 4 to about 24 hours after administration of the pharmaceutical composition to a subject.

In certain embodiments, the pharmaceutical composition provides a maximum plasma concentration of strontium from about 5.5 to 24 hours, e.g., from about 5.5 to about 10 hours, after administration to the subject. In other embodiments, the pharmaceutical composition provides a maximum plasma concentration of strontium from about 5 to about 10 hours, or from about 4 to about 8 hours, after administration to said subject.

In certain embodiments of the pharmaceutical composition, the bone disease or condition comprises osteoporosis, osteoarthritis, osteopetrosis, osteopenia, Paget's disease, hypercalcemia of malignancy, periarticular erosions in rheumatoid arthritis, osteodystrophy, myositis ossificans, Bechterew's disease, malignant hypercalcemia, osteolytic lesions produced by bone metastasis, bone loss due to sex steroid hormone deficiency, bone abnormalities due to steroid hormone treatment, bone abnormalities caused by cancer therapeutics, osteomalacia, Bechet's disease, hyperostosis, metastatic bone disease, immobilization-induced osteopenia or osteoporosis, or glucocorticoid-induced osteopenia or osteoporosis, osteoporosis pseudoglioma syndrome, idiopathic juvenile osteoporosis, or fracture healing after traumatic or atraumatic fracture.

In certain embodiments of the pharmaceutical composition, the maximum plasma concentration of strontium is at least 1.5 times higher than the plasma concentration of strontium at 2 hours after administration to said subject. In a specific embodiment of the method, the maximum plasma concentration of strontium is from about 2 mg/L to about 10 mg/L.

In some embodiments, the pharmaceutical composition provides a dose from about 0.01 to about 2 g of strontium. For example, in some embodiments, the pharmaceutical composition administered provides a dose from about 0.1 to about 2 g of strontium.

In a specific embodiment, the pharmaceutical composition comprises a tablet.

In yet another aspect, the invention relates to a method for the treatment of and/or prophylaxis of a bone disease and/or condition resulting in a dysregulation of bone metabolism in a subject, comprising administering to the subject a pharmaceutical composition comprising a strontium salt and one or more pharmaceutically acceptable excipients to provide a steady state plasma concentration of from about 5 to about 50 mg/L of strontium in said subject after repeated administration through steady state conditions, wherein the strontium salt is not strontium ranelate. In some embodiments, the administration includes oral administration (such as with a tablet) to the subject.

In specific embodiments of the method, the steady state plasma concentration provided in the subject is from about 8 to about 20 mg/L of strontium.

In another aspect, the invention relates to a pharmaceutical composition comprising a strontium salt and one or more pharmaceutically acceptable excipients, wherein the pharmaceutical composition provides a steady state plasma concentration in a subject of from about 5 to about 50 mg/L of strontium after repeated administration of the pharmaceutical composition to said subject through steady state conditions, wherein the strontium salt is not strontium ranelate.

In specific embodiments, the pharmaceutical composition provides a steady state plasma concentration in a subject of from about 8 to about 20 mg/L of strontium after repeated administration of the pharmaceutical composition to said subject through steady state conditions.

In some embodiments, the pharmaceutical composition comprises from about 0.01 to about 2 g of strontium.

In a specific embodiment, the pharmaceutical composition comprises a tablet.

In yet another aspect, the invention relates to a method for the treatment of and/or prophylaxis of a bone disease and/or condition resulting in a dysregulation of bone metabolism in a subject, comprising administering to the subject a pharmaceutical composition comprising strontium malonate and one or more pharmaceutically acceptable excipients to provide a steady state plasma concentration of from about 5 to about 50 mg/L of strontium in said subject after repeated administration through steady state conditions. In some embodiments, the administration comprises oral administration of the pharmaceutical composition. In a specific embodiment of the method, the pharmaceutical composition comprises a tablet.

In some embodiments of the method, the steady state plasma concentration provided in the subject is from about 8 to about 20 mg/L of strontium.

In another aspect, the invention relates to a pharmaceutical composition comprising strontium malonate and one or more pharmaceutically acceptable excipients, wherein the pharmaceutical composition provides a steady state plasma concentration in a subject of from about 5 to about 50 mg/L of strontium after repeated administration of the pharmaceutical composition to the subject through steady state conditions.

In certain embodiments, the pharmaceutical composition provides a steady state plasma concentration in a subject of from about 8 to about 20 mg/L of strontium after repeated administration of the pharmaceutical composition to the subject through steady state conditions.

In specific embodiments, the pharmaceutical composition comprises from about 0.01 to about 2 g of strontium.

In a specific embodiment, the pharmaceutical composition comprises a tablet.

In other aspects, the invention relates to the following items:

1. A strontium salt of alpha-ketoglutamic acid of the formula I:

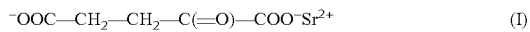

$$^{-}OOC-CH_2-CH_2-C(=O)-COO^{-}Sr^{2+} \qquad (I)$$

2. A salt according to item I in hydrate, anhydrous, solvate, polymorphous, amorphous, crystalline, microcrystalline or polymeric form.
3. A salt according to item 1 or 2 for use as a medicine.
4. Use of a salt according to any of items 1-3, for the preparation of a pharmaceutical composition for the treatment and/or prophylaxis of a cartilage and/or bone disease and/or conditions resulting in a dysregulation of cartilage and/or bone metabolism in a mammal, such as, e.g., a human female or male adult, adolescent or a child, such as, e.g., osteoporosis, osteoarthritis, osteopetrosis, osteopenia and Paget's disease, hypercalcemia of malignancy, periodontal disease, hyperparathyroidism, periarticular erosions in rheumatoid arthritis, osteodystrophy, myositis ossificans, Bechterew's disease, malignant hypercalcemia, osteolytic lesions produced by bone metastasis, bone pain due to bone metastasis, bone loss due to sex steroid hormone deficiency, bone abnormalities due to steroid hormone treatment, bone abnormalities caused by cancer therapeutics, osteomalacia, Bechet's disease, hyperostosis, metastatic bone disease, immobilization-induced osteopenia or osteoporosis, or glucocorticoid-induced osteopenia or osteoporosis, osteoporosis pseudoglioma syndrome, idiopathic juvenile osteoporosis, for the improvement of fracture healing after traumatic or atraumatic fracture, and for the maintenance or increase of energy level, for building up or strengthening muscle tissues and for weight gain.
5. A process for preparing a salt according to any of items 1-3, the process comprising reacting alpha-ketoglutamic acid with strontium hydroxide and/or strontium oxide.
6. A pharmaceutical composition comprising an amount of a salt according to any of items 1-3, together with one or more physiologically acceptable excipients.
7. A pharmaceutical composition according to item 6, further comprising an additional amount of a strontium-containing compound.
8. A pharmaceutical composition comprising a therapeutically and/or prophylactically effective amount of one or more first components containing a strontium compound and one or more second components containing an alpha-ketoglutarate compound, together with one or more physiologically acceptable excipients.
9. A pharmaceutical composition according to any of items 6-8, wherein the strontium-containing compound is selected from the group consisting of strontium salts of an organic or an inorganic acid.
10. A pharmaceutical composition according to item 9, wherein the inorganic acid is selected from the group consisting of hydrofluoric acid, hydrochloric acid, hydrobromic acid, hydroiodic acid, nitric acid, nitrous acid, phosphoric acid, phosphinic acid, phosphonic acid, sulfonic acid, sulfuric acid, sulfurous acid, disulfuric acid and boric acid.

11. A pharmaceutical composition according to item 9, wherein the organic acid is selected from the group consisting of acetic acid, $C_2H_5COOH$, $C_3H_7COOH$, $C_4H_9COOH$, $(COOH)_2$, $CH_2(COOH)_2$, $C_2H_4(COOH)_2$, $C_3H_6(COOH)_2$, $C_4H_8(COOH)_2$, $C_5H_{10}(COOH)_2$, fumaric acid, maleic acid, malonic acid, lactic acid, citric acid, tartaric acid, oxalic acid, ascorbic acid, benzoic acid, salicylic acid, phthalic acid, carbonic acid, formic acid, methanesulfonic acid, ethanesulfonic acid, benzenesulfonic acid, camphoric acid, gluconic acid, L-glutamic acid, D-glutamic acid, L-aspartic acid, D-aspartic acid, trifluoroacetic acid and ranelic acid.

12. A pharmaceutical composition according to any of items 9-11, wherein the acid is a non-chelator of strontium.

13. A pharmaceutical composition according to any of items 9-12, wherein the salt is in hydrate, anhydrous, solvate, polymorphous, amorphous, crystalline, microcrystalline or polymeric form.

14. A pharmaceutical composition according to any of items 9-13, wherein the salt is water soluble.

15. A pharmaceutical composition according to item 14, wherein the salt has a water solubility of at least 1 g/l, such as, e.g., at least 5 g/l, at least 10 g/l, at least 20 g/l, at least 30 g/l, at least 40 g/l, at least 50 g/l, at least 60 g/l, at least 70 g/l, at least 80 g/l, at least 90 g/l or at least 100 g/1 measured at a temperature of 25° C.

16. A pharmaceutical composition according to any of items 9-15, wherein the salt is selected from the group comprising strontium chloride, strontium chloride hexahydrate, strontium citrate, strontium malonate, strontium succinate, strontium fumarate, strontium ascorbate, strontium L-glutamate, strontium D-glutamate, strontium L-aspartate, strontium D-aspartate, strontium pyruvate, strontium tartrate, strontium glutarate, strontium maleate, strontium methanesulfonate, strontium benzenesulfonate and mixtures thereof.

17. A pharmaceutical composition according to any of items 9-16, wherein the acid is a monoprotic or a diprotic acid.

18. A pharmaceutical composition according to any of items 9-17, wherein the salt is selected from the group consisting of strontium bromide, strontium bromide hexahydrate, strontium acetate, strontium carbonate, strontium gluconate, strontium lactate, strontium ranelate and mixtures thereof.

19. A pharmaceutical composition according to any of items 6-18, further comprising an additional amount of an alpha-ketoglutarate-containing compound.

20. A pharmaceutical composition according to any of items 6-19, wherein the alpha-ketoglutarate-containing compound is a salt of an alkali metal, a mixed salt of alkali metals, an alkaline earth metal, or mixtures thereof.

21. A pharmaceutical composition according to item 20, wherein the salt is selected from the group consisting of sodium alpha-ketoglutarate, potassium alpha-ketoglutarate, lithium alpha-ketoglutarate, magnesium alpha-ketoglutarate, calcium alpha-ketoglutarate and mixtures thereof.

22. A pharmaceutical composition according to item 19, wherein the alpha-ketoglutarate-containing compound is a salt of an amine or an amino acid or an ammonium salt or mixtures thereof.

23. A pharmaceutical composition according to item 22, wherein the amine is selected from methyl amine, ethyl amine, propyl amine, isopropyl amine and butyl amine.

24. A pharmaceutical composition according to item 22, wherein the amino acid is selected from arginine, ornithine, lysine and histidine.

25. A pharmaceutical composition according to any of items 6-24, the composition further comprising one or more active substances.

26. A pharmaceutical composition according to item 25, wherein the one or more active substances has a therapeutic and/or prophylactic effect on a cartilage and/or bone disease and/or conditions resulting in a dysregulation of cartilage and/or bone metabolism in a mammal, such as, e.g., a human female or male adult, adolescent or a child, such as, e.g., osteoporosis, osteoarthritis, osteopetrosis, osteopenia and Paget's disease, hypercalcemia of malignancy, periodontal disease, hyperparathyroidism, periarticular erosions in rheumatoid arthritis, osteodystrophy, myositis ossificans, Bechterew's disease, malignant hypercalcemia, osteolytic lesions produced by bone metastasis, bone pain due to bone metastasis, bone loss due to sex steroid hormone deficiency, bone abnormalities due to steroid hormone treatment, bone abnormalities caused by cancer therapeutics, osteomalacia, Bechet's disease, hyperostosis, metastatic bone disease, immobilization-induced osteopenia or osteoporosis, or glucocorticoid-induced osteopenia or osteoporosis, osteoporosis pseudoglioma syndrome, idiopathic juvenile osteoporosis, for the improvement of fracture healing after traumatic or atraumatic fracture, and for the maintenance or increase of energy level, for building up or strengthening muscle tissues and for weight gain.

27. A pharmaceutical composition according to item 26, wherein the one or more active substances reduce the incidence of osteoporotic and/or non-osteoporotic bone fracture, increase bone density and/or improve healing of bone such as, e.g., anti-resorptive and/or anabolic agents.

28. A pharmaceutical composition according to item 26 or 27, wherein the one or more active substances are selected from the group consisting of calcium-alpha-ketoglutarate, calcium, calcium salts, vitamin D such as, e.g., vitamin D3 and/or functional equivalents of vitamin D3, glucagon-like peptide-2, glucagons-like peptide-2 releasing compositions, bisphosphonates, selective estrogen receptor modulators, calcitonin, parathyroid hormone, parathyroid hormone related peptide, glucosamine sulphate, glutamic acid and/or salts thereof, aspartate and/or salts thereof, proline, L-threonate, glutamine and hydroxyproline.

29. A method for the treatment and/or prophylaxis of a cartilage and/or bone disease and/or conditions resulting in a dysregulation of cartilage and/or bone metabolism in a mammal, such as, e.g., a human female or male adult, adolescent or a child, such as, e.g., osteoporosis, osteoarthritis, osteopetrosis, osteopenia and Paget's disease, hypercalcemia of malignancy, periodontal disease, hyperparathyroidism, periarticular erosions in rheumatoid arthritis, osteodystrophy, myositis ossificans, Bechterew's disease, malignant hypercalcemia, osteolytic lesions produced by bone metastasis, bone pain due to bone metastasis, bone loss due to sex steroid hormone deficiency, bone abnormalities due to steroid hormone treatment, bone abnormalities caused by cancer therapeutics, osteomalacia, Bechet's disease, hyperostosis, metastatic bone disease, immobilization-induced osteopenia or osteoporosis, or glucocorticoid-induced osteopenia or osteoporosis, osteoporosis pseudoglioma syndrome, idiopathic juvenile osteoporosis, for the improvement of fracture healing after traumatic or atraumatic fracture, and for the maintenance or increase of energy level, for building up or strengthening muscle tissues and for weight gain, the method comprising administering to a subject in need thereof an amount of the salt according to any of items 1-3.

30. A method according to item 29, wherein the salt is administered in a dose corresponding to from about 0.1 to about 17 g daily calculated as anhydrous salt.

31. A method according to item 30, wherein the salt is administered in a dose corresponding to from about 0.2 to about 15 g daily such as, e.g., from about 0.4 to about 13 g daily, from about 0.6 to about 12 g daily or from about 0.7 to about 11.5 g daily calculated as anhydrous salt.

32. A method according to any of items 29-31, further comprising administration of an additional dose of a strontium-containing compound.

33. A method according to any of items 29-32, further comprising administration of an additional dose of an alpha-ketoglutarate-containing compound.

34. A method for the treatment and/or prophylaxis of a cartilage and/or bone disease and/or conditions resulting in a dysregulation of cartilage and/or bone metabolism in a mammal, such as, e.g., a human female or male adult, adolescent or a child, such as, e.g., osteoporosis, osteoarthritis, osteopetrosis, osteopenia and Paget's disease, hypercalcemia of malignancy, periodontal disease, hyperparathyroidism, periarticular erosions in rheumatoid arthritis, osteodystrophy, myositis ossificans, Bechterew's disease, malignant hypercalcemia, osteolytic lesions produced by bone metastasis, bone pain due to bone metastasis, bone loss due to sex steroid hormone deficiency, bone abnormalities due to steroid hormone treatment, bone abnormalities caused by cancer therapeutics, osteomalacia, Bechet's disease, hyperostosis, metastatic bone disease, immobilization-induced osteopenia or osteoporosis, or glucocorticoid-induced osteopenia or osteoporosis, osteoporosis pseudoglioma syndrome, idiopathic juvenile osteoporosis, for the improvement of fracture healing after traumatic or atraumatic fracture, and for the maintenance or increase of energy level, for building up or strengthening muscle tissues and for weight gain, the method comprising administering to a subject in need thereof a therapeutic and/or prophylactic effective amount of a combination of one or more first components containing a strontium compound and one or more second components containing an alpha-ketoglutarate compound.

35. A method according to any of items 29-34, wherein the weight ratio between the total daily dose of strontium and the total daily dose of alpha-ketoglutarate is from about 0.01 to about 4, such as, e.g., from about 0.01 to about 4, from about 0.01 to about 2, from about 0.01 to about 1, from about 0.01 to about 0.6, from about 0.03 to about 4, from about 0.03 to about 2, from about 0.03 to about 1, from about 0.1 to about 2, from about 0.1 to about 1, from about 0.15 to about 0.5, from about 0.2 to about 2, from about 0.3 to about 2 or from about 0.4 to about 2.

36. A method according any of items 29-35, wherein the daily dose of strontium is at least about 0.01 g, such as, e.g. at least about 0.025 g, at least about 0.050 g, at least about 0.075 g, at least about 0.1 g, at least about 0.2 g, at least about 0.3 g, at least about 0.4 g or at least about 0.5 g or from about 0.01 g to about 2 g such as, e.g., from about 0.1 g to about 2 g, from about 0.3 g to about 2 g or from about 0.3 g to about 1 g.

37. A method according to any of items 29-36, wherein the daily dose of alpha-ketoglutarate is at least about 0.5 g, such as, e.g., at least about 1.0 g, at least about 1.5 g, at least about 2.0 g, at least about 2.5 g, at least about 3.0 g, at least about 4 g, at least about 5 g or from about 0.5 g to about 10 g, from about 0.5 g to 7 g, from about 2 g to about 10 g or from about 2 g to about 7 g.

38. A method according to any of items 29-37, wherein the strontium component and the alpha-ketoglutarate component are administered in the form of a pharmaceutical composition according to any of items 6-28.

39. A method according to any of items 29-38, wherein the administration takes place one or more times daily.

40. A method according to item 39, wherein the administration takes place from 2-5 times daily.

41. A method according to any of items 29-40, wherein the administration of the strontium component and the alpha-ketoglutarate component takes place simultaneously.

42. A method according to any of items 3240, wherein the administration of the strontium component and the alpha-ketoglutarate component takes place sequentially.

43. A method according to any of items 29-42, wherein the subject is a mammal, such as, e.g. a human or a domestic animal, such as, e.g., a cat, a dog, a horse, a cow or a sheep.

44. A method according to any of items 29-43 further comprising administering a daily dose of vitamin D.

45. A method according to item 44, wherein the vitamin D is vitamin $D_3$.

46. A method according to item 45, wherein the daily dose of vitamin $D_3$ is from about 5 µg to about 30 µg, such as, e.g., from about 10 µg to about 20 µg.

47. A method according to any of items 44-46, wherein the strontium component is administered in a dose corresponding to a daily dose of from about 0.3 g to about 1 g, the alpha-ketoglutarate component is administered in a dose corresponding to a daily dose of from about 2 g to about 7 g and the dose of vitamin $D_3$ corresponds to a daily dose of from about 10 µg to about 20 µg.

48. A method according to any of items 44-47, wherein the administration of the strontium component, the alpha-ketoglutarate component and vitamin D takes place simultaneously.

49. A method according to any of items 44-48, wherein the administration of the strontium component, the alpha-ketoglutarate component and/or vitamin D takes place sequentially.

50. A method according to any of item 29-49 further comprising administering a daily dose of calcium.

51. A method according to item 50, wherein the daily dose of calcium is from about 0.5 g to about 2 g such as, e.g., from about 0.5 g to about 1.5 g, from 0.5 g to 1 g and from about 1 g to about 1.5 g.

52. A method according to item 50 or 51, wherein the administration of the strontium component and calcium takes place simultaneously.
53. A method according to item 50 or 51, wherein the administration of the strontium component and calcium takes place sequentially.
54. A method according to any of items 50-53, wherein calcium is administered at least 0.5 h, such as, e.g., at least 1 h, at least 2 h, at least 3 h, at least 4 h, at least 5 h, at least 6 h, at least 7 h, at least 8 h, at least 9 h, at least 10 h, at least 11 h or at least 12 h after the administration of the strontium component.
55. A method according to any of items 50-53, wherein calcium is administered at least 0.5 h, such as, e.g., at least 1 h, at least 2 h, at least 3 h, at least 4 h, at least 5 h, at least 6 h, at least 7 h, at least 8 h, at least 9 h, at least 10 h, at least 11 h or at least 12 h before the administration of the strontium component.
56. A method according to any of items 50-54, wherein the strontium component and the alpha-ketoglutarate component are administered simultaneously and calcium are administered at least 1 h, such as, e.g., at least 2 h, at least 3 h, at least 4 h, at least 5 h, at least 6 h, at least 7 h, at least 8 h, at least 9 h, at least 10 h, at least 11 h or at least 12 h after the administration of the strontium and the alpha-ketoglutarate component.
57. A method according to any of items 50-53, 55 wherein the strontium component and the alpha-ketoglutarate component are administered simultaneously and calcium are administered at least 1 h, such as, e.g., at least 2 h, at least 3 h, at least 4 h, at least 5 h, at least 6 h, at least 7 h, at least 8 h, at least 9 h, at least 10 h, at least 11 h or at least 12 h before the administration of the strontium and the alpha-ketoglutarate component.
58. A method according to item 56 or 57, wherein the strontium component is administered in a dose corresponding to a daily dose of from about 0.3 g to about 1 g, the alpha-ketoglutarate component is administered in a dose corresponding to a daily dose of from about 2 g to about 7 g and the dose of calcium corresponds to a daily dose of from about 0.5 g to about 1 g.
59. A method according to any of items 44-58, wherein the strontium component is administered in a dose corresponding to a daily dose of from about 0.3 g to about 1 g, the alpha-ketoglutarate component is administered in a dose corresponding to a daily dose of from about 2 g to about 7 g, vitamin D3, if present, is administered in a daily dose of from about 10 μg to about 20 μg, and the dose of calcium corresponds to a daily dose of from about 0.5 g to about 1 g.
60. A method according to any of items 44-59, wherein the administration of the strontium component, the alpha-ketoglutarate component, vitamin D and calcium takes place simultaneously.
61. A method according to any of items 44-59, wherein the administration of the strontium component, the alpha-ketoglutarate component, vitamin D and/or calcium takes place sequentially.
62. A method according to any of items 44-59, wherein the strontium component, the alpha-ketoglutarate component and vitamin D are administered simultaneously and calcium are at least 1 h, such as, e.g., at least 2 h, at least 3 h, at least 4 h, at least 5 h, at least 6 h, at least 7 h, at least 8 h, at least 9 h, at least 10 h, at least 11 h or at least 12 h after the administration of the strontium and alpha-ketoglutarate component and vitamin D.
63. A method according to any of items 44-59, wherein the strontium component, the alpha-ketoglutarate component and vitamin D are administered simultaneously and calcium are administered at least 1 h, such as, e.g., at least 2 h, at least 3 h, at least 4 h, at least 5 h, at least 6 h, at least 7 h, at least 8 h, at least 9 h, at least 10 h, at least 11 h or at least 12 h before the administration of the strontium and alpha-ketoglutarate component and vitamin D.
64. A method according to any of items 29-63 further comprising administration of one or more further active substances, such as, e.g. glucagon-like peptide-2, glucagon-like peptide-2 releasing compositions, bisphosphonates, selective estrogen receptor modulators, calcitonin, parathyroid hormone, parathyroid hormone related peptide, glucosamine sulphate, glutamic acid and/or salts thereof, aspartate and/or salts thereof, proline, L-threonate, glucosamine sulphate, glutamine, asparagine and hydroxyproline.
65. A method according to item 64, wherein the further active substance is a parathyroid hormone or a fragment or analogue thereof or a parathyroid hormone related peptide or a fragment or analogue thereof.
66. A kit for use in treatment and/or prophylaxis of a cartilage and/or bone disease and/or conditions resulting in a dysregulation of cartilage and/or bone metabolism in a mammal, such as, e.g., a human female or male adult, adolescent or a child, such as, e.g., osteoporosis, osteoarthritis, osteopetrosis, osteopenia and Paget's disease, hypercalcemia of malignancy, periodontal disease, hyperparathyroidism, periarticular erosions in rheumatoid arthritis, osteodystrophy, myositis ossificans, Bechterew's disease, malignant hypercalcemia, osteolytic lesions produced by bone metastasis, bone pain due to bone metastasis, bone loss due to sex steroid hormone deficiency, bone abnormalities due to steroid hormone treatment, bone abnormalities caused by cancer therapeutics, osteomalacia, Bechet's disease, hyperostosis, metastatic bone disease, immobilization-induced osteopenia or osteoporosis, or glucocorticoid-induced osteopenia or osteoporosis, osteoporosis pseudoglioma syndrome, idiopathic juvenile osteoporosis, for the improvement of fracture healing after traumatic or atraumatic fracture, and for the maintenance or increase of energy level, for building up or strengthening muscle tissues and for weight gain, the kit comprising at least a first and a second component, the first component comprising strontium alpha-ketoglutarate and one or more second components comprising at least one of the following: i) a further strontium containing compound, ii) a further alpha-ketoglutarate containing compound, iii) a calcium containing compound, iv) vitamin D, v) parathyroid hormone, vi) a further active substance.
67. A kit for use in treatment and/or prophylaxis of a cartilage and/or bone disease and/or conditions resulting in a dysregulation of cartilage and/or bone metabolism in a mammal, such as, e.g., a human female or male adult, adolescent or a child, such as, e.g., osteoporosis, osteoarthritis, osteopetrosis, osteopenia and Paget's disease, hypercalcemia of malignancy, periodontal disease, hyperparathyroidism, periarticular erosions in rheumatoid arthritis, osteodystrophy, myositis ossificans, Bechterew's disease, malignant hypercalcemia, osteolytic lesions produced by bone metastasis, bone pain due to bone metastasis, bone loss due to sex steroid hormone deficiency, bone abnormalities due to steroid hormone treatment, bone abnormalities caused by cancer therapeutics, osteomalacia, Bechet's disease, hyperostosis, metastatic bone disease, immobilization-induced osteopenia or osteoporosis, or glucocorticoid-induced osteoporosis, osteoporosis pseudoglioma syndrome, idiopathic juvenile osteoporosis, for the improvement of fracture healing after traumatic or atraumatic fracture, and for the maintenance or increase of energy level, for building up or strengthening muscle tissues and for weight gain, the kit comprising at least a first and a second component, the first component comprising at least one of the following: i) strontium alpha-ketoglutarate, ii) a further strontium containing compound, iii) a further alpha-ketoglutarate containing compound, iv) a calcium containing compound, v) vitamin D, vi) parathyroid hormone, vii) a further active substance, and one or more second components comprising at least one of the following: i) strontium alpha-ketoglutarate, ii) a further strontium containing compound, iii) a further alpha-ketoglutarate containing compound, iv) a calcium containing compound, v) vitamin D, vi) parathyroid hormone, vii) a further active substance, with the proviso that the first and the one or more second components are not identical.

68. A kit according to item 66 or 67 further comprising instructions for use of the individual components.

69. Use of a strontium glutamate salt of the formula II

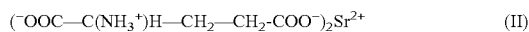

(II)

as a medicine.

70. Use of a salt according to item 69 for the preparation of a pharmaceutical composition for the treatment and/or prophylaxis of a cartilage and/or bone disease and/or conditions resulting in a dysregulation of cartilage and/or bone metabolism in a mammal, such as, e.g., a human female or male adult, adolescent or a child, such as, e.g., osteoporosis, osteoarthritis, osteopetrosis, osteopenia and Paget's disease, hypercalcemia of malignancy, periodontal disease, hyperparathyroidism, periarticular erosions in rheumatoid arthritis, osteodystrophy, myositis ossificans, Bechterew's disease, malignant hypercalcemia, osteolytic lesions produced by bone metastasis, bone pain due to bone metastasis, bone loss due to sex steroid hormone deficiency, bone abnormalities due to steroid hormone treatment, bone abnormalities caused by cancer therapeutics, osteomalacia, Bechet's disease, hyperostosis, metastatic bone disease, immobilization-induced osteopenia or osteoporosis, or glucocorticoid-induced osteopenia or osteoporosis, osteoporosis pseudoglioma syndrome, idiopathic juvenile osteoporosis, for the improvement of fracture healing after traumatic or atraumatic fracture, and for the maintenance or increase of energy level, for building up or strengthening muscle tissues and for weight gain.

71. Use of a salt according to item 69 or 70, wherein the pharmaceutical composition comprises an amount of the strontium glutamate salt, together with one or more physiologically acceptable excipients.

72. Use of a salt according to any of items 69-71, wherein the pharmaceutical composition further comprises an additional amount of a strontium-containing compound.

73. Use of a salt according to item 72, wherein the strontium-containing compound is selected from the group consisting of strontium salts of an organic or an inorganic acid.

74. Use of a salt according to item 73, wherein the inorganic acid is selected from the group consisting of hydrofluoric acid, hydrochloric acid, hydrobromic acid, hydroiodic acid, nitric acid, nitrous acid, phosphoric acid, phosphinic acid, phosphonic acid, sulfonic acid, sulfuric acid, sulfurous acid, disulfuric acid and boric acid.

75. Use of a salt according to item 73, wherein the organic acid is selected from the group consisting of acetic acid, $C_2H_5COOH$, $C_3H_7COOH$, $C_4H_9COOH$, $(COOH)_2$, $CH_2(COOH)_2$, $C_2H_4(COOH)_2$, $C_3H_6(COOH)_2$, $C_4H_9(COOH)_2$, $C_5H_{10}(COOH)_2$, fumaric acid, maleic acid, malonic acid, lactic acid, citric acid, tartaric acid, oxalic acid, ascorbic acid, benzoic acid, salicylic acid, phthalic acid, carbonic acid, formic acid, methanesulfonic acid, ethanesulfonic acid, benzenesulfonic acid, camphoric acid, gluconic acid, L-threonate, glucosamine sulphate, L-glutamic acid, D-glutamic acid, L-aspartic acid, D-aspartic acid, trifluoroacetic acid and ranelic acid.

76. Use of a salt according to any of items 73-75, wherein the acid is a non-chelator of strontium.

77. Use of a salt according to any of items 73-76, wherein the salt is in hydrate, anhydrous, solvate, polymorphous, amorphous, crystalline, microcrystalline or polymeric form.

78. Use of a salt according to any of items 73-77, wherein the salt is water soluble.

79. Use of a salt according to item 78, wherein the salt has a water solubility of at least 1 g/l, such as, e.g., at least 5 g/l, at least 10 g/l, at least 20 g/l, at least 30 g/l, at least 40 g/l, at least 50 g/l, at least 60 g/l, at least 70 g/l, at least 80 g/l, at least 90 g/l or at least 100 g/l measured at a temperature of 25° C.

80. Use of a salt according to any of items 73-79, wherein the salt is selected from the group comprising strontium chloride, strontium chloride hexahydrate, strontium citrate, strontium malonate, strontium succinate, strontium fumarate, strontium ascorbate, strontium L-glutamate, strontium D-glutamate, strontium L-aspartate, strontium D-aspartate, strontium pyruvate, strontium tartrate, strontium glutarate, strontium maleate, strontium methanesulfonate, strontium L-threonate, strontium benzenesulfonate and mixtures thereof.

81. Use of a salt according to any of items 73-80, wherein the acid is a monoprotic or a diprotic acid.

82. Use of a salt according to any of items 73-81, wherein the salt is selected from the group consisting of strontium bromide, strontium bromide hexahydrate, strontium acetate, strontium carbonate, strontium gluconate, strontium lactate, strontium ranelate and mixtures thereof.

83. Use of a salt according to any of items 69-82, further comprising an additional amount of a glutamate-containing compound.

84. Use of a salt according to item 83, wherein the glutamate-containing compound is a salt of an alkali metal or an alkaline earth metal, or mixtures thereof.

85. Use of a salt according to item 84, wherein the salt is selected from the group consisting of sodium glutamate, potassium glutamate, lithium glutamate, magnesium glutamate, calcium glutamate and mixtures thereof.

86. Use of a salt according to item 85, wherein the glutamate-containing compound is a salt of an amine or an amino acid or an ammonium salt or mixtures thereof.

87. Use of a salt according to item 86, wherein the amine is selected from methyl amine, ethyl amine, propyl amine, isopropyl amine and butyl amine.

88. Use of a salt according to item 86, wherein the amino acid is selected from arginine, ornithine, lysine and histidine.

89. Use of a salt according to any of items 69-88, wherein the composition further comprises one or more active substances.
90. Use of a salt according to item 89, wherein the one or more active substances has a therapeutic and/or prophylactic effect on a cartilage and/or bone disease and/or conditions resulting in a dysregulation of cartilage and/or bone metabolism in a mammal, such as, e.g., a human female or male adult, adolescent or a child, such as, e.g., osteoporosis, osteoarthritis, osteopetrosis, osteopenia and Paget's disease, hypercalcemia of malignancy, periodontal disease, hyperparathyroidism, periarticular erosions in rheumatoid arthritis, osteodystrophy, myositis ossificans, Bechterew's disease, malignant hypercalcemia, osteolytic lesions produced by bone metastasis, bone pain due to bone metastasis, bone loss due to sex steroid hormone deficiency, bone abnormalities due to steroid hormone treatment, bone abnormalities caused by cancer therapeutics, osteomalacia, Bechet's disease, hyperostosis, metastatic bone disease, immobilization-induced osteopenia or osteoporosis, or glucocorticoid-induced osteopenia or osteoporosis, osteoporosis pseudoglioma syndrome, idiopathic juvenile osteoporosis, for the improvement of fracture healing after traumatic or atraumatic fracture, and for the maintenance or increase of energy level, for building up or strengthening muscle tissues and for weight gain.
91. Use of a salt according to item 90, wherein the one or more active substances reduce the incidence of bone fracture, increase bone density and/or improve healing of bone such as, e.g., anti-resorptive and/or anabolic agents.
92. Use of a salt according to item 90 or 91, wherein the one or more active substances are selected from the group consisting of calcium-alpha-ketoglutarate, calcium, calcium salts, vitamin D, such as, e.g., vitamin D3 and/or functional equivalents of vitamin D3, glucagon-like peptide-2, glucagon-like peptide-2 releasing compositions, bisphosphonates, selective estrogen receptor modulators, calcitonin, parathyroid hormone, parathyroid hormone related peptide, glucosamine sulphate, glutamic acid and/or salts thereof, aspartate and/or salts thereof, proline, L-threonate, glucosamine sulphate, glutamine, asparagine and hydroxyproline.
93. A method for the treatment and/or prophylaxis of a cartilage and/or bone disease and/or conditions resulting in a dysregulation of cartilage and/or bone metabolism in a mammal, such as, e.g., a human female or male adult, adolescent or a child, such as, e.g., osteoarthritis, osteopetrosis, osteopenia and Paget's disease, hypercalcemia of malignancy, periodontal disease, hyperparathyroidism, periarticular erosions in rheumatoid arthritis, osteodystrophy, myositis ossificans, Bechterew's disease, malignant hypercalcemia, osteolytic lesions produced by bone metastasis, bone pain due to bone metastasis, bone loss due to sex steroid hormone deficiency, bone abnormalities due to steroid hormone treatment, bone abnormalities caused by cancer therapeutics, osteomalacia, Bechet's disease, hyperostosis, metastatic bone disease, immobilization-induced osteopenia or osteoporosis, or glucocorticoid-induced osteopenia or osteoporosis, osteoporosis pseudoglioma syndrome, idiopathic juvenile osteoporosis, for the improvement of fracture healing after traumatic or atraumatic fracture, and for the maintenance or increase of energy level, for building up or strengthening muscle tissues and for weight gain, the method comprising administering to a subject in need thereof an amount of a strontium glutamate salt.
94. A method according to item 93, wherein the salt is administered in a dose corresponding to from about 0.2 to about 28 g daily calculated as anhydrous salt.
95. A method according to item 93, wherein the salt is administered in a dose corresponding to from about 0.3 to about 25 g daily such as, e.g., from about 0.7 to about 20 g daily, from about 1 to about 17 g daily, from about 1.2 to about 16 g daily or from about 2 to about 6 g daily calculated as anhydrous salt.
96. A method according to any of items 93-95, further comprising administration of an additional dose of a strontium-containing compound.
97. A method according to any of items 93-96, further comprising administration of an additional dose of a glutamate-containing compound.
98. A method for the treatment and/or prophylaxis of a cartilage and/or bone disease and/or conditions resulting in a dysregulation of cartilage and/or bone metabolism in a mammal, such as, e.g., a human female or male adult, adolescent or a child, such as, e.g., osteoporosis, osteoarthritis, osteopetrosis, osteopenia and Paget's disease, hypercalcemia of malignancy, periodontal disease, hyperparathyroidism, periarticular erosions in rheumatoid arthritis, osteodystrophy, myositis ossificans, Bechterew's disease, malignant hypercalcemia, osteolytic lesions produced by bone metastasis, bone pain due to bone metastasis, bone loss due to sex steroid hormone deficiency, bone abnormalities due to steroid hormone treatment, bone abnormalities caused by cancer therapeutics, osteomalacia, Bechet's disease, hyperostosis, metastatic bone disease, immobilization-induced osteopenia or osteoporosis, or glucocorticoid-induced osteopenia or osteoporosis, osteoporosis pseudoglioma syndrome, idiopathic juvenile osteoporosis, for the improvement of fracture healing after traumatic or atraumatic fracture, and for the maintenance or increase of energy level, for building up or strengthening muscle tissues and for weight gain, the method comprising administering to a subject in need thereof a therapeutic and/or prophylactic effective amount of a combination of one or more first components containing a strontium compound and one or more second components containing a glutamate compound.
99. A method according to any of items 93-98, wherein the weight ratio between the total daily dose of strontium and the total daily dose of glutamate is from about 0.01 to about 4, such as, e.g., from about 0.01 to about 4, from about 0.01 to about 2, from about 0.01 to about 1, from about 0.01 to about 0.6, from about 0.03 to about 4, from about 0.03 to about 2, from about 0.03 to about 1, from about 0.1 to about 2, from about 0.1 to about 1, from about 0.15 to about 0.5, from about 0.2 to about 2, from about 0.3 to about 2 or from about 0.4 to about 2.
100. A method according to any of items 93-99, wherein the daily dose of strontium is at least about 0.01 g, such as, e.g. at least about 0.025 g, at least about 0.050 g, at least about 0.075 g, at least about 0.1 g, at least about 0.2 g, at least about 0.3 g, at least about 0.4 g or at least about 0.5 g or from about 0.01 to about 2 g such as, e.g., from about 0.1 to about 2 g, from about 0.3 to about 2 g or from about 0.3 to about 1 g.
101. A method according to any of items 93-100, wherein the daily dose of glutamate is at least about 0.5 g, such as, e.g., at least about 1.0 g, at least about 1.5 g, at least about 2.0 g, at least about 2.5 g, at least about 3.0 g, at least about 4 g, at least about 5 g or from about 0.5 to about 10 g, from about 0.5 to 7 g, from about 2 to about 10 g or from about 2 to about 7 g.

102. A method according to any of items 93-100, wherein the strontium component and the glutamate component are administered in the form of a pharmaceutical composition.

103. A method according to any of items 93-101, wherein the administration takes place one or more times daily.

104. A method according to item 103, wherein the administration takes place from 2 to 5 times daily.

105. A method according to any of items 93-104, wherein the administration of the strontium component and the glutamate component takes place simultaneously.

106. A method according to any of items 96-104, wherein the administration of the strontium component and the glutamate component takes place sequentially.

107. A method according to any of items 96-106, wherein the subject is a mammal, such as, e.g. a human or a domestic animal, such as, e.g., a cat, a dog, a horse, a cow or a sheep.

108. A method according to any of items 93-107 further comprising administering a daily dose of vitamin D.

109. A method according to item 108, wherein the vitamin D is vitamin D3.

110. A method according to item 109, wherein the daily dose of vitamin D3 is from about 5 µg to about 30 µg, such as, e.g., from about 10 µg to about 20 µg.

111. A method according to any of items 108-110, wherein the daily dose of strontium is from about 0.3 g to about 1 g, the daily dose of glutamate is from about 2 g to about 7 g and the daily dose of vitamin D3 is from about 10 µg to about 20 µg.

112. A method according to any of items 108-110, wherein the administration of strontium, glutamate and vitamin D takes place simultaneously.

113. A method according to any of items 108-110, wherein the administration of strontium, glutamate and/or vitamin D takes place sequentially.

114. A method according to any of item 93-113 further comprising administering a daily dose of calcium.

115. A method according to item 114, wherein the daily dose of calcium is from about 0.5 to about 2 g such as, e.g., from about 0.5 to about 1.5 g, from about 0.5 to about 1 g, or from about 1 g to about 1.5 g.

116. A method according to item 114 or 115, wherein the administration of the strontium component and calcium takes place simultaneously.

117. A method according to item 114 or 115, wherein the administration of the strontium component and calcium takes place sequentially.

118. A method according to any of items 114-117, wherein calcium is administered at least 0.5 h, such as, e.g., at least 1 h, at least 2 h, at least 3 h, at least 4 h, at least 5 h, at least 6 h, at least 7 h, at least 8 h, at least 9 h, at least 10 h, at least 11 h or at least 12 h after the administration of the strontium component.

119. A method according to any of items 114-117, wherein calcium is administered at least 0.5 h, such as, e.g., at least 1 h, at least 2 h, at least 3 h, at least 4 h, at least 5 h, at least 6 h, at least 7 h, at least 8 h, at least 9 h, at least 10 h, at least 11 h or at least 12 h before the administration of the strontium component.

120. A method according to any of items 114-118, wherein strontium and glutamate are administered simultaneously and calcium are administered at least 1 h, such as, e.g., at least 2 h, at least 3 h, at least 4 h, at least 5 h, at least 6 h, at least 7 h, at least 8 h, at least 9 h, at least 10 h, at least 11 h or at least 12 h after the administration of strontium and glutamate.

121. A method according to any of items 114-117, 119 wherein strontium and glutamate are administered simultaneously and calcium are administered at least 1 h, such as, e.g., at least 2 h, at least 3 h, at least 4 h, at least 5 h, at least 6 h, at least 7 h, at least 8 h, at least 9 h, at least 10 h, at least 11 h or at least 12 h before the administration of strontium and glutamate.

122. A method according to item 120 or 121, wherein strontium is administered in a dose corresponding to a daily dose of from about 0.3 to about 1 g, glutamate is administered in a dose corresponding to a daily dose of from about 2 to about 7 g and the dose of calcium corresponds to a daily dose of from about 0.5 to 1 g.

123. A method according to any of items 108-122, wherein strontium is administered in a dose corresponding to a daily dose of from about 0.3 g to about 1 g, glutamate is administered in a dose corresponding to a daily dose of from about 2 g to about 7 g, vitamin D3, if present, is administered in a daily dose of from about 10 µg to about 20 µg, and the dose of calcium corresponds to a daily dose of from about 0.5 g to about 1 g.

124. A method according to any of items 108-123, wherein the administration of strontium, glutamate, vitamin D and calcium takes place simultaneously.

125. A method according to any of items 108-123, wherein the administration of strontium, glutamate, vitamin D and/or calcium takes place sequentially.

126. A method according to any of items 108-123, wherein strontium, glutamate and vitamin D are administered simultaneously and calcium are administered at least 1 h, such as, e.g., at least 2 h, at least 3 h, at least 4 h, at least 5 h, at least 6 h, at least 7 h, at least 8 h, at least 9 h, at least 10 h, at least 11 h or at least 12 h after the administration of strontium and glutamate and vitamin D.

127. A method according to any of items 108-123, wherein strontium, glutamate and vitamin D are administered simultaneously and calcium are administered at least 1 h, such as, e.g., at least 2 h, at least 3 h, at least 4 h, at least 5 h, at least 6 h, at least 7 h, at least 8 h, at least 9 h, at least 10 h, at least 11 h or at least 12 h before the administration of strontium, glutamate and vitamin D.

128. A method according to any of items 93-126 further comprising administration of a further active substance, such as, e.g. glucagon-like peptide-2, glucagon-like peptide-2 releasing compositions, bisphosphonates, selective estrogen receptor modulators, calcitonin, parathyroid hormone, parathyroid hormone related peptide, glutamic acid and/or salts thereof, proline, L-threonate, glucosamine sulphate, glutamine and hydroxyproline.

129. A method according to item 128, wherein the further active substance is a parathyroid hormone or a fragment or analogue thereof or a parathyroid hormone related peptide or a fragment or analogue thereof.

130. A kit for use in treatment and/or prophylaxis of a cartilage and/or bone disease and/or conditions resulting in a dysregulation of cartilage and/or bone metabolism in a mammal, such as, e.g., a human female or male adult, adolescent or a child, such as, e.g., osteoarthritis, osteopetrosis, osteopenia and Paget's disease, hypercalcemia of malignancy, periodontal disease, hyperparathyroidism, periarticular erosions in rheumatoid arthritis, osteodystrophy, myositis ossificans, Bechterew's disease, malignant hypercalcemia, osteolytic lesions produced by bone metastasis, bone pain due to bone metastasis, bone loss due to sex steroid hormone deficiency, bone abnormalities due to steroid hormone treatment, bone abnormalities caused by cancer therapeutics, osteomalacia, Bechet's disease, hyperostosis, metastatic bone disease, immobilization-induced osteopenia or osteoporosis, or glucocorticoid-induced osteopenia or osteoporosis, osteoporosis pseudoglioma syndrome, idiopathic juvenile osteoporosis, for the improvement of fracture healing after traumatic or atraumatic fracture, and for the maintenance or increase of energy level, for building up or strengthening muscle tissues and for weight gain, the kit comprising at least a first and a second component, the first component comprising strontium glutamate and one or more second components comprising at least one of the following: i) a further strontium containing compound, ii) a further glutamate containing compound, iii) a calcium containing compound, iv) vitamin D, v) parathyroid hormone, vi) a further active substance.

131. A kit for use in treatment and/or prophylaxis of a cartilage and/or bone disease and/or conditions resulting in a dysregulation of cartilage and/or bone metabolism in a mammal, such as, e.g., a human female or male adult, adolescent or a child, such as, e.g., osteoporosis, osteoarthritis, osteopetrosis, osteopenia and Paget's disease, hypercalcemia of malignancy, periodontal disease, hyperparathyroidism, periarticular erosions in rheumatoid arthritis, osteodystrophy, myositis ossificans, Bechterew's disease, malignant hypercalcemia, osteolytic lesions produced by bone metastasis, bone pain due to bone metastasis, bone loss due to sex steroid hormone deficiency, bone abnormalities due to steroid hormone treatment, bone abnormalities caused by cancer therapeutics, osteomalacia, Bechet's disease, hyperostosis, metastatic bone disease, immobilization-induced osteopenia or osteoporosis, or glucocorticoid-induced osteopenia or osteoporosis, osteoporosis pseudoglioma syndrome, idiopathic juvenile osteoporosis, for the improvement of fracture healing after traumatic or atraumatic fracture, and for the maintenance or increase of energy level, for building up or strengthening muscle tissues and for weight gain, the kit comprising at least a first and a second component, the first component comprising at least one of the following: i) strontium alpha-ketoglutarate, ii) a further strontium containing compound, iii) a further alpha-ketoglutarate containing compound, iv) a calcium containing compound, v) vitamin D, vi) parathyroid hormone, vii) a further active substance, and one or more second components comprising at least one of the following: i) strontium glutamate, ii) a further strontium containing compound, iii) a further glutamate containing compound, iv) a calcium containing compound, v) vitamin D, vi) parathyroid hormone, vii) a further active substance, with the proviso that the first and the one or more second components are not identical.

132. A kit according to item 130 or 131 further comprising instructions for use of the individual components.

133. A pharmaceutical composition according to any of items 6-28 in the form of a tablet.

134. A pharmaceutical composition according to item 133, wherein the tablet is coated with a coating that enables release of at least part of the salt in the proximal part of the small intestine, such as e.g. the duodenum and/or the proximal jejunum such as at least 50% w/w, at least 60% w/w, at least 65% w/w, at least 70% w/w, at least 80% w/w or at least 90% w/w of the total amount of the salt contained in the tablet.

135. A pharmaceutical composition according to item 133 or 134, wherein the tablet has a shape that makes it easy and convenient for a patient to swallow.

136. A pharmaceutical composition according to item 135, wherein the tablet has a rounded or a rod-like shape, without any sharp edges.

137. A pharmaceutical composition according to any of items 133-136, wherein the tablet is designed to be divided in two or more parts.

DETAILED DESCRIPTION OF THE INVENTION

Figure 1:
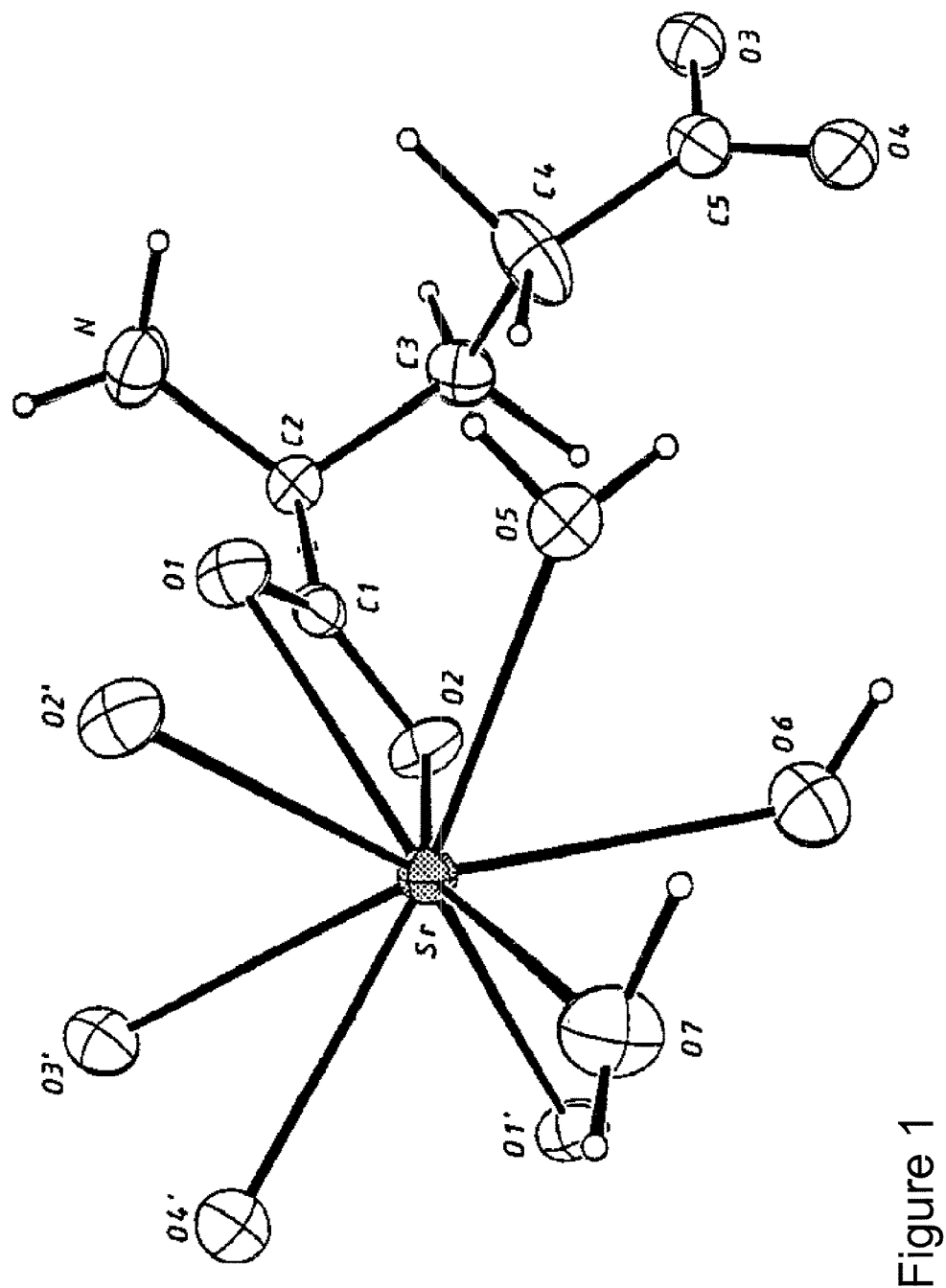
FIG. 1 is a depiction of the molecular structure of strontium L-glutamate ($6*H_2O$) in the crystalline form as disclosed by Schmidbaur et al 1989. The crystal is shown with atoms depicted as ellipsoids (defined at the 50% probability level according to the ORTEP program (Oak Ridge Thermal Ellipsoid Plot Program)). Complexation by $Sr^{2+}$ by three additional symmetrically related amino acids is indicated only by the coordinating carboxy oxygen atoms O1, O2 and O3/O4.

Previous studies have shown that various strontium compounds modulate bone loss in osteoporosis when present at levels higher than those required for normal cell physiology. The effect is believed to be due to a stimulatory effect of strontium on pre-osteoblastic cell differentiation and migration, and a direct or matrix-mediated inhibition of osteoclast activity by strontium (Reginster, J Y, *Curr pharm Des* 2002:8 (21):1907-16). In other words, strontium both works as an anti-resorptive and an anabolic agent. Various salts of strontium are known from the prior art, such as, e.g., strontium ranelate (distrontium salt of 2-[N,N-di(carboxymethyl) amino]-3-cyano-4-carboxymethylthiophene-5-carboxylic acid) described in EP-B 0 415 850. The ranelate part of the strontium compound, derived from ranelic acid, is unlikely to have any therapeutic effect towards cartilage or bone conditions per se. Other known strontium salts are e.g., strontium tartrate, strontium phosphate, strontium carbonate, strontium nitrate, strontium sulfate and strontium chloride.

The naturally occurring salts of strontium, such as the carbonate and sulphate salts, have very low water solubility (0.15 g/l or below at room temperature). In contrast, the other strontium salts, such as strontium chloride, strontium hydroxide, strontium nitrate, strontium oxide and strontium acetate have very high solubilities in the range from 225-800 g/l in water. In this respect the strontium salts are very similar to the corresponding magnesium and calcium salts.

Organic strontium salts have been described, but literature reports of this type of compounds are limited to rather few substance. Again in these cases the physiochemical properties have been reported to be very similar to the corresponding magnesium, calcium and barium salts. Carboxylic acids can form stable crystalline salts with divalent earth metals such as strontium, and especially di-carboxylic acids are interesting, as they can have a partial chelating effect. Such complexation may be important in biological systems, where the alkaline earth metals, especially calcium and magnesium, plays important physiological roles (see the following sections). Hence the divalent metal ions may exist in a complex form in the aqueous environment in biological systems, rather than in a free and un-bound ionic form. Complex formation constants with the alkaline earth metals in aqueous solution are higher for amino acids than for hydroxy-carboxylic acids and the related non-carboxylic acids, which suggest that the amino group may play a role in the complex formation. Generally the differences in association constants for the various ligands becomes smaller as the radius of the metal increases, and thus stability of strontium complexes with di-carboxylic acid is lower than the stability of the comparable complexes with calcium and magnesium.

For a pharmaceutical application of the strontium salts this is very important as it means that strontium salts of dicarboxylic amino acids may be particularly useful. We have found that such salts, such as strontium glutamate and strontium aspartate is more soluble than other dicarboxylic strontium salts of similar molecular size. In pure aqueous solutions of such salts strontium exists in partly complexed form. However, when administered to an animal such as a mammal, i.e. a rat, dog, monkey or human, ionic strontium as well as strontium complexed to the carboxylic acid anion will be taken up from the intestinal lumen by both passive and active transport mechanisms. In this case strontium will be displaced from the complexes by available calcium and magnesium which forms much more stable complexes with the ionized amino acids. It appears that with the heavy group II metals, such as strontium, the amino group in both aspartate and glutamate is much less significant for metal complexation, probably due to the unfavourable chelation of large metals in five- or six-membered rings. Accordingly, dianionic amino-acid salts of strontium, such as strontium aspartate and strontium glutamate may be especially suited for prophylactic and/or therapeutic interventions in bone disease as the amino-acids may act to preferentially bind/complex with available free calcium, thus promoting both the intestinal uptake of the calcium ion, and physiological action of the ion, in particular its role in regulation of bone turnover.

However, the present invention is not limited to the above-mentioned specific examples of suitable salts, but merely to the general applicability of water-soluble salt of strontium. As appears from the above, the known strontium salt that are water-soluble have a water-solubility of at least about 225-800 g/l and the other known strontium salts have solubilities that are very low (below 0.1 g/l at room temperature). The exemplified amino acids salts of strontium that are exemplified herein and that have suitable in vivo properties have a water solubility of 1 g/l or more and not more than about 100 g/l at room temperature. Accordingly, the invention relates to strontium salts that have a water-solubility from about 1 g/l to about 100 g/l at room temperature.

As it appears from the above, the present invention relates to novel strontium salts and pharmaceutical compositions containing them for use in the treatment and/or prophylaxis of cartilage and/or bone conditions and for methods of treating such conditions. One of the strontium salts has been described before, namely the strontium glutamate. However, the present inventors have found an improved method for the preparation of this salt and the method is also an object of the invention. Furthermore, the invention relates to the therapeutic, prophylactic and/or diagnostic use of the strontium salt having a water-solubility in a range of from about 1 g/l to about 100 g/l.

For the treatment and/or prophylaxis of a cartilage and/or bone disease and/or conditions resulting in a dysregulation of cartilage and/or bone metabolism in a mammal, such as, e.g., a human female or male adult, adolescent or a child, such as, e.g., osteoporosis, osteoarthritis, osteopetrosis, osteopenia and Paget's disease, hypercalcemia of malignancy, periodontal disease, hyperparathyroidism, periarticular erosions in rheumatoid arthritis, osteodystrophy, myositis ossificans, Bechterew's disease, malignant hypercalcemia, osteolytic lesions produced by bone metastasis, bone pain due to bone metastasis, bone loss due to sex steroid hormone deficiency, bone abnormalities due to steroid hormone treatment, bone abnormalities caused by cancer therapeutics, osteomalacia, Bechet's disease, hyperostosis, metastatic bone disease, immobilization-induced osteopenia or osteoporosis, or glucocorticoid-induced osteopenia or osteoporosis, osteoporosis pseudoglioma syndrome, idiopathic juvenile osteoporosis, for the improvement of fracture healing after traumatic or atraumatic fracture, and for the maintenance or increase of energy level, for building up or strengthening muscle tissues and for weight gain, the present inventors have found that the use of a strontium salt has prophylactic and/or therapeutic value in that one or more of the following beneficial effects can be obtained:
  i) an improved bioavailability of strontium,
  ii) an improved absorption of strontium,
  iii) a reduction of side effects,
  iv) a flexible dose adjustment of strontium in order to tailor prevention and/or treatment of a specific disease stage,
  v) a possible reduction in daily dosage
  vi) a possible reduction of the number of different pharmaceutical compositions that a patient must use to achieve a therapeutic effect.

Suitable strontium salts for use according to the invention or for use in admixture with a strontium salt according to the invention are found in the following list. However, only those salts that have a water-solubility of at least about 1 g/l and at the most about 100 g/l are object of the present invention. Such strontium salts are e.g. the amino acid salts strontium glutamate and strontium aspartate; strontium malonate; strontium pyruvate, strontium alpha-ketoglutarate, strontium maleate and strontium succinate.

The inorganic acid for making strontium salts may be selected from the group consisting of boric acid, bromous acid, chloric acid, diphosphoric acid, disulfuric acid, dithionic acid, dithionous acid, fulminic acid, hydrazoic acid, hydrobromic acid, hydrofluoric acid, hydroiodic acid, hydrogen sulfide, hypophosphoric acid, hypophosphorous acid, iodic acid, iodous acid, metaboric acid, metaphosphoric acid, metaphosphorous acid, metasilicic acid, nitrous acid, orthophosphoric acid, orthophosphorous acid, orthosilicic acid, phosphoric acid, phosphinic acid, phosphonic acid, pyrophosphorous acid, selenic acid, sulfonic acid, thiocyanic acid and thiosulfuric acid.

The organic acid may be selected from the group consisting of $C_2H_5COOH$, $C_3H_7COOH$, $C_4H_9COOH$, $(COOH)_2$, $CH_2(COOH)_2$, $C_2H_4(COOH)_2$, $C_3H_6(COOH)_2$, $C_4H_8(COOH)_2$, $C_5H_{10}(COOH)_2$, fumaric acid, maleic acid, malonic acid, lactic acid, citric acid, tartaric acid, oxalic acid, ascorbic acid, benzoic acid, salicylic acid, pyruvic acid, L- and D-aspartic acid, phthalic acid, carbonic acid, formic acid, methanesulfonic acid, ethanesulfonic acid, camphoric acid, gluconic acid, L- and D-glutamic acid, trifluoroacetic acid, ranelic acid, 2,3,5,6-tetrabromobenzoic acid, 2,3,5,6-tetrachlorobenzoic acid, 2,3,6-tribromobenzoic acid, 2,3,6-trichlorobenzoic acid, 2,4-dichlorobenzoic acid, 2,4-dihydroxybenzoic acid, 2,6-dinitrobenzoic acid, 3,4-dimethoxybenzoic acid, abietic acid, acetoacetic acid, acetonedicarboxylic acid, aconitic acid, acrylic acid, adipic acid, alpha-ketoglutamic acid, anthranilic acid, benzilic acid, arachidic acid, azelaic acid, behenic acid, benzenesulfonic acid, beta-hydroxybutyric acid, brassidic acid, capric acid, chloroacrylic acid, cinnamic acid, citraconic acid, crotonic acid, cyclopentane-1,2-dicarboxylic acid, cyclopentanecarboxylic acid, cystathionine, decanoic acid, erucic acid, ethylenediaminetetraacetic acid, fulvic acid, fumaric acid, gallic acid, glutaconic acid, glutamic acid, gulonic acid, heptanoic acid, hexanoic acid, humic acid, hydroxystearic acid, isophthalic acid, itaconic acid, lanthionine, lauric acid (dodecanoic acid), levulinic acid, linoleic acid (cis,cis-9,12-octadecadienoic acid), malic acid, m-chlorobenzoic acid, melissic acid, mesaconic acid, methacrylic acid, monochloroacetic acid, myristic acid, (tetradecanoic acid), nonanoic acid, norvaline, octanoic acid, oleic acid (cis-9-octadecenoic acid), ornithine, oxaloacetic acid, palmitic acid (hexadecanoic acid), p-aminobenzoic acid, p-chlorobenzoic acid, petroselic acid, phenylacetic acid, p-hydroxybenzoic acid, pimelic acid, propiolic acid, propionic acid, p-tert-butylbenzoic acid, p-toluenesulfonic acid, pyruvic acid, sarcosine, sebacic acid, serine, sorbic acid, stearic acid (octadecanoic acid), suberic acid, succinic acid, terephthalic acid, tetrolic acid, threonine, thyronine, tricarballylic acid, trichloroacetic acid, trimellitic acid, trimesic acid, tyrosine, ulmic acid and cyclohexanecarboxylic acid.

All acids, which FDA has regarded as safe for use in compositions for oral intake, may be used in the present invention. Examples of suitable acids are mentioned in the following Table 1:

TABLE 1

Acids for making strontium salts

N-ACETYL-L-METHIONINE
ACONITIC ACID
ACRYLIC ACID-2-ACRYLAMIDO-2-METHYL PROPANE SULFONIC ACID COPOLYMER
ADIPIC ACID
ALGINIC ACID
P-AMINOBENZOIC ACID
ANISIC ACID
ASCORBIC ACID
L-ASPARTIC ACID
D-ASPARTIC ACID
BENZOIC ACID
BORIC ACID
BUTTER ACIDS
BUTYRIC ACID
CHOLIC ACID
CINNAMIC ACID
CITRIC ACID
CYCLOHEXANEACETIC ACID
CYCLOHEXANECARBOXYLIC ACID
DECANOIC ACID
4-DECENOIC ACID
5-DECENOIC ACID
6-DECENOIC ACID
9-DECENOIC ACID
DEHYDROACETIC ACID
DESOXYCHOLIC ACID
2,4-DIHYDROXYBENZOIC ACID
3,7-DIMETHYL-6-OCTENOIC ACID
2,4-DIMETHYL-2-PENTENOIC ACID
(E)-2-DECENOIC ACID
EDTA, CALCIUM DISODIUM
(E)-2-HEPTENOIC ACID
(E)-2-NONENOIC ACID
(E)-2-OCTENOIC ACID
ERYTHORBIC ACID
ETHANESULFONIC ACID, 2-(1-(DIFLUORO-((TRIFLUOROETHENYL)O
2-ETHYLBUTYRIC ACID
4-ETHYLOCTANOIC ACID
FATTY ACIDS
FOLIC ACID
FORMIC ACID
FUMARIC ACID
D-GLUCONIC ACID
L-GLUTAMIC ACID
D-GLUTAMIC ACID
GLUCOSAMINE SULPHATE
GLYCOCHOLIC ACID
HEPTANOIC ACID
HEXANOIC ACID
TRANS-2-HEXENOIC ACID
3-HEXENOIC ACID
HYDROCHLORIC ACID
4-HYDROXYBENZOIC ACID
1-HYDROXYETHYLIDENE-1,1-DIPHOSPHONIC ACID
3-HYDROXY-2-OXOPROPIONIC ACID
ISOBUTYRIC ACID
ISOVALERIC ACID
ALPHA-KETOBUTYRIC ACID
LACTIC ACID
LAURIC ACID
LEVULINIC ACID
LIGNOSULFONIC ACID

TABLE 1-continued

Acids for making strontium salts

LINOLEIC ACID
L-MALIC ACID
MALIC ACID
2-MERCAPTOPROPIONIC ACID
METHACRYLIC ACID-DIVINYLBENZENE COPOLYMER
2-METHOXYBENZOIC ACID
3-METHOXYBENZOIC ACID
4-METHOXYBENZOIC ACID
TRANS-2-METHYL-2-BUTENOIC ACID
2-METHYLBUTYRIC ACID
3-METHYLCROTONIC ACID
2-METHYLHEPTANOIC ACID
2-METHYLHEXANOIC ACID
5-METHYLHEXANOIC ACID
4-METHYLNONANOIC ACID
4-METHYLOCTANOIC ACID
3-METHYL-2-OXOBUTANOIC ACID
3-METHYL-2-OXOPENTANOIC ACID
4-METHYL-2-OXOPENTANOIC ACID
3-METHYLPENTANOIC ACID
4-METHYLPENTANOIC ACID
2-METHYL-2-PENTENOIC ACID
2-METHYL-3-PENTENOIC ACID
2-METHYL-4-PENTENOIC ACID
4-(METHYLTHIO)-2-OXOBUTANOIC ACID
2-METHYLVALERIC ACID
MONOCHLOROACETIC ACID--PROHIBITED
MYRISTIC ACID
NONANOIC ACID
NORDIHYDROGUAIARETIC ACID--PROHIBITED
9,12-OCTADECADIENOIC ACID (48%) AND 9,12,15-OCTADECATRIENOIC ACID
OCTANOIC ACID
OLEIC ACID
OLEIC ACID, FROM TALL OIL FATTY ACIDS
2-OXOPENTANEDIOIC ACID
2-OXO-3-PHENYLPROPIONIC ACID
PALMITIC ACID
4-PENTENOIC ACID
PERACETIC ACID
PERIODIC ACID
PHENOXYACETIC ACID
PHENYLACETIC ACID
3-PHENYLPROPIONIC ACID
PHOSPHORIC ACID
POLYMALEIC ACID
PROPIONIC ACID
PYROLIGNEOUS ACID
PYROLIGNEOUS ACID, EXTRACT
PYRUVIC ACID
SALICYLIC ACID
SORBIC ACID
STEARIC ACID
SUCCINIC ACID
SULFURIC ACID
SULFUROUS ACID
TANNIC ACID
TARTARIC ACID, L
TAUROCHOLIC ACID
1,2,5,6-TETRAHYDROCUMINIC ACID
THIODIPROPIONIC ACID
L-THREONIC ACID
TRIFLUOROMETHANE SULFONIC ACID
UNDECANOIC ACID
10-UNDECENOIC ACID
N-UNDECYLBENZENESULFONIC ACID
VALERIC ACID
VANILLIC ACID

In one embodiment of the invention, the acid may be a non-chelator of strontium. In yet a further embodiment, the acid may be a monoprotic or a diprotic acid.

The strontium salt for use according to the invention is water soluble, having a water solubility of at least 1 g/l, such as, e.g., at least 5 g/l, at least 10 g/l, at least 20 g/l, at least 30 g/l, at least 40 g/l, at least 50 g/l, at least 60 g/l, at least 70 g/l, at least 80 g/l, at least 90 g/l or about 100 g/l measured at room temperature, i.e a temperature of 20-25° C.

Specific examples of strontium salts for use according to the invention are strontium malonate, strontium succinate, strontium fumarate, strontium ascorbate, strontium aspartate in either L and/or D-form, strontium glutamate in either L- and/or D-form, strontium pyruvate, strontium tartrate, strontium glutarate, strontium maleate, strontium methanesulfonate, strontium benzenesulfonate and mixtures thereof.

Strontium L-glutamate (hexahydrate) has previously been prepared by reacting strontium hydroxide with L-glutamic acid under reflux for 3 hours with a subsequent cooling and slow crystallization over a period of 2 weeks. The crystals were subjected to X-ray crystallography in order to elucidate the crystal structure (please see: H. Schmidbaur, I. Bach, L. Wilkinson & G. Müller (1989), Chem Ber. 122; 1433-1438). The investigations were related to a crystalline form of the strontium salts with the properties described in FIGS. 1 and 2 and Tables 2 and 3.

TABLE 2

Distances [Å] and angles [°] for strontium L-glutamate hexahydrate as described by Schmidbaur et al 1989. For atomic numbering please see FIG. 1. For preparing symmetry operations O1' was derived from O1 by the operation: 0.5 + X, 0.5 − X, −Z; O2' was derived from O2 by the operations X − 0.5, 0.5 − Y, −Z; and O3' and O4' was derived from O3 and O4 respectively by the operation X, Y − 1, Z. The parenthesis indicates the estimated units of the last significant figure.

| Distances | | | |
|---|---|---|---|
| Sr—O1 | 2.724(2) | Sr—O2 | 2.665(2) |
| Sr—O1' | 2.642(2) | Sr—O2' | 2.651(2) |
| Sr—O3' | 2.677(2) | Sr—O4' | 2.658(2) |
| Sr—O5 | 2.658(2) | Sr—O6 | 2.708(2) |
| Sr—O7 | 2.640(2) | O1—C1 | 1.268(3) |
| O2—C1 | 1.258(3) | C1—C2 | 1.521(3) |
| C2—N | 1.469(3) | C2—C3 | 1.526(3) |
| C3—C4 | 1.524(4) | C4—C5 | 1.513(4) |
| C5—O3 | 1.264(3) | C5—O4 | 1.264(3) |

| Angles | | | |
|---|---|---|---|
| O1—Sr—O1' | 115.4(1) | O1—Sr—O2 | 48.4(1) |
| O1—Sr—O2' | 67.8(1) | O1—Sr—O3' | 75.4(1) |
| O1—Sr—O4' | 120.8(1) | O1—Sr—O5 | 74.8(1) |
| O1—Sr—O6 | 105.7(1) | O1—Sr—O7 | 146.5(1) |
| O2—Sr—O1' | 68.8(1) | O2—Sr—O2' | 115.3(1) |
| O2—Sr—O3' | 79.3(1) | O2—Sr—O4' | 122.1(1) |
| O2—Sr—O5 | 98.4(1) | O2—Sr—O6 | 76.8(1) |
| O2—Sr—O7 | 154.8(1) | O2'—Sr—O1' | 153.8(1) |
| O2'—Sr—O3' | 75.5(1) | O2'—Sr—O4' | 78.9(1) |
| O2'—Sr—O5 | 70.9(1) | O2'—Sr—O6 | 138.1(1) |
| O2'—Sr—O7 | 86.7(1) | O3'—Sr—O1' | 80.4(1) |
| O3'—Sr—O4' | 48.8(1) | O3'—Sr—O5 | 141.3(1) |
| O3'—Sr—O6 | 145.3(1) | O3'—Sr—O7 | 120.2(1) |
| O4'—Sr—O1' | 77.7(1) | O4'—Sr—O5 | 137.2(1) |
| O4'—Sr—O6 | 130.7(1) | O4'—Sr—O7 | 72.0(1) |
| O1'—Sr—O5 | 135.2(1) | O1'—Sr—O6 | 67.7(1) |
| O1'—Sr—O7 | 97.1(1) | O7—Sr—O5 | 76.5(1) |
| O7—Sr—O6 | 78.5(1) | O6—Sr—O5 | 67.6(1) |
| O1—C1—O2 | 122.1(2) | O1—C1—C2 | 119.7(3) |
| O2—C1—C2 | 118.2(3) | C1—C2—N | 114.5(2) |
| N—C2—C3 | 111.1(2) | C1—C2—C3 | 109.9(2) |
| C2—C3—C4 | 114.5(2) | C3—C4—C5 | 114.1(3) |
| C4—C5—O3 | 119.7(2) | C4—C5—O4 | 118.7(2) |
| O3—C5—O4 | 121.5(2) | | |

TABLE 3

Fractional atomic coordinates and equivalent isotropic thermal parameters for strontium L-glutamate hexahydrate as described by Schmidbaur et al 1989.
$U_{eq} = (U_1 * U_2 * U_3)$, where $U_1$, $U_2$ and $U_3$ are the intrinsic values of the $U_{ij}$ matrix.
For atom nomenclature please refer to FIG. 1.

| Atom | X/A | Y/B | Z/C | U(eq.) |
|---|---|---|---|---|
| Sr | 0.9078 | 0.1999 | 0.0562 | 0.016 |
| O1 | 0.7595 | 0.3566 | −0.0465 | 0.023 |
| O2 | 1.0591 | 0.3655 | −0.0393 | 0.022 |
| C1 | 0.9123 | 0.4069 | −0.0655 | 0.017 |
| C2 | 0.9206 | 0.5254 | −0.1202 | 0.019 |
| N | 0.7562 | 0.5338 | −0.1612 | 0.031 |
| C3 | 0.9679 | 0.6810 | −0.0913 | 0.024 |
| C4 | 0.8471 | 0.7306 | −0.0342 | 0.033 |
| C5 | 0.8953 | 0.8849 | −0.0059 | 0.021 |
| O3 | 0.9030 | 0.9998 | −0.0434 | 0.024 |
| O4 | 0.9172 | 0.8970 | 0.0557 | 0.026 |
| O5 | 0.7071 | 0.4172 | 0.1114 | 0.029 |
| O6 | 1.1116 | 0.4051 | 0.1232 | 0.030 |
| O7 | 0.8664 | 0.1049 | 0.1788 | 0.034 |
| O8 | 0.3894 | −0.1997 | 0.2655 | 0.042 |
| O9 | 0.9133 | −0.3339 | 0.1451 | 0.033 |
| O10 | 0.7665 | −0.1770 | 0.2495 | 0.047 |

Figure 2:
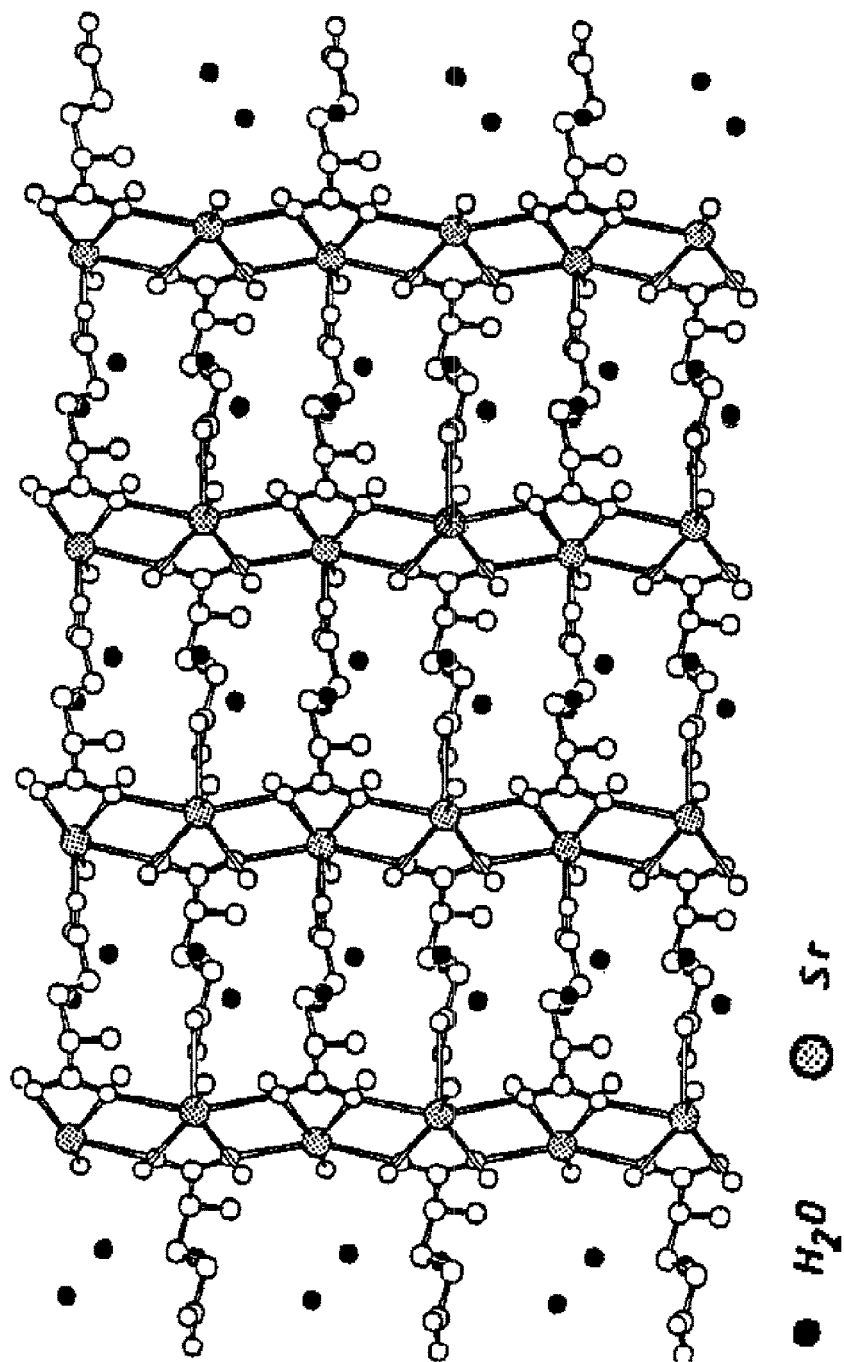
FIG. 2 is a depiction of the extended layer structure of strontium L-glutamate ($6*H_2O$) in the crystalline form as disclosed by Schmidbaur et al 1989. Strontium atoms are shown as gray and interstitial water molecules as black.

As apparent from the data disclosed in FIGS. 1 and 2 and Tables 2 and 3, the strontium glutamate salt in hexahydrate form described by Schmidbaur et al is an orthorhombic crystal form belonging to space group $P2_12_12_1$. The cell size is defined by the following dimensions (given in Å): a 3.355, b 8.772, c 20.283, with a unit cell volume of 1308.6 Å$^3$. The solubility of the isolated strontium glutamate (hexahydrate) with the properties as described (Schmidbaur, I Bach, L Wilkinson & G Müller (1989), Chem Ber. 122; 1433-1438) was reported as 0.023 g/l at 20° C.

Strontium L-aspartate has also previously been prepared by reacting L-aspartic acid with strontium hydroxide. The reaction was performed over 3 hours under reflux, and the resulting reaction mixture was allowed to cool over three days to initiate crystal formation. The resulting strontium L-aspartate crystals were subjected to X-ray crystallography in order to elucidate the crystal structure (please see: H. Schmidbaur, P. Mikulcik & G. Müller (1990), Chem Ber. 123; 1599-1602). The investigations revealed that the isolates strontium L-aspartate salt was formed in the trihydrate form with the properties described in FIG. 3 and Tables 4 and 5.

TABLE 3

Distances [Å] and angles [°] for strontium L-aspartate trihydrate as described by Schmidbaur et al 1990. For atomic numbering please see FIG. 3. The parenthesis indicates the estimated units of the last significant figure.

| Distances | | | |
|---|---|---|---|
| Sr—O1 | 2.713(4) | Sr—O2 | 2.707(5) |
| Sr—O3" | 2.666(6) | Sr—O3" | 2.635(8) |
| Sr—O4" | 2.799(7) | Sr—O4'" | 2.580(7) |
| Sr—O5 | 2.568(8) | Sr—O6 | 2.683(7) |
| Sr—O7 | 2.627(3) | O1—C1 | 1.258(7) |
| O2—C1 | 1.254(7) | C1—C2 | 1.540(8) |
| C2—C3 | 1.510(9) | C3—C4 | 1.522(7) |
| O3—C4 | 1.29(1) | O4—C4 | 1.23(1) |
| Angles | | | |
| O1—Sr—O2 | 48.0(1) | O1—Sr—O3' | 84.2(2) |
| O2—Sr—O3' | 88.5(2) | O3"—Sr—O3' | 112.4(2) |
| O4"—Sr—O3' | 65.4(2) | O5—Sr—O3' | 70.3(2) |
| O6—Sr—O3' | 140.5(2) | O3'—Sr—O4'" | 152.7(2) |
| O3'—Sr—O7 | 73.3(2) | O1—Sr—O3" | 146.9(2) |

TABLE 3-continued

Distances [Å] and angles [°] for strontium L-aspartate trihydrate as described by Schmidbaur et al 1990. For atomic numbering please see FIG. 3. The parenthesis indicates the estimated units of the last significant figure.

| O2—Sr—O3" | 152.6(2) | O3"—Sr—O4" | 48.1(1) |
|---|---|---|---|
| O3"—Sr—O5 | 97.1(2) | O3"—Sr—O6 | 78.0(2) |
| O3"—Sr—O7 | 80.8(1) | O1—Sr—O4" | 144.2(2) |
| O2—Sr—O4" | 141.9(2) | O4"—Sr—O5 | 72.6(2) |
| O4"—Sr—O6 | 107.6(2) | O4"—Sr—O7 | 76.6(2) |
| O1—Sr—O4'" | 83.3(2) | O2—Sr—O4'" | 100.8(2) |
| O3'—Sr—O4'" | 152.7(2) | O3"—Sr—O4'" | 69.0(2) |
| O4"—Sr—O4'" | 115.2(2) | O5—Sr—O4'" | 137.0(2) |
| O6—Sr—O4'" | 66.6(2) | O7—Sr—O4'" | 80.3(2) |
| O1—Sr—O6 | 107.9(2) | O2—Sr—O6 | 74.6(2) |
| O5—Sr—O6 | 70.7(1) | O1—Sr—O7 | 76.9(1) |
| O1—Sr—O5 | 115.7(2) | O2—Sr—O5 | 72.7(2) |
| O2—Sr—O7 | 123.7(1) | O5—Sr—O7 | 139.5(2) |
| O6—Sr—O7 | 145.5(2) | O1—C1—O2 | 122.5(5) |
| O1—C1—C2 | 118.2(5) | O2—C1—C2 | 119.1(5) |
| N—C2—C1 | 116.3(5) | N—C2—C3 | 111.4(6) |
| C1—C2—C3 | 109.9(5) | C2—C3—C4 | 115.2(6) |
| O3—C4—O4 | 123.8(5) | O3—C4—C3 | 117(1) |
| O4—C4—C3 | 119(1) | | |

TABLE 4

Fractional atomic coordinates and equivalent isotropic thermal parameters for strontium glutamate hexahydrate as described by Schmidbaur et al 1990.
$U_{eq} = (U_1 * U_2 * U_3)$, where $U_1$, $U_2$ and $U_3$ are the intrinsic values of the $U_{ij}$ matrix.
For atom nomenclature please refer to FIG. 3.

| Atom | X/A | Y/B | Z/C | U(eq.) |
|---|---|---|---|---|
| Sr | 0.2512 | 0.12345 | 0.01532 | 0.022 |
| O1 | 0.247 | −0.1101 | −0.1041 | 0.046 |
| O2 | 0.1997 | −0.1361 | 0.0783 | 0.039 |
| O3 | 0.3983 | −0.6359 | 0.0410 | 0.049 |
| O4 | 0.0957 | −0.6194 | 0.0327 | 0.040 |
| O5 | 0.0536 | 0.1264 | 0.1947 | 0.059 |
| O6 | 0.4661 | 0.0865 | 0.1965 | 0.033 |
| O7 | 0.238 | 0.2068 | −0.1951 | 0.039 |
| N | 0.230 | −0.3876 | −0.1511 | 0.037 |
| C1 | 0.2138 | −0.1831 | −0.0196 | 0.038 |
| C2 | 0.1785 | −0.3343 | −0.0395 | 0.036 |
| C3 | 0.263 | −0.4160 | 0.0549 | 0.046 |
| C4 | 1.1116 | −0.5682 | 0.0416 | 0.034 |

Figure 3:
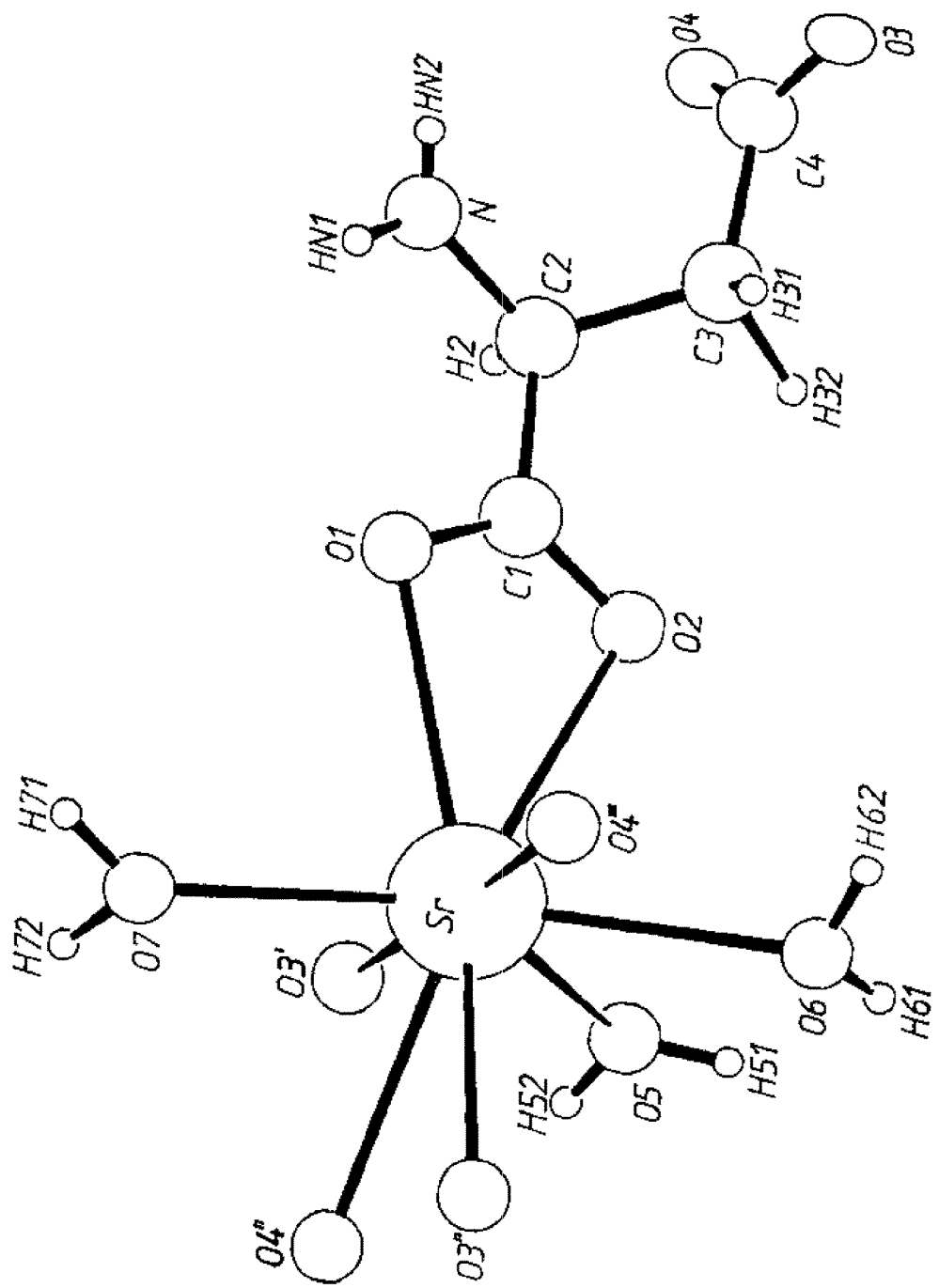
FIG. 3 is a depiction of the molecular structure of strontium L-aspartate ($3*H_2O$) in the crystalline form as disclosed by Schmidbaur et al 1990. The crystal is shown with atoms depicted with arbitrary radii. Complexation by $Sr^{2+}$ by four additional symmetrically related amino acids is indicated only by the coordinating carboxy oxygen atoms O3'/O3" and O4"/O4'". Complexation to oxygen atoms of two water molecules are visible as O6 and O7.

As apparent from the data disclosed in FIG. 3 and Tables 3 and 4, the strontium glutamate salt in hexahydrate form described by Schmidbaur et at is an orthorhombic crystal form belonging to space group $P2_12_12_1$. The cell size is defined by the following dimensions (given in Å): a 7.304, b 9.914, c 11.837, with a unit cell volume of 857.1 Å$^3$. The solubility of the isolated strontium aspartate trihydrate salt was not reported (H. Schmidbaur, P. Mikulcik & G. Müller (1990), Chem Ber. 123; 1599-1602).

Other examples of relevant acids for making strontium salts for use in a pharmaceutical composition may be found in WO 00/01692, which is hereby incorporated by reference.

Synthesis of Strontium Salts

Organic strontium salts of carboxylic acid anions can be synthesized by a number of different pathways. A conventional method for preparation of such organic strontium salts is to utilize the reaction between and organic acid and strontium hydroxide in an aqueous solution. This neutralisation reaction of, e.g. fumaric acid and strontium hydroxide salt follows the following scheme:

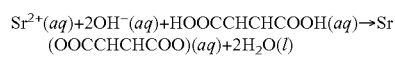

The suspension of dissolved strontium fumarate can then be induced to precipitate by sublimation of water and subsequent up-concentration of the salt. Crystals will slowly form and precipitate from the solution.

In a specific embodiment, the invention relates to a high temperature (above 90° C.) synthetic method for the preparation of kilogram-scale quantities of strontium salts, e.g., strontium malonate. The preparation can be performed in a commercial scale reactor, such as a 100 L reactor or a 300 L reactor of conventional design, and can be scaled up to even larger scale. The reactor may be built of glass, stainless steel or other chemically inert material. At the beginning of the synthesis, the reactor is charged with purified water and strontium hydroxide. The reactor is closed and atmospheric air replaced with a nitrogen atmosphere. This operation is performed, inter alia, to avoid the formation of strontium carbonate from the reaction of ionic strontium with carbon dioxide. The reaction mixture is heated to 95-100° C. after which the unclear solution is transferred to a nitrogen filled pressure filter (heated to 92-98° C.) to remove any strontium carbonate or other particulate material. The reactor can subsequently be cleaned for example, with diluted hydrochloric acid, tap water, and finally with purified water.

Another container, e.g., a 10 L polyethylene (PE) container, is charged with an organic acid, e.g., malonic acid, and purified water, and the resulting mixture is shaken until a clear solution is obtained. The solution is filtered, for example, through a sintered glass filter into the reactor, and the PE container and the filter are washed with additional purified water. The reactor is evacuated and the pressure is equilibrated with nitrogen before the solution is heated to a gentle reflux under a nitrogen atmosphere. The hot strontium hydroxide is filtered into the reactor at a rate where a gentle reflux can be maintained. In preparative methods for certain salts, e.g., strontium malonate, the reaction product will typically start to precipitate during the addition. After the addition is complete, the mixture is stirred at 95-100° C. for 20 minutes, and then cooled to 40-50° C. within 2-5 hours to yield a suspension.

The strontium salt, e.g., strontium malonate, can be recovered by filtration of the suspension in an inert atmosphere (e.g., in a nitrogen atmosphere) using, for instance, a pressure filter. The filter cake should be washed with a suitable solvent, such as purified water or ethanol, and dried to provide the desired, dried strontium salt. Skilled artisans may incorporate suitable modifications of the above-described method to accommodate larger scale preparations of the strontium salt to achieve similar results. The procedure may also be adapted to smaller scale laboratory preparations by modifications well-known to those of skill in the art.

An alternative approach for synthesis of a strontium salt is to utilize the sodium or potassium salt of the appropriate carboxylic acid anion and strontium chloride. As all organic strontium salts will be less soluble than the highly soluble chloride salt, the organic strontium salt will precipitate under these conditions leaving NaCl and excess $SrCl_2$ in the solution. The equation below exemplifies this reaction scheme using as an example the reaction between $SrCl_2$ and sodium-fumarate.

$$Sr^{2+}(aq)+2Cl^-(aq)+2Na^+(aq)+C_4H_2O_4^{2-}(aq) \rightarrow Sr(OOCCHCHCOO)(aq)+Cl^-(aq)+Na^+(aq)$$

The present inventors have found that different strontium salts requires different synthesis pathways, and for some strontium salts we have identified optimized synthesis and manufacturing procedures. Of particular relevance for the present invention, it has been found that synthesis of strontium salts of the di-carboxylic aminoacids aspartate and glutamate (in either D- or L-form) is very difficult when following these conventional reaction pathways, and generally results in low yields and purity of the obtained crystalline salt. In order to facilitate large-scale manufacture of pure strontium salts of dicarboxylic amino acids to carry out the pharmaceutical use according to the present invention, the present inventors have studied various synthesis pathways of these particular strontium salts. Thus, it has surprisingly been found that synthesis of well defined and pure strontium glutamate in hexahydrate form is most convenient carried out with the free acid form of glutamate and strontium hydroxide and requires elevated temperatures, such as temperatures above 80° C., or more preferred 100° C. or even 120° C. or most preferred more than 130° C. (see Examples 4-7). Furthermore, we have found that addition of small volumes of alcohol can accelerate the crystal-formation of dissolved aqueous organic strontium salts. In the present invention new crystalline forms of strontium salts of dicarboxylic acids are disclosed. In particular we have found that synthesis of strontium L-glutamate from L-glutamic acid and $SrCl_2$ results in a new hexahydrate crystalline form distinct from the previously described strontium L-glutamate hexahydrate as described in FIGS. 1 and 2 and Tables 2 and 3.

Examples of these synthesis procedures for organic strontium salts of relevance for the treatment and/or prophylaxis of bone disease are provided in the examples herein.

In one aspect of the invention a method for the preparation of strontium salts including strontium glutamate is provided.

The invention further relates to the strontium salts for use in medicine. As mentioned above strontium (and sometimes its counter ion such as, e.g. alpha-ketoglutarate or an amino acid) is believed to have an effect on cartilage and/or bone conditions and/or other conditions, thus the salt may be used for the preparation of a pharmaceutical composition for the treatment and/or prophylaxis of a cartilage and/or a bone condition including the ones mentioned above. The salt may also be used for the preparation of a pharmaceutical composition for the maintenance or increase of energy level, for building up or strengthening muscle tissues and for weight gain. The pharmaceutical composition may further comprise one or more physiologically acceptable excipients.

For the treatment and/or prophylaxis of a cartilage and/or bone disease and/or conditions resulting in a dysregulation of cartilage and/or bone metabolism in a mammal, the possibility of administering various amounts of strontium and, if relevant alpha-ketoglutarate or an amino acid like e.g. glutamic acid and/or aspartic acid, respectively, may be desired. The amount of strontium (and, if relevant e.g. alpha-ketoglutarate or an amino acid) in a pharmaceutical composition according to the invention may be adjusted by adding an additional amount of strontium in the form of a strontium-containing compound (and/or, if relevant, an additional amount of alpha-ketoglutarate or an amino acid) to the composition. The strontium-containing compounds may be selected from the salts mentioned above.

In certain cases it may be beneficial to further add one or more active substances to a pharmaceutical composition according to the invention. The one or more active substances may have a therapeutic and/or prophylactic effect on a cartilage and/or a bone disease and/or other conditions such as those mentioned above. The term "active substance having a therapeutic and/or prophylactic effect on diseases and conditions affecting metabolism and structural integrity of cartilage and/or bone" includes active substances that can attain a particular medical result, such as, e.g., reduce the incidence of bone fracture, increase bone density and/or improve healing of bone or decrease or halt the degradation of articular cartilage or promote formation of new cartilage or prevent or decrease progression of radiological evident joint damage. Examples of such substances are bone anti-resorptive and/or anabolic agents. However, one or more active substances having other effects than those mentioned above may also be included in a pharmaceutical composition of the invention. Such active substances could be e.g. disease-modifying anti-rheumatic drugs, or other anti-rheumatic drugs.

Specific examples of active substances, which may be used in a pharmaceutical composition according to invention are calcium-alpha-ketoglutarate, calcium and/or salts thereof, vitamin D such as, e.g., vitamin $D_3$ and/or functional equivalents of vitamin $D_3$, glucagon-like peptide-2, glucagon-like peptide-2 releasing compositions, bisphosphonates including ibandronate, zoledronate, alendronate, risedronate, ethidronate chlodronate, tiludronate and pamidronate; selective estrogen receptor modulators (SERMs) including raloxifene, arzoxifene, droloxifene, tamoxifen, 4-hydroxy-tamoxifen, 4'-iodotamoxifen, toremifene, (deaminohydroxy)-toremifene, chlomiphene, levormeloxifene, ormeloxifene, chroman derivatives, coumarin derivatives, idoxifene, nafoxidine, TAT-59, LY-353381, CP-336156, MDL-103323, EM-800, ICI-182, ICI 183,780, ICI 164,384, ICI 183,780, ICI 164,384, diethylstilbesterol, genistein, nafoxidine, nitromifene citrate, moxesterol, diphenol hydrochrysene, erythro-MEA, allenolic acid, equilin-3-sulphate, cyclophenyl, chlorotrianisene, ethamoxytriphetol, lasofoxifene, bazedoxifene, genistein, tibolone, ospemifene, tesmilifene, droloxifene, panomifene, zindoxifene, meproxifene and faslodex; calcitonin, parathyroid hormone, parathyroid hormone related peptide, glucosamine sulphate, glutamic acid and/or salts thereof, aspartic acid and/or salts thereof, proline, glutamine and hydroxyproline.

As mentioned above, the compounds and compositions of the present invention may be used for the treatment and prophylaxis of various conditions. Thus, the present invention relates to a method for the treatment and/or prophylaxis of a cartilage and/or bone disease and/or conditions resulting in a dysregulation of cartilage and/or bone metabolism in a mammal, such as the ones mentioned above, for the maintenance or increase of energy level, for building up or strengthening muscle tissues and for weight gain, the method comprising administering to a subject in need thereof a therapeutic and/or prophylactic effective amount of a strontium salt having a water-solubility in the range claimed herein.

The subject may be a mammal, such as, e.g. a human or a domestic animal, such as, e.g., a cat, a dog, a horse, a cow or a sheep.

The invention also relates to a method for the treatment and/or prophylaxis of a cartilage and/or bone disease and/or conditions resulting in a dysregulation of cartilage and/or bone metabolism in a mammal, such as the ones mentioned above, for the maintenance or increase of energy level, for building up or strengthening muscle tissues and for weight gain, the method comprising administering to a subject in need thereof an amount of the strontium salt according to the invention.

The daily dose of strontium may be at least about 0.01 g, such as, e.g., at least about 0.025 g, at least about 0.050 g, at least about 0.075 g, at least about 0.1 g, at least about 0.2 g, at least about 0.3 g, at least about 0.4 g or at least about 0.5 g or from about 0.01 g to about 2 g such as, e.g., from about 0.1 g to about 2 g, from about 0.3 g to about 2 g or from about 0.3 g to about 1 g.

The invention also relates to a method wherein the strontium salt is administered in the form of a pharmaceutical composition as described above.

The invention further relates to a method wherein the administration may take place one or more times daily, such as from 1 to 5 times daily.

The invention also relates to a method wherein the administration may take place one or more times weekly, such as from 1 to 3 times weekly.

In a specific embodiment, the invention relates to a method for the treatment of and/or prophylaxis of a bone disease and/or condition resulting in a dysregulation of bone metabolism in a subject, comprising administering a strontium salt, e.g., strontium malonate, to the subject, wherein the strontium salt provides a maximum plasma concentration of strontium from about 4 to about 24 hours after administration to the subject. The strontium salt is preferably not strontium ranelate. In a specific embodiment, such a pharmacokinetic profile is achieved after administration of a single dose of the strontium salt, e.g., strontium malonate, to the subject. In certain embodiments, the administration comprises oral administration of the strontium salt to the subject. In a specific embodiment, such a pharmacokinetic profile is achieved after administration of a single oral dose of the strontium salt to the subject. The administration may, for example, include administration of a tablet to the subject.

In some embodiments, the strontium salt, e.g., strontium malonate, provides a maximum plasma concentration of strontium from about 5.5 to 24 hours, e.g., from about 5.5 to about 10 hours, after administration to the subject. In other embodiments, the strontium salt provides a maximum plasma concentration from about 4 to about 8 hours, or from about 5 to about 10 hours, after administration to said subject.

In certain embodiments of the method, the maximum plasma concentration of strontium is at least 1.5 times higher than the plasma concentration of strontium at 2 hours after administration to said subject. In a specific embodiment of the method, the maximum plasma concentration of strontium is from about 2 mg/L to about 10 mg/L.

In another embodiment, the invention relates to a method for the treatment of and/or prophylaxis of a bone disease and/or condition resulting in a dysregulation of bone metabolism in a subject, comprising administering to the subject a pharmaceutical composition comprising a strontium salt, e.g., strontium malonate, and one or more pharmaceutically acceptable excipients, wherein the pharmaceutical composition provides a maximum plasma concentration of strontium from about 4 to about 24 hours after administration to the subject. The strontium salt is preferably not strontium ranelate. In certain embodiments, the administration comprises oral administration of the pharmaceutical composition to the subject. In a specific embodiment, such a pharmacokinetic profile is achieved after administration of a single oral dose of the strontium salt, e.g., strontium malonate, to the subject. The pharmaceutical composition may be, for example, a tablet.

In certain embodiments of the method, the maximum plasma concentration of strontium is at least 1.5 times higher than the plasma concentration of strontium at 2 hours after administration of the pharmaceutical composition to the subject. In a specific embodiment of the method, the maximum plasma concentration of strontium is from about 2 mg/L to about 10 mg/L.

In yet another embodiment, the invention relates to a pharmaceutical composition comprising a strontium salt, e.g., strontium malonate, and one or more pharmaceutically acceptable excipients, wherein the pharmaceutical composition provides a maximum plasma concentration of strontium from about 4 to about 24 hours after administration of the pharmaceutical composition to a subject. In a specific embodiment, the strontium salt is preferably not strontium ranelate.

In certain embodiments, the pharmaceutical composition provides a maximum plasma concentration of strontium from about 5.5 to 24 hours, e.g., from about 5.5 to about 10 hours, after administration to the subject. In other embodiments, the pharmaceutical composition provides a maximum plasma concentration from about 4 to about 8 hours, or from about 5 to about 10 hours, after administration to said subject.

In some embodiments of the pharmaceutical composition, the maximum plasma concentration of strontium is at least 1.5 times higher than the plasma concentration of strontium at 2 hours after administration of the pharmaceutical composition to the subject. In a specific embodiment, the maximum plasma concentration of strontium is from about 2 mg/L to about 10 mg/L.

In certain embodiments, the pharmaceutical composition comprises from about 0.01 to about 2 g of strontium. For instance, the pharmaceutical composition may comprise from about 0.1 to about 2 g of strontium. In a specific embodiment, the pharmaceutical composition comprises a tablet.

In yet another aspect, the invention relates to a method for the treatment of and/or prophylaxis of a bone disease and/or condition resulting in a dysregulation of bone metabolism in a subject, comprising administering to the subject a pharmaceutical composition comprising a strontium salt, e.g., strontium malonate, and one or more pharmaceutically acceptable excipients to provide a steady state plasma concentration of from about 5 to about 50 mg/L of strontium in the subject after repeated administration through steady state conditions, wherein the strontium salt is not strontium ranelate. In some embodiments, the administration includes oral administration (such as with a tablet) to the subject. In specific embodiments of the method, the steady state plasma concentration provided in the subject is from about 8 to about 20 mg/L of strontium.

The frequency of the administration of the pharmaceutical composition may vary depending on, inter alia, the particular properties of the pharmaceutical composition in which the strontium salt is administered. In specific embodiments, the pharmaceutical composition is administered at least every 6 hours, such as every 12 hours, every 24 hours, every 48 hours, through steady state conditions.

Steady state plasma levels of strontium through administration of the strontium salts of the invention, or pharmaceutical composition thereof, to a subject may be achieved by methods known to those of skill in the art. In a particular embodiment of the invention an oral pharmaceutical composition containing approximately 1.2 g of strontium malonate is administered to a subject in need thereof once daily. In a specific embodiment, the composition may be administered to the subject for at least ten consecutive days, such as at least ten to fourteen consecutive days, to obtain a steady state plasma concentration of strontium. As will be apparent to those of skill in the art, at steady state the plasma concentration of strontium will fluctuate over the course of the day, with the lowest levels just before intake of the pharmaceutical composition, and the highest levels ($C_{max}$) obtained after a number of hours after intake of the pharmaceutical composition. Under steady state conditions, this variation should preferably be below 40% (understood as the difference between the lowest and highest plasma concentration expressed in % of the average levels observed over a 24 hour period in a subject given the strontium containing pharmaceutical composition). Skilled artisans will recognize that such variations will influence the magnitude of the fluctuations in plasma strontium levels observed over a 24 hour period. A person skilled in the art may realize that there may be other clinically acceptable ways of obtaining a steady state level of strontium plasma level, and that especially the administration of the pharmaceutical composition may be done in a number of alternative ways, such as twice or more daily.

In another aspect, the invention relates to a pharmaceutical composition comprising a strontium salt, e.g., strontium malonate, and one or more pharmaceutically acceptable excipients, wherein the pharmaceutical composition provides a steady state plasma concentration in a subject of from about 5 to about 50 mg/L of strontium after repeated administration of the pharmaceutical composition to said subject through steady state conditions, wherein the strontium salt is not strontium ranelate. In specific embodiments, the pharmaceutical composition provides a steady state plasma concentration in a subject of from about 8 to about 20 mg/L of strontium after repeated administration of the pharmaceutical composition to said subject through steady state conditions. In a specific embodiment, the pharmaceutical composition comprises a tablet.

In some embodiments, the pharmaceutical composition comprises from about 0.01 to about 2 g of ionic strontium. In this context it will be understood that ionic strontium refers to the amount of free strontium ion $Sr^{++}$, and that the actual amount of strontium compound (e.g., strontium salt) must be calculated based on the empirical formula and formula weight of the specific salt utilized.

As described above, one or more active substances may be added to a pharmaceutical composition according to the invention, or administered as part of the same treatment as the administration of strontium salt. One example of such an active substance is Vitamin D. Vitamin D plays a major role in calcium absorption, since activated vitamin $D_3$ (1,25-dihydroxycholecalciferol) and to a smaller extent other active forms of vitamin D, acts to increase the calcium absorption from the small intestine. Vitamin $D_3$ acts to increase the entry of calcium through the plasma membrane into the enterocytes, and is capable of reducing the excretion of calcium to urine by increasing the reabsorbtion of calcium in kidneys. It is likely that vitamin D has the same effect on strontium absorption as it has on calcium absorption.

Vitamin D is activated in e.g. the liver and kidneys. High levels of calcium are having a reducing effect on activation of vitamin D, and high levels of strontium will probably have the same effect as calcium on the activation of vitamin D.

Thus, the administration of an amount of vitamin D together with a strontium-containing compound according to the invention will most likely have a beneficial effect on the uptake of strontium.

Accordingly, the invention relates to a method according to the invention further comprising administering a daily dose of vitamin D.

In a specific embodiment, vitamin D may be vitamin $D_3$, and the daily dose of vitamin $D_3$ may be at least about 1 µg, such as, e.g. at least about 1.25 µg at least about 1.50 µg, at least about 2 µg, at least about 3 µg, at least about 4 µg, at least about 5 µg, at least about 10 µg, at least about 15 µg, at least about 20 µg, at least about 25 µg, at least about 30 µg, at least about 40 µg or at least about 50 µg or from about 1 µg to about 50 µg such as, e.g., from about 1.50 µg to about 40 µg, from about 2 µg to about 30 µg, from about 3 µg to about 30 µg, from about 4 µg to about 30 µg, from about 5 µg to about 30 µg, from about 10 µg to about 30 µg, from about 10 µg to about 20 µg or from about 15 µg to about 25 µg.

More specifically, the daily dose of vitamin $D_3$ may be from about 5 μg to about 30 μg, such as, e.g., from about 10 μg to about 20 μg.

In a further method according to the invention, the strontium component may be administered in a dose corresponding to a daily dose of from about 0.3 g to about 1 g, the alpha-ketoglutarate component may be administered in a dose corresponding to a daily dose of from about 2 g to about 7 g and vitamin $D_3$ may be administered in a dose corresponding to a daily dose of from about 10 μg to about 20 μg.

Another active form of vitamin D to be used in a method according to the invention is vitamin $D_2$. The daily dose of vitamin $D_2$ may be at least 1 μg, such as, e.g. at least about 1.50 μg, at least about 2 μg, at least about 3 μg, at least about 4 μg, at least about 5 μg, at least about 10 μg, at least about 15 μg, at least about 20 μg, at least about 25 μg, at least about 30 μg, at least about 40 μg, at least about 50 μg, at least about 60 μg, at least about 70 μg, at least about 80 μg, at least about 90 μg, at least about 100 μg, at least about 110 μg, at least about 120 μg or at least about 125 μg or from about 1 μg to about 125 μg such as, e.g., from about 1.50 to about 120 μg, from about 2 μg to about 110 μg, from about 3 μg to about 100 μg, from about 4 μg to about 90 μg, from about 5 μg to about 80 μg, from about 5 μg to about 125 μg, from about 10 μg to about 70 μg, from about 10 μg to about 60 μg, from about 10 μg to about 50 μg, from about 10 μg to about 40 μg, from about 10 μg to about 30 μg, from about 10 μg to about 20 μg, or from about 15 μg to about 25 μg.

More specifically, the daily dose of vitamin $D_2$ is from about 5 μg to about 125 μg, such as, e.g., from about 10 μg to about 20 μg.

Other functional equivalents of vitamin $D_3$ and $D_2$, such as alphacalcidol, calcitriol or dihydrotachysterol, may also be administered according to the invention. Alpha-calcidiol, 1α-hydroxy-cholecalciferol, may be administered in amounts of 0.2-3 μg/day, preferably 0.25-2 μg/day. Calcitriol, 1,25-dihydroxy-cholecalciferol, may be administered in amounts of 0.1-10 μg/day, preferably 0.125-2 μg/day and dihydrotachysterol, a vitamin D2 analogue, may be administered in amounts of 0.1-3 mg/day, preferably 0.2-0.6 mg/day.

In yet a further method, the administration of the strontium component, the alpha-ketoglutarate or amino acid component, if relevant, and vitamin D takes place simultaneously.

In another method, the administration of the strontium component, the alpha-ketoglutarate or amino acid component, if relevant, and/or vitamin D take place sequentially.

Calcium is another example of an active substance that may be administered as part of the same treatment as the administration of strontium salt. Calcium is the most abundant mineral in the body, and a major constituent of bone and teeth as calcium phosphate and calcium carbonate. Calcium is also essential in intra- and extracellular fluid exchange, blood clotting, and in maintaining a regular heartbeat. It is also important in the initiation of neuromuscular as well as metabolic functions. Most of the calcium in the body is stored in the bones.

Thus, calcium is an important participant in many processes in the body, and administration of calcium may have a therapeutic and/or prophylactic effect on many of the diseases and conditions mentioned above.

Accordingly, the present invention relates to a method as described above further comprising administering a daily dose of calcium.

In a specific method according to the invention the daily dose of calcium is from about 0.5 g to about 2 g such as, e.g., 0.5 g to about 1.5 g, from 0.5 g to 1 g and from about 1 g to about 1.5 g.

In yet another method according to the invention, the strontium component is administered in a dose corresponding to a daily dose of from about 0.3 g to about 1 g, the alpha-ketoglutarate or amino acid component is administered in a dose corresponding to a daily dose of from about 2 g to about 7 g and the dose of calcium corresponds to a daily dose of from about 0.5 g to about 1 g.

The administration of the strontium salt, the alpha-ketoglutarate or amino acid component, if relevant, and calcium may take place simultaneously, either in a single administration form or in separate administration forms for simultaneous administration as described above.

Alternatively, the strontium salt, the alpha-ketoglutarate or amino acid component, if relevant, and calcium may be administered sequentially.

Studies have shown that strontium is a full agonist of the calcium-sensing receptor (CaR). Even though the role of the CaR in regulating bone cells is not fully investigated, it appears that strontium and calcium may exert their effect on bone metabolism via the same receptor.

Accordingly, it may be beneficial not to administer the strontium-containing component and calcium at the same time.

In one aspect of the present invention, calcium may be administered after the administration of strontium, i.e. the invention relates to a method, wherein calcium is administered at least 0.5 h, such as, e.g., at least 1 h, at least 2 h, at least 3 h, at least 4 h, at least 5 h, at least 6 h, at least 7 h, at least 8 h, at least 9 h, at least 10 h, at least 11 h or at least 12 h after the administration of the strontium component.

In another aspect calcium may be administered before the administration of strontium, i.e. the invention relates to a method, wherein calcium is administered at least 0.5 h, such as, e.g., at least 1 h, at least 2 h, at least 3 h, at least 4 h, at least 5 h, at least 6 h, at least 7 h, at least 8 h, at least 9 h, at least 10 h, at least 11 h or at least 12 h before the administration of the strontium component.

In yet another aspect, the strontium salt and the alpha-ketoglutarate or amino acid component, if relevant, may be administered simultaneously and calcium may be administered at least 1 h, such as, e.g., at least 2 h, at least 3 h, at least 4 h, at least 5 h, at least 6 h, at least 7 h, at least 8 h, at least 9 h, at least 10 h, at least 11 h or at least 12 h after the administration of the strontium salt.

In a further aspect, the strontium salt and the alpha-ketoglutarate or amino acid component, if relevant, may be administered simultaneously and calcium may be administered at least 1 h, such as, e.g., at least 2 h, at least 3 h, at least 4 h, at least 5 h, at least 6 h, at least 7 h, at least 8 h, at least 9 h, at least 10 h, at least 11 h or at least 12 h before the administration of the strontium salt.

In yet a further aspect, calcium and vitamin D may be administered simultaneously at least 1 h, such as, e.g., at least 2 h, at least 3 h, at least 4 h, at least 5 h, at least 6 h, at least 7 h, at least 8 h, at least 9 h, at least 10 h, at least 11 h or at least 12 h before the simultaneously administration of a strontium salt and vitamin D.

In another aspect calcium and vitamin D may be administered simultaneously in the morning, and a strontium salt and vitamin D may be administered simultaneously in the evening.

A further example of an active substance that may be administered as part of the same treatment as the administration of strontium is parathyroid hormone. Parathyroid hormone is composed of 84 amino acid residues and is released in vivo in response to a decrease in the level of extra cellular calcium. Administration of PTH or fragments thereof in a pharmaceutically relevant dose is known to stimulate bone formation, produce a robust increase in bone mineral density and substantially reduce the occurrence of vertebral and non-vertebral fractures. Parathyroid hormone acts directly on the kidney to diminish urinary calcium, and increases bone resorption via an indirect mechanism involving osteoblasts. Parathyroid hormone also increases the activation of vitamin D by stimulating the activity of 1α-hydroxylase enzyme in the kidney, subsequently leading to a better absorption of calcium and, possibly, strontium.

A commercially available parathyroid hormone containing drug comprises the 34 N-terminal amino acids region of human parathyroid hormone, which is believed to be the biologically active region.

Accordingly, in a further method according to the invention an amount of parathyroid hormone, or a fragment or analogue thereof, or a parathyroid hormone related peptide, or a fragment or analogue thereof, is administered as part of the same treatment as the administration of strontium salt. In the following the term "PTH" covers parathyroid hormone, fragments, analogues and functional analogues thereof together with parathyroid related hormone and fragments, analogues and functional analogues thereof. PTH may be used as a combined or sequential administration with strontium and, if relevant, alpha-ketoglutarate.

The daily dose of PTH, when calculated as recombinant human parathyroid hormone (1-34), may be at least 1 μg, such as, e.g. at least about 2 μg, at least about 3 μg, at least about 4 μg, at least about 5 μg, at least about 10 μg, at least about 15 μg, at least about 20 μg, at least about 25 μg, at least about 30 μg, at least about 35 μg, at least about 40 μg, at least about 50 μg, or at least about 60 μg, or from about 1 μg to about 60 μg such as, e.g., from about 2 to about 50 μg, from about 3 μg to about 40 μg, from about 4 μg to about 40 μg, from about 5 μg to about 40 μg, from about 10 μg to about 40 μg, from about 10 μg to about 35 μg, from about 10 μg to about 30 μg, from about 10 μg to about 25 μg, from about 10 μg to about 20 μg, from about 15 μg to about 40 μg, from about 20 μg to about 40 μg or from about 20 μg to about 30 μg.

More specifically, the daily dose of PTH, when calculated as recombinant human parathyroid hormone (1-34), may be from about 10 μg to about 40 μg, such as, e.g., from about 10 μg to about 30 μg, from about 10 μg to about 20 μg, from about 20 μg to about 40 μg or from about 20 μg to about 30 μg.

The medical treatment according to the invention may comprise administration of a daily dose of bisphosphonate from about 0.1 mg to 60 mg, such as from about 0.2 mg to about 30 mg, from about 0.2 mg to about 20 mg or from about 0.2 mg to about 10 mg.

In a combination treatment according to the invention in which a strontium containing compound is given in combination with one or more SERM's, the SERM should be used in a dose as determined previously from clinical investigation of the given SERM.

In the following is given a more detailed description of individual salts according to the invention. Especially, with respect to strontium alpha-ketoglutarate and amino acid salts of strontium, these salts have two active principles, i.e. the strontium part and the alpha-ketoglutarate or amino acid part. Accordingly, these aspects of the invention include individual dose adjustment by addition e.g. of a separate dose of one of the individual components. However, all details with respect to strontium apply also for all the other strontium salts according to the invention.

Furthermore, the details and particulars described above for strontium salts apply mutatis mutandis to the individual strontium salts, whenever relevant, as well as details and particular described below for the individual strontium salts apply mutatis mutandis to the strontium salts in general, whenever relevant.

Strontium/Alpha-Ketoglutarate Salts and Compositions

Bone consists of an organic matrix comprising predominantly collagen type I, and an inorganic phase comprising calcium phosphate and calcium carbonate. The amino acid sequence of collagen type I is remarkably regular with nearly every third residue being glycine. Proline is also present to a much greater extent in collagen than in most other proteins. Moreover, the sequence glycine-proline-4-hydroxyproline recurs frequently. Alpha-ketoglutarate (AKG) is presumed to be a bone mineral density increasing and bone strength increasing agent for the treatment of osteoporosis and other bone conditions since alpha-ketoglutarate is a precursor of glutamate, which may be converted to proline, an important component of collagen. Alpha-ketoglutarate also participates in the conversion of proline to 4-hydroxyproline. The proline residues in collagen may be hydroxylated at C-4 by prolyl hydroxylase to form 4-hydroxyproline. For this process alpha-ketoglutarate, molecular oxygen and ascorbate are required.

Furthermore, alpha-ketoglutarate is a very important intermediate in the citric acid cycle. In the citric acid cycle acetyl CoA is completely oxidized to $CO_2$ via interconversions of various carboxylic acids, including AKG. This results in the reduction of NAD and FAD to NADH and $FADH_2$, whose reducing power is then used indirectly in the synthesis of ATP.

For the treatment and/or prophylaxis of a cartilage and/or bone disease and/or conditions resulting in a dysregulation of cartilage and/or bone metabolism in a mammal, such as, e.g., a human female or male adult, adolescent or a child, such as, e.g., osteoporosis, osteoarthritis, osteopetrosis, osteopenia and Paget's disease, hypercalcemia of malignancy, periodontal disease, hyperparathyroidism, periarticular erosions in rheumatoid arthritis, osteodystrophy, myositis ossificans, Bechterew's disease, malignant hypercalcemia, osteolytic lesions produced by bone metastasis, bone pain due to bone metastasis, bone loss due to sex steroid hormone deficiency, bone abnormalities due to steroid hormone treatment, bone abnormalities caused by cancer therapeutics, osteomalacia, Bechet's disease, hyperostosis, metastatic bone disease, immobilization-induced osteopenia or osteoporosis, or glucocorticoid-induced osteopenia or osteoporosis, osteoporosis pseudoglioma syndrome, idiopathic juvenile osteoporosis, for the improvement of fracture healing after traumatic or atraumatic fracture, and for the maintenance or increase of energy level, for building up or strengthening muscle tissues and for weight gain, the present inventors have found that the use of a strontium containing compound together with an alpha-ketoglutarate-containing compound has prophylactic and/or therapeutic value in that one or more of the following beneficial effects can be obtained:

i an improved bioavailability of strontium and/or alpha-ketoglutarate,
ii an improved absorption of strontium and/or alpha-ketoglutarate,
iii a reduction of side effects,
iv a flexible dose adjustment of strontium and alpha-ketoglutarate in order to tailor prevention and/or treatment of a specific disease stage,
v an additive and possible synergistic effect of strontium and alpha-ketoglutarate,
vi a possible reduction in daily dosage
vii a possible reduction of the number of different pharmaceutical compositions that a patient must use to achieve a therapeutic effect.

Thus, it is believed that strontium administered together with alpha-ketoglutarate gives a more efficient prevention and/or treatment than either strontium or alpha-ketoglutarate administered alone. This implies that smaller doses of strontium and alpha-ketoglutarate may be used when administered together, as compared to individual administration of the two compounds. The daily dose of alpha-ketoglutarate needed for the treatment and/or prophylaxis of some of the above-mentioned conditions may be rather large, i.e. the subject in the need of treatment will have to take large amounts of alpha-ketoglutarate at a time, or the frequency of intake of the doses may be high, both being of great inconvenience for the subject. The possibility of using smaller doses of strontium and alpha-ketoglutarate would be much more convenient for the subject in the need of treatment.

Thus, the invention relates to a pharmaceutical composition comprising a therapeutic and/or prophylactic effective amount of one or more first components containing a strontium compound and one or more second components containing an alpha-ketoglutarate compound, together with one or more physiologically acceptable excipients.

The above-mentioned strontium salts of organic or inorganic acids and salts of alpha-ketoglutamic acid may be in a composition as described above. The salts may be in hydrate, anhydrous, solvate, polymorphous, amorphous, crystalline, microcrystalline or polymeric form. In one embodiment of the invention only non-radioactive isotopes of strontium are used.

Below follows examples of salts of alpha-ketoglutamic acid, which may be used to adjust the amount of alpha-ketoglutarate in a pharmaceutical composition comprising strontium alpha-ketoglutarate, or in a pharmaceutical composition comprising a strontium-containing compound and an alpha-ketoglutarate compound as described above. The salt may be a salt of an alkali metal, a mixed salt of alkali metals, an alkaline earth metal, or mixtures thereof.

Specific examples of salts for use according to the invention may be sodium alpha-ketoglutarate, potassium alpha-ketoglutarate, lithium alpha-ketoglutarate, magnesium alpha-ketoglutarate, calcium alpha-ketoglutarate and mixtures thereof.

The salt may also be a salt of an amine or an amino acid or an ammonium salt or mixtures thereof. The amine may be selected from methyl amine, ethyl amine, propyl amine, isopropyl amine and butyl amine, and the amino acid may be selected from arginine, ornithine, lysine and histidine.

As exemplified by the salts mentioned above, the counter ions in the strontium and alpha-ketoglutarate-containing compounds may be active substances having the same medical indications as strontium and alpha-ketoglutarate. Examples of such compounds are e.g., strontium glutamate and calcium alpha-ketoglutarate. A composition containing strontium and alpha-ketoglutarate could therefore contain strontium glutamate and calcium alpha-ketoglutarate. However, treatment of some conditions will require relatively large doses of strontium and alpha-ketoglutarate to be administered. This makes the total amount of such a pharmaceutical composition that has to be administered to the subject in the need of treatment relatively large, which may be of great inconvenience to the subject.

The present inventors have found a novel strontium salt of alpha-ketoglutamic acid with the following formula I:

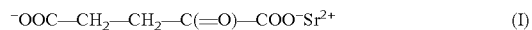

$$^{-}OOC-CH_2-CH_2-C(=O)-COO^{-}Sr^{2+} \qquad (I)$$

which may be in a hydrate, anhydrous, solvate, polymorphous, amorphous, crystalline, microcrystalline or polymeric form.

The novel salt of the above-mentioned formula is composed of two active substances, i.e. a bone anti-resorptive and bone anabolic agent in the form of strontium, and then a further amount of a bone mineral density increasing, bone strength and bone quality increasing agent in the form of alpha-ketoglutarate. As compared to previous known strontium salts, such as, e.g., strontium ranelate or strontium chloride, wherein only the strontium ion has a therapeutic and/or prophylactic effect on bone and/or cartilage diseases, both components in the novel salt are active components having a therapeutic and/or prophylactic effect.

By using the novel salt in pharmaceutical formulations, it may be possible to reduce the size of the formulations, even though the same dose of strontium and alpha-ketoglutarate is administered as in formulations comprising strontium and alpha-ketoglutarate as separate salts, together with their respective counter ions.

Furthermore, as described above the combination of strontium and alpha-ketoglutarate in the novel salt may have additive or synergistic beneficial effects on bone and/or cartilage tissue. Furthermore, the novel salt has suitable properties with respect to physio-chemical properties such as, e.g., water solubility; and it has technical properties suitable for processing the novel salt into pharmaceutical compositions.

The invention also relates to a process for preparing the novel strontium alpha-ketoglutarate substance according to the invention. The salt may be prepared by any method known to a person skilled in the art for preparing such salt. One example of such a process comprises reacting a salt of strontium with alpha-ketoglutamic acid or a salt thereof, wherein the molar ratio of strontium to alpha-ketoglutamic acid may be 1:1. A more specific example comprises reacting alpha-ketoglutamic acid with strontium hydroxide and/or strontium oxide, wherein the molar ratio of strontium to alpha-ketoglutarate optionally may be 1:1. Yet another example of such a process comprises reacting strontium metal with alpha-ketoglutamic acid. As disclosed in Examples 4-7 the invention also relates to specific methods of producing the strontium salt of the invention involving synthesis at temperatures above 100° C.

The invention also relates to a method for the treatment and/or prophylaxis of a cartilage and/or bone disease and/or conditions resulting in a dysregulation of cartilage and/or bone metabolism in a mammal, such as the ones mentioned above, for the maintenance or increase of energy level, for building up or strengthening muscle tissues and for weight gain, the method comprising administering to a subject in need thereof an amount of the strontium alpha-ketoglutarate salt according to the invention.

In the latter method wherein strontium alpha-ketoglutarate is administered, the salt may be administered in a dose corresponding to from about 0.1 to about 17 g daily calculated as anhydrous salt. More specifically, the salt may be administered in a dose corresponding to from about 0.2 to about 15 g daily such as, e.g., from about 0.4 to about 13 g daily, from about 0.6 to about 12 g daily or from about 0.7 to about 11.5 g daily calculated as anhydrous salt.

As described above, depending on the condition the subject is having, there might be a need for increasing and/or adjusting the amounts of strontium and alpha-ketoglutarate administered. Thus, the invention further relates to a method, which comprises the administration of an additional dose of a strontium-containing compound and/or an additional dose of an alpha-ketoglutarate-containing compound together with strontium alpha-ketoglutarate. The strontium-containing and alpha-ketoglutarate containing compounds may be selected from the compounds described above.

For the method wherein the strontium alpha-ketoglutarate salt is administered, optionally together with an additional amount of strontium and/or alpha-ketoglutarate, and the method wherein one or more strontium-containing compounds and one or more alpha-ketoglutarate-containing compounds are administered, the weight ratio between the total daily dose of strontium and the total daily dose of alpha-ketoglutarate may be from about 0.01 to about 4, such as, e.g., from about 0.01 to about 4, from about 0.01 to about 2, from about 0.01 to about 1, from about 0.01 to about 0.6, from about 0.03 to about 4, from about 0.03 to about 2, from about 0.03 to about 1, from about 0.1 to about 2, from about 0.1 to about 1, from about 0.15 to about 0.5, about 0.2 to about 2, from about 0.3 to about 2 or from about 0.4 to about 2.

The daily dose of alpha-ketoglutarate may be at least about 0.5 g, such as, e.g., at least about 1.0 g, at least about 1.5 g, at least about 2.0 g, at least about 2.5 g, at least about 3.0 g, at least about 4 g, at least about 5 g or from about 0.5 g to about 10 g, from about 0.5 g to 7 g, from about 2 g to about 10 g or from about 2 g to about 7 g.

In a method according to the invention, the strontium component and the alpha-ketoglutarate component may be administered in single compositions or simultaneously in separate, co-administered compositions. Strontium and alpha-ketoglutarate may be in the form of strontium alpha-ketoglutarate, optionally with an additional amount of a strontium-containing compound and/or an alpha-ketoglutarate-containing compound. The additional component may be added to the strontium alpha-ketoglutarate in the same composition, or may be in a separate composition intended for simultaneous administration.

Strontium and alpha-ketoglutarate may also be combined as a mixture of one or more strontium-containing compounds and one or more alpha-ketoglutarate-containing compounds in the same formulation, or in separate forms intended for simultaneous administration. When two or more separate formulations are being co-administered, each formulation, especially those for use by oral route, may be color-coded or otherwise easily identifiably labeled in order to avoid confusion by the subject or physician.

In another method according to the invention, the administration of the strontium component and the alpha-ketoglutarate component may take place sequentially.

The invention also relates to a kit for use in the treatment and/or prophylaxis of a cartilage and/or bone disease and/or conditions resulting in a dysregulation of cartilage and/or bone metabolism in a mammal, such as, e.g., a human female or male adult, adolescent or a child, such as, e.g., osteoporosis, osteoarthritis, osteopetrosis, osteopenia and Paget's disease, hypercalcemia of malignancy, periodontal disease, hyperparathyroidism, periarticular erosions in rheumatoid arthritis, osteodystrophy, myositis ossificans, Bechterew's disease, malignant hypercalcemia, osteolytic lesions produced by bone metastasis, bone pain due to bone metastasis, bone loss due to sex steroid hormone deficiency, bone abnormalities due to steroid hormone treatment, bone abnormalities caused by cancer therapeutics, osteomalacia, Bechet's disease, hyperostosis, metastatic bone disease, immobilization-induced osteopenia or osteoporosis, or glucocorticoid-induced osteopenia or osteoporosis, osteoporosis pseudoglioma syndrome, idiopathic juvenile osteoporosis, for the improvement of fracture healing after traumatic or atraumatic fracture, and for the maintenance or increase of energy level, for building up or strengthening muscle tissues and for weight gain, the kit comprising at least a first and a second component, the first component comprising strontium alpha-ketoglutarate and one or more second components comprising at least one of the following: i) a further strontium containing compound, ii) a further alpha-ketoglutarate containing compound, iii) a calcium containing compound, iv) a further active substance, such as, e.g. vitamin D.

The invention also relates to a kit for use in the treatment and/or prophylaxis of a cartilage and/or bone disease and/or conditions resulting in a dysregulation of cartilage and/or bone metabolism in a mammal, such as, e.g., a human female or male adult, adolescent or a child, such as, e.g., such as, e.g., osteoporosis, osteoarthritis, osteopetrosis, osteopenia and Paget's disease, hyper-calcemia of malignancy, periodontal disease, hyperparathyroidism, periarticular erosions in rheumatoid arthritis, osteodystrophy, myositis ossificans, Bechterew's disease, malignant hypercalcemia, osteolytic lesions produced by bone metastasis, bone pain due to bone metastasis, bone loss due to sex steroid hormone deficiency, bone abnormalities due to steroid hormone treatment, bone abnormalities caused by cancer therapeutics, osteomalacia, Bechet's disease, hyperostosis, metastatic bone disease, immobilization-induced osteopenia or osteoporosis, or glucocorticoid-induced osteopenia or osteoporosis, osteoporosis pseudoglioma syndrome, idiopathic juvenile osteoporosis, for the improvement of fracture healing after traumatic or atraumatic fracture, and for the maintenance or increase of energy level, for building up or strengthening muscle tissues and for weight gain, the kit comprising at least a first and a second component, the first component comprising at least one of the following: i) strontium alpha-ketoglutarate, ii) a further strontium containing compound, iii) a further alpha-ketoglutarate containing compound, iv) a calcium containing compound, v) a further active substance, and one or more second components comprising at least one of the following: i) strontium alpha-ketoglutarate, ii) a further strontium containing compound, iii) a further alpha-ketoglutarate containing compound, iv) a calcium containing compound, v) a further active substance, such as, e.g. vitamin D, with the proviso that the first and the one or more second components are not identical.

The strontium- and alpha-ketoglutarate-containing compounds for use in the kits may be selected from the compounds mentioned above.

Strontium/Glutamate Compositions

As mentioned above alpha-ketoglutarate may be converted to the amino acid glutamate, which is a precursor of glutamine, arginine and proline, the latter being an important component of collagen. Thus, the amino acid glutamate is also considered an important agent in the treatment of cartilage and/or bone condition, and the administration of strontium and glutamate together in the form of a strontium glutamate salt is believed to have prophylactic and/or therapeutic value in that one or more of the beneficial effects mentioned above for strontium and alpha-ketoglutarate can be obtained. In addition glutamate may directly affect specific glutamate receptors present on the resorbing osteoclasts, and thus affect the metabolic activity and bone resorbing action of these cells.

Thus, the present invention relates to the use of a strontium glutamate salt of the formula II:

$$(^{-}OOC—C(NH_3^+)H—CH_2—CH_2—COO^{-})_2 Sr^{2+} \qquad (II)$$

as a medicine as well as to a method for the preparation of strontium glutamate. As disclosed in Examples 4-7 the invention also relates to specific methods of producing the strontium salt of the invention involving synthesis at temperatures above 100° C.

The invention further relates to use of strontium glutamate for the preparation of a pharmaceutical composition for the treatment and/or prophylaxis of a cartilage and/or bone disease and/or conditions resulting in a dysregulation of cartilage and/or bone metabolism in a mammal, such as, e.g., a human female or male adult, adolescent or a child, such as described herein before.

For the treatment and/or prophylaxis of different cartilage and/or bone diseases, the possibility of administering various amounts of strontium and glutamate respectively may be desired. The amount of strontium and glutamate in a pharmaceutical composition according to the invention may be adjusted by adding an additional amount of strontium in the form of a strontium-containing compound and/or an additional amount of glutamate in the form of a glutamate-containing compound to the composition.

All the strontium salts of organic or inorganic acids mentioned above and salts of glutamic acid may be used to adjust the amount of strontium and glutamate in a pharmaceutical composition comprising strontium glutamate, and may also be used in a composition according to the invention comprising a strontium-containing compound and a glutamate-containing as described above. The salts may be in hydrate, anhydrous, solvate, polymorphous, amorphous, crystalline, microcrystalline or polymeric form.

The organic and inorganic acids for making strontium salts may be selected from any of the groups described above.

Below follows examples of salts of glutamic and aspartic acid, which may be used to adjust the amount of glutamate and/or aspartate compound in a pharmaceutical composition comprising strontium glutamate and/or strontium aspartate, or in a pharmaceutical composition comprising a strontium-containing compound and a glutamate compound as described above.

The salt may be a salt of an alkali metal, a mixed salt of alkali metals, an alkaline earth metal, or mixtures thereof.

Specific examples of salts for use according to the invention may be sodium glutamate, potassium glutamate, lithium glutamate, magnesium glutamate, calcium glutamate. The salt may also be a salt of an amine or an amino acid or an ammonium salt or mixtures thereof. The amine may be selected from methyl amine, ethyl amine, propyl amine, iso-propyl amine and butyl amine, and the amino acid may be selected from arginine, ornithine, lysine and histidine.

The invention also relates to a method for the treatment and/or prophylaxis of a cartilage and/or bone disease and/or conditions resulting in a dysregulation of cartilage and/or bone metabolism in a mammal, such as, e.g., a human female or male adult, adolescent or a child, such as the ones mentioned above, for the maintenance or increase of energy level, for building up or strengthening muscle tissues and for weight gain, the method comprising administering to a subject in need thereof an amount of the strontium glutamate salt according to the invention.

In the latter method wherein strontium glutamate is administered, the salt may be administered in a dose corresponding to from about 0.2 to about 28 g daily calculated as anhydrous salt. More specifically, the salt may be administered in a dose corresponding about 0.3 to about 25 g daily such as, e.g., from about 0.7 to about 20 g daily, from about 1 to about 17 g daily or from about 1.2 to about 16 g or from about 2 to about 6 g daily calculated as anhydrous salt.

As described above, depending on the condition the subject is having, there might be a need for increasing and/or adjusting the amounts of strontium and glutamate. Thus, the invention further relates to a method, which comprises the administration of an additional dose of a strontium-containing compound together with strontium glutamate. The invention also relates to a method, which comprises administration of an additional dose of a glutamate-containing compound. The strontium-containing and glutamate-containing compounds may be selected from the compounds described above.

For the method wherein a strontium glutamate salt is administered, optionally together with an additional amount of strontium and/or L- or D-glutamate, and the method wherein one or more strontium-containing compounds and one or more L- or D-glutamate-containing compounds are administered, the weight ratio between the total daily dose of strontium and the total daily dose of glutamate is from about 0.01 to about 4, such as, e.g., from about 0.01 to about 4, from about 0.01 to about 2, from about 0.01 to about 1, from about 0.01 to about 0.6, from about 0.03 to about 4, from about 0.03 to about 2, from about 0.03 to about 1, from about 0.1 to about 2, from about 0.1 to about 1, from about 0.15 to about 0.5, from about 0.2 to about 2, from about 0.3 to about 2 or from about 0.4 to about 2.

As mentioned above, the daily dose of strontium may be at least about 0.01 g, such as, e.g., at least about 0.025 g, at least about 0.050 g, at least about 0.075 g, at least about 0.1 g, at least about 0.2 g, at least about 0.3 g, at least about 0.4 g or at least about 0.5 g or from about 0.01 g to about 2 g such as, e.g., from about 0.1 g to about 2 g, from about 0.3 g to about 2 g or from about 0.3 g to about 1 g.

The daily dose of L- and/or D-glutamate may be at least about 0.5 g, such as, e.g., at least about 1.0 g, at least about 1.5 g, at least about 2.0 g, at least about 2.5 g, at least about 3.0 g, at least about 4 g, at least about 5 g or from about 0.5 g to about 10 g, from about 0.5 g to 7 g, from about 2 g to about 10 g or from about 2 g to about 7 g.

The invention also relates to a method wherein the strontium component and the glutamate component are administered in the form of a pharmaceutical composition as described above.

In a method according to the invention the strontium component and the glutamate component may be administered in single mixture formulations or simultaneously in separate, co-administered formulations. Strontium and glutamate may be in the form of strontium glutamate, optionally with an additional amount of a strontium-containing compound and/or a glutarnate-containing compound. The additional component may be added to the strontium glutamate in the same formulation, or may be in a separate formulation intended for simultaneous or sequential administration.

Strontium and glutamate may also be combined as a mixture of one or more strontium-containing compounds and one or more glutamate-containing compounds in the same formulation, or in separate forms intended for simultaneous administration. When two or more separate formulations are being co-administered, each formulation, especially those for use by oral route, may be color-coded or otherwise easily identifiably labeled in order to avoid confusion by the subject or physician.

As described above one or more active substances may be added to a pharmaceutical composition according to the invention or administered as part of the same treatment as the administration of strontium and glutamate.

Strontium/Aspartate Compositions

Aspartate is an amino acid structurally related to glutamate, which can also form pharmaceutically relevant salts in complex with strontium. As all amino acids except glycine aspartate exist in an L-form, which is the physiologically relevant form used in all biological systems and the 'mirror image' enantiomer denoted D-Aspartate. D-aspartate may directly or indirectly affect metabolism of bone and/or cartilage via binding to the N-methyl-D-aspartate (NMDA) receptor, which has been found on metabolically active osteoclasts and may also be present on chondrocytes of articular cartilage. Thus the present invention also relates to a strontium aspartate salt (in D- or L-form or a mixture thereof) of the formula (III)

  (III)

as a medicine as well as to a method for the preparation of strontium aspartate. As disclosed in Examples 4-7 the invention also relates to specific methods of producing the strontium salt of the invention involving synthesis at temperatures above 100° C.

The invention further relates to use of strontium aspartate for the preparation of a pharmaceutical composition for the treatment and/or prophylaxis of a cartilage and/or bone disease and/or conditions resulting in a dysregulation of cartilage and/or bone metabolism in a mammal, such as, e.g., a human female or male adult, adolescent or a child, such as, e.g., male and female osteoporosis, osteoarthritis, osteopetrosis, osteopenia and Paget's disease, hypercalcemia of malignancy, periodontal disease, hyperparathyroidism, periarticular erosions in rheumatoid arthritis, osteodystrophy, myositis ossificans, Bechterew's disease, malignant hypercalcemia, osteolytic lesions produced by bone metastasis, bone pain due to bone metastasis, bone loss due to sex steroid hormone deficiency, bone abnormalities due to steroid hormone treatment, bone abnormalities caused by cancer therapeutics, osteomalacia, Bechet's disease, hyperostosis, metastatic bone disease, immobilization-induced osteopenia or osteoporosis, or glucocorticoid-induced osteopenia or osteoporosis, osteoporosis pseudoglioma syndrome, idiopathic juvenile osteoporosis, for the improvement of fracture healing after traumatic or atraumatic fracture, and for the maintenance or increase of energy level, for building up or strengthening muscle tissues and for weight gain. The pharmaceutical composition may further comprise one or more physiologically acceptable excipients.

The invention also relates to a kit for use in the treatment and/or prophylaxis of a cartilage and/or bone disease and/or conditions resulting in a dysregulation of cartilage and/or bone metabolism in a mammal, such as, e.g., a human female or male adult, adolescent or a child, such as, e.g., osteoporosis, osteoarthritis, osteopetrosis, osteopenia and Paget's disease, hypercalcemia of malignancy, periodontal disease, hyperparathyroidism, periarticular erosions in rheumatoid arthritis, osteodystrophy, myositis ossificans, Bechterew's disease, malignant hypercalcemia, osteolytic lesions produced by bone metastasis, bone pain due to bone metastasis, bone loss due to sex steroid hormone deficiency, bone abnormalities due to steroid hormone treatment, bone abnormalities caused by cancer therapeutics, osteomalacia, Bechet's disease, hyperostosis, metastatic bone disease, immobilization-induced osteopenia or osteoporosis, or glucocorticoid-induced osteopenia or osteoporosis, osteoporosis pseudoglioma syndrome, idiopathic juvenile osteoporosis, for the improvement of fracture healing after traumatic or atraumatic fracture, and for the maintenance or increase of energy level, for building up or strengthening muscle tissues and for weight gain, the kit comprising at least a first and a second component, the first component comprising strontium glutamate and one or more second components comprising at least one of the following: i) a further strontium containing compound, ii) a further glutamate containing compound, iii) a calcium containing compound, iv) vitamin D, v) parathyroid hormone, vi) a further active substance.

The invention also relates to a kit for use in the treatment and/or prophylaxis of a cartilage and/or bone disease and/or conditions resulting in a dysregulation of cartilage and/or bone metabolism in a mammal, such as, e.g., a human female or male adult, adolescent or a child, such as, e.g., osteoporosis, osteoarthritis, osteopetrosis, osteopenia and Paget's disease, hypercalcemia of malignancy, periodontal disease, hyperparathyroidism, periarticular erosions in rheumatoid arthritis, osteodystrophy, myositis ossificans, Bechterew's disease, malignant hypercalcemia, osteolytic lesions produced by bone metastasis, bone pain due to bone metastasis, bone loss due to sex steroid hormone deficiency, bone abnormalities due to steroid hormone treatment, bone abnormalities caused by cancer therapeutics, osteomalacia, Bechet's disease, hyperostosis, metastatic bone disease, immobilization-induced osteopenia or osteoporosis, or glucocorticoid-induced osteopenia or osteoporosis, osteoporosis pseudoglioma syndrome, idiopathic juvenile osteoporosis, for the improvement of fracture healing after traumatic or atraumatic fracture, and for the maintenance or increase of energy level, for building up or strengthening muscle tissues and for weight gain, the kit comprising at least a first and a second component, the first component comprising at least one of the following: i) strontium alpha-ketoglutarate, ii) a further strontium containing compound, iii) a further alpha-ketoglutarate containing compound, iv) a calcium containing compound, v) vitamin D, vi) parathyroid hormone, vii) a further active substance, and one or more second components comprising at least one of the following: i) strontium glutamate, ii) a further strontium containing compound, iii) a further glutamate containing compound, iv) a calcium containing compound, v) vitamin D, vi) parathyroid hormone, vii) a further active substance, with the proviso that the first and the one or more second components are not identical.

Pharmaceutical Compositions

The pharmaceutical compositions according to the invention normally comprise the specific compounds together with one or more physiologically acceptable excipients, i.e. a therapeutically inert substance or carrier.

The carrier may take a wide variety of forms depending on the desired dosage form and administration route.

The pharmaceutically acceptable excipients may be e.g. fillers, binders, disintegrants, diluents, glidants, solvents, emulsifying agents, suspending agents, stabilizers, enhancers, flavors, colors, pH adjusting agents, retarding agents, wetting agents, surface active agents, preservatives, antioxidants etc. Details can be found in pharmaceutical handbooks such as, e.g., Remington's Pharmaceutical Science or Pharmaceutical Excipient Handbook.

Above are mentioned specific examples of the amounts of compounds administered. However, it will be understood that the amount of the compounds actually administered will be determined by a physician in light of the relevant circumstances including the condition to be treated, the choice of compounds to be administered, the age, weight, and response of the individual patient, the severity of the patient's symptoms and the chosen route of administration. While the present compounds are preferably administered orally, the compounds may also be administered by any other suitable route.

The pharmaceutical composition comprising a compound according to the invention may be in the form of a solid, semi-solid or fluid composition.

The solid composition may be in the form of tablets such as, e.g. conventional tablets, effervescent tablets, coated tablets, melt tablets or sublingual tablets, pellets, powders, granules, granulates, particulate material, solid dispersions or solid solutions.

In one embodiment of the invention, the pharmaceutical composition may be in the form of a tablet. The tablet may be coated with a coating that enables release of at least part of the salt in the proximal part of the small intestine, such as e.g. the duodenum and/or the proximal jejunum, such as at least 50% w/w, at least 60% w/w, at least 65% w/w, at least 70% w/w, at least 80% w/w or at least 90% w/w of the total amount of the salt contained in the tablet.

The tablet may have a shape that makes it easy and convenient for a patient to swallow. The tablet may thus e.g. have a rounded or a rod-like shape without any sharp edges. Furthermore, the tablet may be designed to be divided in two or more parts.

A semi-solid form of the composition may be a paste, a gel or a hydrogel.

The fluid form of the composition may be a solution, an emulsion including nano-emulsions, a suspension, a dispersion, a liposomal composition, a spray, a mixture, a syrup or an elixir.

Other suitable dosages forms of the pharmaceutical compositions according to the invention may be capsules, sachets, troches, devices etc.

The pharmaceutical compositions may be prepared by any of the methods well known to a person skilled in pharmaceutical formulation.

Other Aspects Of The Invention

As mentioned above, use of a composition or kit according to the invention may lead to improved fracture healing after traumatic or atraumatic fracture, where the fracture e.g. may be one of the following traumatic or atraumatic fractures: fracture to the distal radius, such as e.g. a Colle's fracture or a Smiths fracture, a fracture of the femur, such as e.g. the proximal femur, such as e.g. a cervical fracture, a trochanteric fracture or a subtrochanteric fracture.

The improved fracture healing may be defined in terms of a reduction of the time a patient will require a plaster, reduction of the time to healing as defined on a X-ray, reduction in the time to fracture stability, improvement of callus formation as viewed by X-ray, reduction in time before appearance of callus formation as viewed by X-ray and/or reduction in time for regaining full or near-full mobility or physical activity level.

Other embodiments of the invention appear from the appended claims. The details and particulars described above and relating to the compounds and compositions according to the invention apply mutatis mutandis to the other aspects of the invention.

The invention is further illustrated in the examples that are not intended to limit the invention in any way.

EXAMPLES

Example 1

General Method for Preparation of Crystalline Salts of Strontium by Precipitation from Dissolved Strontium Chloride and Dissolved Sodium Salts of the Appropriate Carboxylic Anions In a glass-beaker of 100 mL volume, 5 g of the sodium salt of the carboxylic acid was dissolved in a small volume of water that was slightly heated at temperatures not greater than 30-50° C. The final volume was 25-50 mL. In another beaker 10 g of $SrCl_2$ ($SrCl_2$ hexahydrate, Sigma-Aldrich 43,966-5) was dissolved in 100 mL of water. This latter solution was slowly decanted into the first solution of the dissolved sodium salt. The transfer continued until an initial cloudiness was observed, which resulted in a total volume of 50-100 mL. The solution was allowed to rest at room temperature (22-24° C.) for several days until significant amounts of crystallized precipitate of the organic strontium salt appeared.

The reaction that proceeds is exemplified by the reaction between strontium ions and sodium fumarate (reaction schemes (a) and (b)):

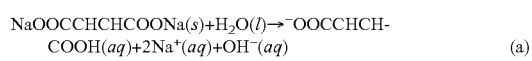

(a)

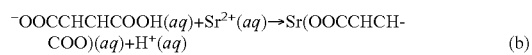

(b)

In order to accelerate the crystallization, we have found that addition of small volumes of ethanol, such as from 5-10 vol/vol % to 50-60% vol/vol induces a significant acceleration of the precipitation of the desired strontium salt. Addition of ethanol is of special importance in the synthesis of strontium salts with solubility exceeding 2 g/l at room temperature (22-24° C.), and will thus provide a substantial benefit for the synthesis of strontium salts of L-aspartate, L-glutamate and lactate. In order to reach the required product within a short period, it was essential to observe an initial crystallization or an initial dimness in the solution right from the first stage.

After the precipitation, the solution was filtered on a Büchner funnel using a suction flask and the crystals were flushed in small volumes of ethanol. Crystals of some of the salts were very soluble, so in order to improve the yield of crystals, the solution was allowed to rest longer, such as at least 30-60 min. Repeated crystallisation resulted in yields of approx. 50%. Strontium salts of L-aspartate and of lactate were very soluble, with solubility exceeding 25 g/l in water at room temperature.

The lactate and L-glutamate salts of strontium were precipitated from solutions with an excess of strontium chloride and large crystals of the lactate salt were achieved by slow evaporation of the solvent.

Example 2

General Method for Preparation of Crystalline Salts by Neutralisation of Carboxylic Acids with Strontium Hydroxide A small amount of the organic acid proper (0.75-3 g, see table below) was dissolved in water by heating to temperatures between 30° C.-50° C. Then, strontium hydroxide (Sigma Aldrich, $Sr(OH)_2 \cdot 8H_2O$, MW 265.71, CAS no. 1311-10-0, approx. 10 g/L) was slowly added. Then, a magnetic stirring rod was added and the stirring and gentle heating (i.e. 30-50° C.) of the suspension was started. After some time, the solution clarifies and all the solid material dissolves. The heating is maintained, and after three hours of incubation, the solution is filtered while hot on a Büchner funnel. Very small amounts of impurities were left in the filter.

The filtrate was subsequently allowed to cool at room temperature overnight, which resulted in growth of fine-powdered crystals of the desired strontium salt. Further purifications of the salts can be performed by repeated re-crystallizations (Table 6).

TABLE 6

Amounts of start reagent used for organic strontium salt synthesis and recoveries in the synthesis of eight specific organic strontium salts following the general reaction pathway with free-acid forms of the anion, and strontium hydroxide

| Strontium salt of (free acid used): | $Sr(OH)_2 \cdot 8H_2O$ | Free acid | Amount obtained | Recovery* | Melting Temp. | Solubility | Crystal structure |
|---|---|---|---|---|---|---|---|
| Fumarate[1] | 2.044 g | 1.140 g | 0.999 g | 99% | >380° C. | Yes | No |
| α-ketoglutarate[2] | 2.017 g | 1.441 g | 0.828 g | 72% | >380° C. | Yes | No |
| succinate | 2.098 g | 1.177 g | 0.958 g | 92% | 230° C. | Yes | Yes |
| L-Ascorbate[3] | 2.094 g | 1.805 g | 2.005 g | 15% | >380° C. | Yes | No |
| L-Glutamate | 2.017 g | 1.453 g | 0.175 g | 15% | >380° C. | Yes | Yes |
| Citrate | 2.057 g | 1.918 g | 1.123 g | 48% | >380° C. | Yes | Yes |
| D-Aspartate | 2.190 g | 1.316 g | 0.167 g | 14% | >380° C. | No | No |
| Tartrate | 2.070 g | 1.502 g | 2.005 g | 129% | >380° C. | Yes | Yes |

Notes
*Recovery calculated in % of the strontium content in $Sr(OH)_2 \cdot 8H_2O$.
[1]Fumaric acid is insoluble in water, and ethanol is added to the suspension until complete solubilization is achieved. The synthesis is continued with this material.
[2]The strontium-AKG salts has a slight brownish appearance and a melting temperature %
[3]In addition to the indicated amounts of strontium hydroxides and L-ascorbate an additional 4.087 g $SrCl_2 \cdot 6H_2O$ solubilized in water is added to the reaction mixture.

Example 3

Determinations of Solubility of Organic Strontium Salts

Synthesis of Strontium Salts

The great majority of strontium salts could be obtained by reacting the sodium salt of the organic acid with strontium chloride following the general synthesis method described in Example 1. However, strontium citrate, strontium tartrate, strontium succinate and strontium a-ketoglutarate for the solubility investigations was obtained by synthesis from the free acid forms of the carboxylic acid and strontium hydroxide as described in Example 2. Strontium glutamate was obtained as described in Example 4, using an incubation temperature of 100° C. and using strontium chloride and L-glutamic acid for the synthesis for obtaining pure and homogeneous hexahydrate crystals of strontium glutamate. As described in Example 4 the strontium glutamate salt obtained by this method is distinct from a previously described form of crystalline strontium L-glutamate. Detailed investigations of solubility were carried with the strontium salts listed in Table 7:

TABLE 7

Overview of strontium salts used in investigation of solubility. MW indicates the molecular weight of the homogeneous crystalline form of the salt with the indicated amount of crystal water and % Sr gives the molar percentage that strontium constitutes of this crystalline form

| Strontium salt | MW | % Sr |
|---|---|---|
| Sr-ranelate (*7H$_2$O) | 639.6 | 27.4 |
| SrCl$_2$ (*6H$_2$O) | 266.6 | 32.9 |
| Sr-fumarate (*6H$_2$O) | 309.7 | 28.3 |
| Sr-L-glutamate (*6H$_2$O) | 340.7 | 25.7 |
| Sr-α-ketoglutarate (*6H$_2$O) | 339.7 | 25.8 |
| Sr-aspartate (*3H$_2$O) | 272.7 | 32.1 |
| Sr-succinate (*6H$_2$O) | 311.7 | 28.1 |
| Sr-ascorbate (*6H$_2$O) | 545.8 | 16.1 |
| Sr-malenate (*6H$_2$O) | 309.7 | 28.3 |
| Sr-malonate (anhydrous) | 189.7 | 46.2 |
| Sr-pyruvate (*6H$_2$O) | 369.7 | 23.7 |
| Sr-tartrate (*6H$_2$O) | 343.7 | 25.5 |
| Sr-citrate (*6H$_2$O) | 749.1 | 35.1 |

The solubility of the organic carboxylic acid strontium salts, were measured in water. The solubility of these salts was also measured as a function of temperature. This was performed by incubating the saturated solutions of the salts in temperature-controlled incubators. Furthermore the solubility of the salts was studied in pure distilled water as well as a 0.05 M ammonium carbonate buffered solutions, with a physiological pH of 7.5.

The buffered solutions were immersed into a bath of water temperature controlled at either room temperature (22-24° C.), at 30° C. or at 40° C. The test tubes were stirred and the solutions were subsequently incubated in an incubator with constant temperature for 24 hours. In order to eliminate any reminiscent strontium chloride influence on the determination of solubility, all the precipitate was collected at the bottom of the test tubes and the solutions above the precipitate were carefully removed and substituted by fresh solutions. After substitution of the solutions, the test tubes were stirred again and allowed to rest for another 24 hours. From these solutions, the dissolved proportions of the strontium salt were collected in volumes of 1 mL at the specified temperature. The solutions were diluted to 50 mL before analysis by Flame Atomic Absorption Spectrometry (F-AAS). Before subsequent series of sampling, the solutions were equilibrated at the next temperature for 24 hours.

Analysis of Strontium by Flame Atomic Absorption Spectrometry F-AAS

Two methods were used for quantification of strontium in solutions: Flame Atomic Absorption Spectrometry (F-AAS), and the more sensitive inductively-coupled-plasma-mass spectrometry (ICP-MS). For most investigations, the F-AAS method had sufficient sensitivity.

Some of the very soluble strontium salts were further diluted before analysis by F-AAS. The measurements were performed by using a Perkin-Elmer 2100 equipped with a hydrogen lamp for correction of the background signal. Strontium was measured at a slit with of 0.2 nm, the wavelength was 460.8 nm operated at an energy of 58 and a current of 8 mA.

Temperature and pH Influence on Organic Strontium Salt Solubility

For the majority of the organic strontium salts listed in Table 2, temperature changes in the interval from 20-40° C. had only little influence on solubility (Table 3). However, for strontium L-glutamate a significant influence of temperature on solubility was observed in the range between 20° C. and 40° C. The solubility of this salt increased more than threefold in the investigated interval in contrast to most other salts.

It is noted, that the solubility under physiological conditions (37° C.), is of relevance for the pharmaceutical use of the substances, and thus the surprising increase in strontium glutamate solubility at higher temperature may have great potential therapeutic implications.

The solubility of the strontium salts in an ammonium carbonate buffered solution of pH 7.5 was generally higher than the solubility determined in pure water (Table 8). However, there were some notable exceptions, such as strontium maleate, which had decreased solubility in the buffered solution. Accordingly, it was found most relevant to compare the solubility of the strontium salts by comparing the values obtained in water, as shown in Table 8.

Relative Solubility

The water-solubilities of the organic strontium salts at room temperature and at 40° C., are listed in Table 8. The strontium salts of L-aspartate and of lactate had solubilities exceeding 50 g/l hampering exact determination of solubility with the employed experimental procedures.

The results correspond to the observations during the synthesis experiments where the citrate, the fumarate and the tartrate precipitated instantly when synthesized by the production procedures described in Examples 1 and 2. This is indicative of a poor solubility of these strontium salts, as apparent by the lower solubility of these salts compared to the other organic strontium salts at both 22° C. and 40° C.

The glutamate salt showed a higher solubility than the other salts, especially at a temperature of 40° C. During the synthesis of this salt, it was necessary to add alcohol to the solution, to initiate crystal growth, indicative of relatively high water solubility. The other studied strontium salts only precipitated after evaporation of the solvent for a few days at room temperature, but addition of alcohol was not required to initiate crystal formation and precipitation.

TABLE 8

Relative solubility in water buffered solutions at pH 7.5 at 40° C. and room temperature (22-24° C.) of the investigated Strontium-salts, as determined by F-AAS.

| STRONTIUM SALT | SOLUBILITY AT ROOM TEMPERATURE (22-24° C.) (mg/L) | | SOLUBILITY AT 40° C. (mg/L) | |
|---|---|---|---|---|
| Anion | In water | pH 7.5 | In water | pH 7.5 |
| Malonate** | 1474 | 2816 | 1441 | 2127 |
| L-glutamate** | 2111 | 3022 | 7093 | 7195 |
| L-aspartate** | 4200 | | 7900 | |
| Pyruvate* | 2204 | 1946 | 1929 | 1829 |
| α-ketogluterate** | 1316 | 2252 | 3534 | 3809 |
| Fumerate** | 571 | 1215 | 444 | 977 |
| Maleate** | 3002 | 1680 | 2527 | 1457 |
| Tartrate** | 883 | 1831 | 1028 | 1400 |
| Ranelate**** | 760 | 890 | 1450 | 1970 |
| Succinate** | 1137 | 926 | 1116 | 2233 |
| Citrate*** | 107 | 388 | 147 | 430 |

*Mono-carboxylic acid
**Di-carboxylic acid
***Tri-carboxylic acid
****Quattro-carboxylic acid Example 4

Preparation of Strontium Glutamate Hexahydrate by Synthesis at 100° C.

Initially, a suspension of glutamic acid (white colored) is prepared by adding 100 mL of millipore water to 14.703 g (0.1 moles) of solid L-glutamic acid (Sigma Aldrich, C5H9NO4, MW 187.14 g/mole, CAS no. 14247-2, lot. no. 426560/1, filling code 43003336) in a 250 mL beaker. To this suspension was added 26.66 g (0.1 moles) of solid $SrCl_2$ ($SrCl_2$ hexahydrate, Sigma-Aldrich 43, 966-5, MW 266.6). Then, a magnetic stirring rod was added and the stirring and heating was started to the point of boiling of the suspension. The final suspension is also white colored and the stirring is sustained by maintaining a medium rotation rate of the stirring apparatus. In order to prevent carbon dioxide from entering the solution, the beaker was covered by a covering glass.

After some minutes of boiling and stirring, the solution clarified and all the solid material dissolved. The boiling was maintained, and additional water was added when required, as to replace the water lost by boiling. After three hours of boiling, the solution was filtered while boiling on a Büchner funnel. Very small amounts of impurities were left in the filter. The filtrate was subsequently allowed to cool to room temperature, which resulted in growth of fine-powdered crystals of strontium glutamate hexahydrate. Precipitation of the final product progressed in the filtrate within an hour. The product was filtered and dried at 110° C. in an oven for ½ hour followed by drying 12 hours in a dessicator over silica orange. Before analysis by x-ray crystallography and by FAAS, the salts were ground to fine powder by a mortar.

Figure 4A:
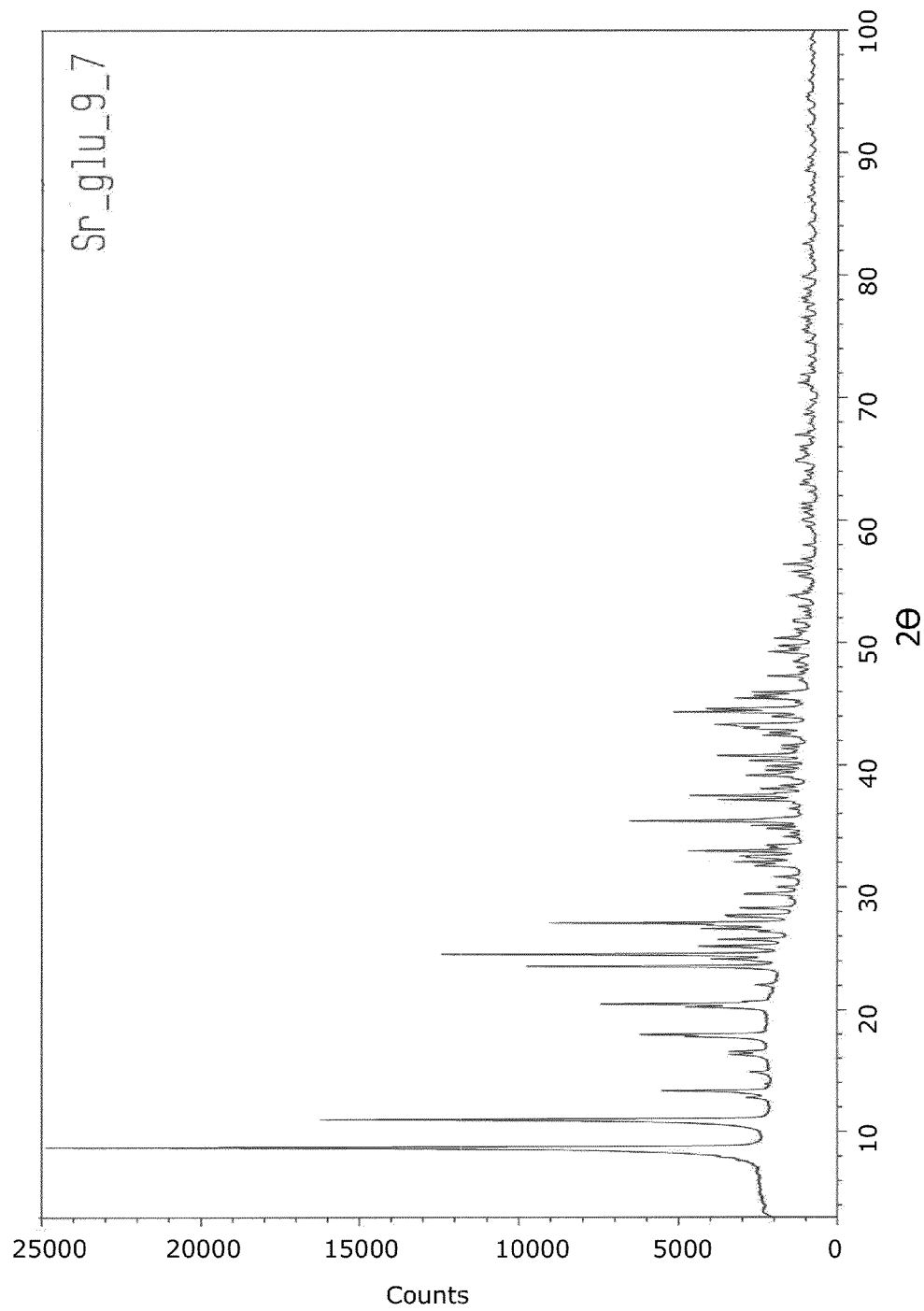
FIG. 4A is a diffractogram of the x-ray analysis for strontium glutamate hexahydrate, as synthesized by strontium hydroxide and L-glutamic acid at high temperature but using the reaction conditions described in Example 2.
Figure 4B:
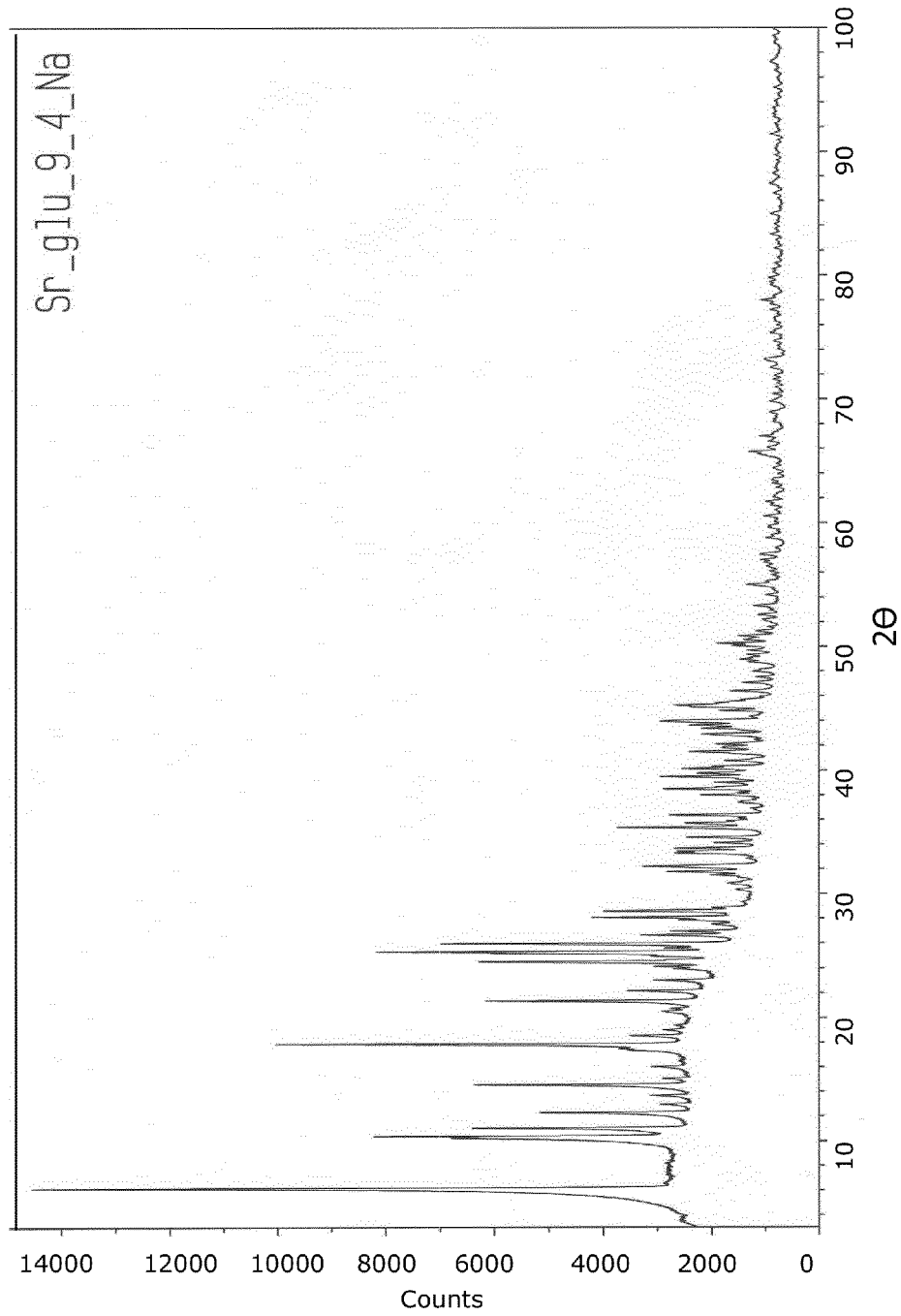
FIG. 4B is a diffractogram of the x-ray analysis for strontium glutamate hexahydrate, as synthesized by strontium hydroxide and L-glutamic acid as described in Example 4.

The X-ray crystallographic analysis (FIGS. 4A and 4B) revealed that the synthesized strontium glutamate salt was distinct from the previously described strontium L-glutamate hexahydrate salt described in FIGS. 1 and 2 and Tables 2 and 3.

This salt and the resulting diffractogram corresponds to the strontium L-glutamate hexahydrate salt previously described (H. Schmidbaur, I. Bach, L. Wilkinson & G. Müller (1989), Chem Ber. 122; 1433-1438) and further detailed in FIGS. 1 and 2 and Tables 2 and 3. The lower trace shows a strontium glutamate hexahydrate salt synthesized from strontium chloride and L-glutamic acid as disclosed in the present example.

The total yield of strontium glutamate hexahydrate was approximately 92% before recrystallisation, and the majority of impurities consisted of reminisces of the reagents and of strontium carbonate. This yield is significantly higher than the yield obtained by synthesis under conventional conditions where only 15% was obtained (please see Example 2). Thus, the high temperature synthesis method as disclosed in this patent provides a significant gain in yield and a reduction in synthesis time, while resulting in a strontium glutamate salt of higher purity. Furthermore, the strontium glutamate obtained by this synthesis procedure was distinct from the strontium L-glutamate hexahydrate salt previously described (H. Schmidbaur, I. Bach, L. Wilkinson & G. Müller (1989), Chem Ber. 122; 1433-1438). The strontium glutamate hexahydrate described previously in the literature by Schmidbaur et al was reported to have very low solubility (0.023 g/l), whereas the strontium glutamate salt prepared by the method disclosed in the present example had a solubility above 2 g/l. This later parameter is very important for potential medical use of the strontium salt as described in the present invention.

Further improvements of the synthesis may include degassing by nitrogen or by argon of the water and of all aqueous solutions, which prevents contact to carbon dioxide that eventually may lead to formation of impurities of strontium carbonate. It follows that a person skilled in the art will easily be able to adapt the procedure to proceed under an inert gas atmosphere.

Example 5

Preparation of Strontium Aspartate Trihydrate by Synthesis at 100° C.

Initially, a suspension of aspartic acid (white colored) is prepared by adding 100 mL of millipore water to 13.311 g (0.1 moles) of solid L-aspartic acid (Fluka, $C_5H_9NO_4$, MW 133.11 g/mole, CAS no. 56-84-8, lot. no. 432866/1, filling code 52603495) in a 250 mL beaker. To this suspension was added 26.571 g (0.1 moles) of solid strontium hydroxide (Sigma Aldrich, $Sr(OH)_2 * 8H_2O$, MW 265.71, CAS no. 1311-10-0). Then, a magnetic stirring rod was added and the stirring and heating was started to the point of boiling of the suspension. The final suspension is also white colored and the stirring is sustained by maintaining a medium rotation rate of the stirring apparatus. In order to prevent carbon dioxide from entering the solution, the beaker was covered by a covering glass.

After some minutes of boiling and stirring, the solution clarified and all the solid material dissolved. The boiling was maintained, and additional water was added when required, as to replace the water lost by boiling. After three hours of boiling, the solution was filtered while boiling on a Büchner funnel. Very small amounts of impurities were left in the filter. The filtrate was subsequently allowed to cool to room temperature, which resulted in growth of fine-powdered crystals of strontium aspartate trihydrate. Precipitation of the final product progressed in the filtrate within an hour. The product was filtered and dried at 110° C. in an oven for ½ hour followed by drying 12 hours in a dessicator over silica orange. Before analysis by x-ray crystallography and by FAAS, the salts were ground to fine powder by a mortar.

The total yield of strontium aspartate trihydrate was approximately 98% before recrystallisation, and the majority of impurities consisted of reminisces of the reagents and of strontium carbonate. This yield is significantly higher than the yield obtained by synthesis under conventional conditions where only 14% was obtained (please see Example 2). Thus the high temperature synthesis method as disclosed in this patent provides a significant gain in yield and a reduction in synthesis time, while resulting In a strontium aspartate salt of higher purity. The product was unambiguously identified as strontium aspartate trihydrate by x-ray crystallography and comparing the data to results of the Cambridge Crystallographic Database and information from H. Schmidbaur, P. Mikulcik & G. Müller (1990), Chem Ber. 123; 1599-1602 as depicted in FIG. 3 and Tables 4 and 5 herein.

Further improvements of the synthesis may include degassing by nitrogen or by argon of the water and of all aqueous solutions, which prevents contact to carbon dioxide that eventually may lead to formation of impurities of strontium carbonate. It follows that a person skilled in the art will easily be able to adapt the procedure to proceed under an inert gas atmosphere.

Example 6

Preparation of Strontium Malonate by Synthesis at 100° C.

Initially, a suspension of malonic acid (white colored) is prepared by adding 100 mL of millipore water to 10.406 g (0.1 moles) of solid malonic acid (Fluka, MW 104.06 g/mole, CAS no. 141-82-2, lot. no. 449503/1, filling code 44903076) in a 250 mL beaker. To this suspension was added 26.571 g (0.1 moles) of solid strontium hydroxide (Sigma Aldrich, $Sr(OH)_2 * 8H_2O$, MW 265.71, CAS no. 1311-10-0). Then, a magnetic stirring rod was added and the stirring and heating was started to the point of boiling of the suspension. The final suspension is also white colored and the stirring was sustained by maintaining a medium rotation rate of the stirring apparatus. In order to prevent carbon dioxide from entering the solution, the beaker was covered by a covering glass.

After some minutes of boiling and stirring, the solution clarified and all the solid material dissolved. The boiling was maintained, and additional water was added when required, as to replace the water lost by boiling. After three hours of boiling, the solution was filtered while boiling on a Büchner funnel. Very small amounts of impurities were left in the filter. The filtrate was subsequently allowed to cool to room temperature, which resulted in growth of fine-powdered crystals of strontium malonate. Precipitation of the final product progressed rapidly during filtration and the majority of the product was found in the filter (unheated). Only in rare instants, the precipitation progressed in the filtrate. The product was filtered and dried at 110° C. in an oven for ½ hour followed by drying 12 hours in a dessicator over silica orange. Before analysis by x-ray crystallography and by FAAS, the salts were ground to fine powder by a mortar.

The total yield of strontium malonate was approximately 98% before recrystallisation, and the majority of impurities consisted of reminisces of the reagents and of strontium carbonate. The product was unambiguously identified as strontium malonate by x-ray crystallography and comparing the data to results of the Cambridge Crystallographic Database.

Further improvements of the synthesis may include degassing by nitrogen or by argon of the water and of all aqueous solutions, which prevents contact to carbon dioxide that eventually may lead to formation of impurities of strontium carbonate. It follows that a person skilled in the art will easily be able to adapt the procedure to proceed under an inert gas atmosphere.

Example 7

Methods of Manufacture of Water Soluble Strontium Salts of Dicarboxylic Acids Using Temperatures Above 100° C.

According to methods developed previously and described in Examples 2-6, synthesis of strontium salts of dicarboxylic organic acids, and especially strontium salts of amino acids can be difficult to produce in larger scale (i.e. >1 kg) due to low yields and difficulties in separating the desired reaction products from contaminants. Strontium salts of carbonate are of special concern as they will form as impurities when the reaction is occurring in atmospheric air containing normal levels of carbon dioxide. We have described in Examples 4-6 that the total yield of the product when strontium salts of dicarboxylic acids are manufactured from the free acid form of the anion, and strontium hydroxide depends on temperature and on time of synthesis. In order for the reaction to reach completion, the mixture of the amino acid proper and strontium hydroxide needs boiling in water for three hours, allowing ample time for strontium in the reaction mixture to react with carbon dioxide in the air. In this example we disclose methods of improving the synthesis further by providing optimized reaction conditions, where temperature is increased above 100° C. in a closed container, and where reaction times are significantly reduced.

The present example provides representative data from the optimization of conditions for synthesis of strontium glutamate in an autoclave system. Strontium glutamate is used as an example, but it the optimizations described in the example is also applicable for the synthesis of other strontium salts, where the exact reaction conditions can be optimized as disclosed in this example. The reaction temperatures must be maintained below the melting point or below the temperature of decomposition of the organic anion moiety of the desired strontium salt. As an example, malonic acid decomposes at 132-134° C., and thus synthesis of strontium malonate must be performed at temperatures below 132° C.

Strontium L-glutamate was used as a model strontium compound in the optimization experiments. The purity of the product was monitored by comparing to crystallographic data and by measuring the content of strontium. Ideally, the content of strontium is 25.7% in strontium L-glutamate hexahydrate, which is the product formed in these experiments. It follows that other soluble strontium salts may be prepared by similar methods with high yield and purity.

EXPERIMENTAL

Preparation of Solutions: a Suspension of Glutamic Acid (White Coloured) is prepared by adding 100 mL of millipore water to 14.703 g (0.1 moles) of solid L-glutamic acid (Sigma Aldrich, $C_5H_9NO_4$, MW 187.14 g/mole, CAS no. 142-47-2, lot. no. 426560/1, filling code 43003336) in a 250 mL beaker. To this suspension was added 22.257 g, 26.571 g or 31.885 (0.08 moles, 0.1 moles or 0.12 moles) of solid strontium hydroxide (Sigma Aldrich, $Sr(OH)_2*8H_2O$, MW 265.71, CAS no. 1311-10-0).

Optimization Experiments

After preparation of the salts, the nine optimization experiments were performed according to the settings of Table 9.

TABLE 9

Parameters and main results of the optimization procedure for synthesis of strontium glutamate. The pressure was monitored but not used in the optimization process. The strontium content (% Sr) was measured by FAAS but not used as quality parameter. The yield (%) was applied as the quality parameter.

| Experiment no. | Autoclave temperature (° C.) | Time of synthesis (min.) | Base-acid ratio | Total volume (ML) | Autoclave pressure (bar) | Yield % | % SR (AAS) |
|---|---|---|---|---|---|---|---|
| 1 | 125 | 15 | 0.8 | 50 | 1.55 | 94 | 25 |
| 2 | 124 | 30 | 1 | 75 | 1 | 112 | 22 |
| 3 | 124 | 60 | 1.2 | 100 | 1.6 | 121 | 21 |
| 4 | 127 | 15 | 0.8 | 100 | 1.2 | 118 | 22 |
| 5 | 132 | 30 | 1 | 50 | 1.55 | 120 | 25 |
| 6 | 132 | 60 | 1.2 | 75 | 1.6 | 50 | 22 |
| 7 | 134 | 15 | 0.8 | 75 | 1.65 | 108 | 24 |
| 8 | 134 | 30 | 1 | 100 | 1.65 | 76 | 14 |
| 9 | 132 | 60 | 1.2 | 50 | 1.65 | 82 | 24 |

Procedure

1. The calculated amount of acid was weighed and transferred to a bluecap autoclave bottle and the Millipore water was added. The bottle was closed and shaken, in order to obtain a finely grained suspension.
2. The calculated amount of strontium hydroxide octahydrate was weighed and added to the acid solution of (1) and the bottle was vigorously vortexed until all coarse lumps of material were transformed into fine-grained powder.
3. The bottle was placed in the autoclave and the temperature was set. While in the autoclave no additional stirring was carried out.
4. At t=100° C. the valve of the autoclave was closed and the timing was started.
5. During the autoclaving were monitored the actual temperature and the actual pressure.
6. After the time of autoclaving ended, the steam was let out, as soon as possible, with due respect to safety precautions.
7. At approx. 110° C. the autoclave was opened and the solution was recovered. Again, the bottle was shook, as to obtain a high degree of mixing.
8. The solution was immediately filtered hot on a Büchner funnel after autoclaving, which left only traces of carbonate in the filter. The product precipitated from the solution during cooling to room temperature.
9. After precipitation, the product was filtered and dried in an oven for ½ an hour at 110° C. Then, it was dried in an dessicator over silica-gel orange. Finally, the product was ground to fine powder in a mortar.
10. The product was weighed after grinding and the total yield calculated.

Preparation of Strontium Malonate According to the Invention

In order to confirm the applicability of the disclosed high temperature synthesis method for other strontium salts than strontium L-glutamate, strontium malonate was prepared. Basically the reaction conditions found for preparation of strontium L-glutamate was employed. A suspension of malonic acid (white coloured) is prepared by adding 100 mL of millipore water to 10.41 g (0.1 moles) of solid malonic acid (FLUKA 63290, MW 104.1) in a 250 mL beaker. To this suspension was added 22.257 g, 26.571 g or 31.885 (0.08 moles, 0.1 moles or 0.12 moles) of solid strontium hydroxide (Sigma Aldrich, $Sr(OH)_2*8H_2O$, MW 265.71, CAS no. 1311-10-0). The reaction procedure described above was followed, and the temperature was maintained below 130° C. to avoid decomposition of malonic acid, while the reaction time was maintained at 15 min.

Content of Strontium (% Sr):

A sample of 0.2 g was dissolved in 100 mL 0.1 M $HNO_3$ prepared in Millipore water. This solution was further diluted by a factor of 500 by a solution of 1% KCl, and the content of strontium was determined by FAAS. The measurements were performed by using a Perkin-Elmer 2100 equipped with a hydrogen lamp for correction of the background signal. Strontium was measured at a slit with of 0.2 nm, the wavelength was 460.8 nm operated at an energy of 58 and a current of 8 mA.

X-Ray Crystallography

Figure 5:
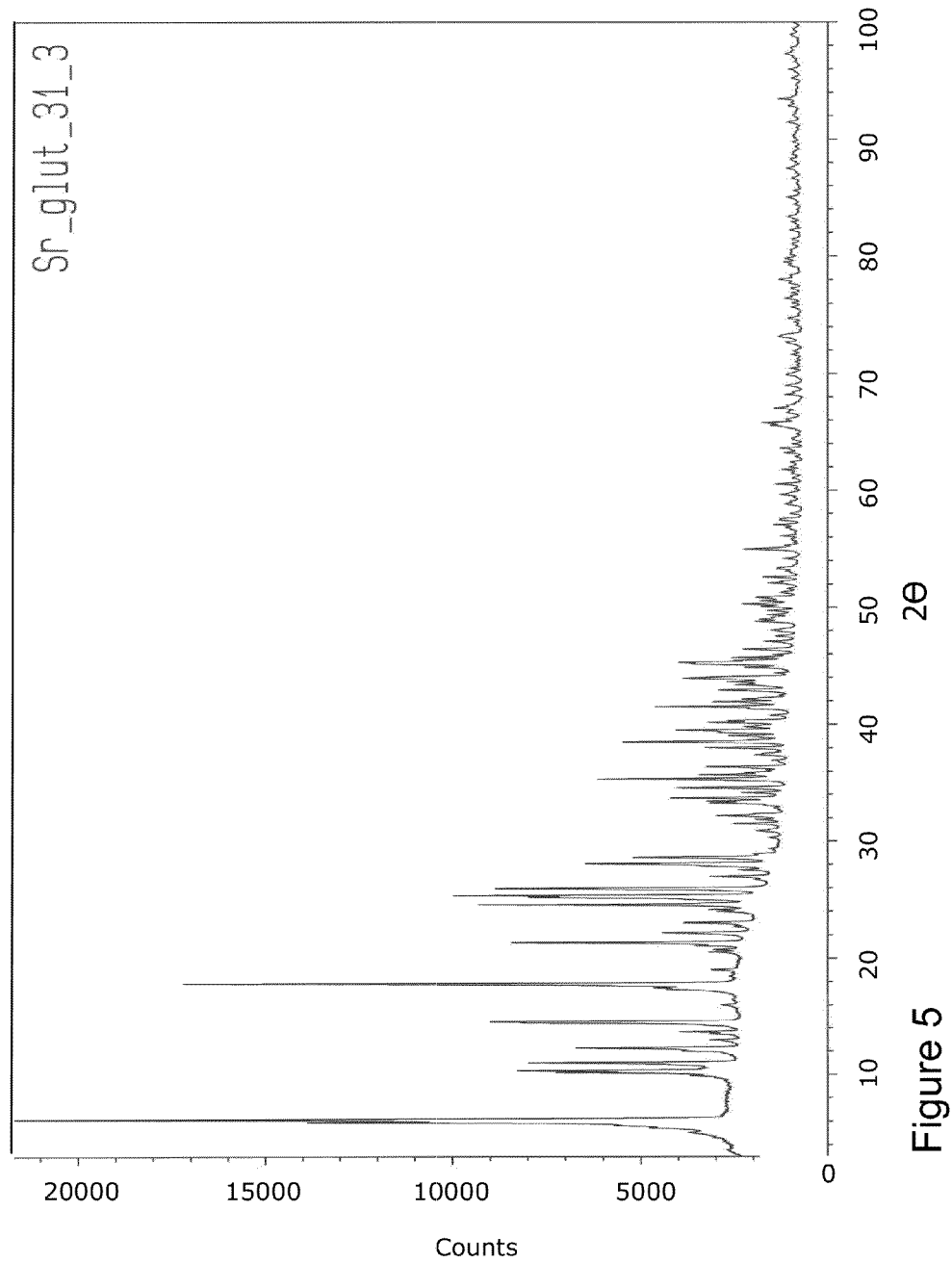
FIG. 5 is a x-ray diffractogram of crystals of strontium glutamate hexahydrate prepared by the method as described in Example 7.
Figure 6:
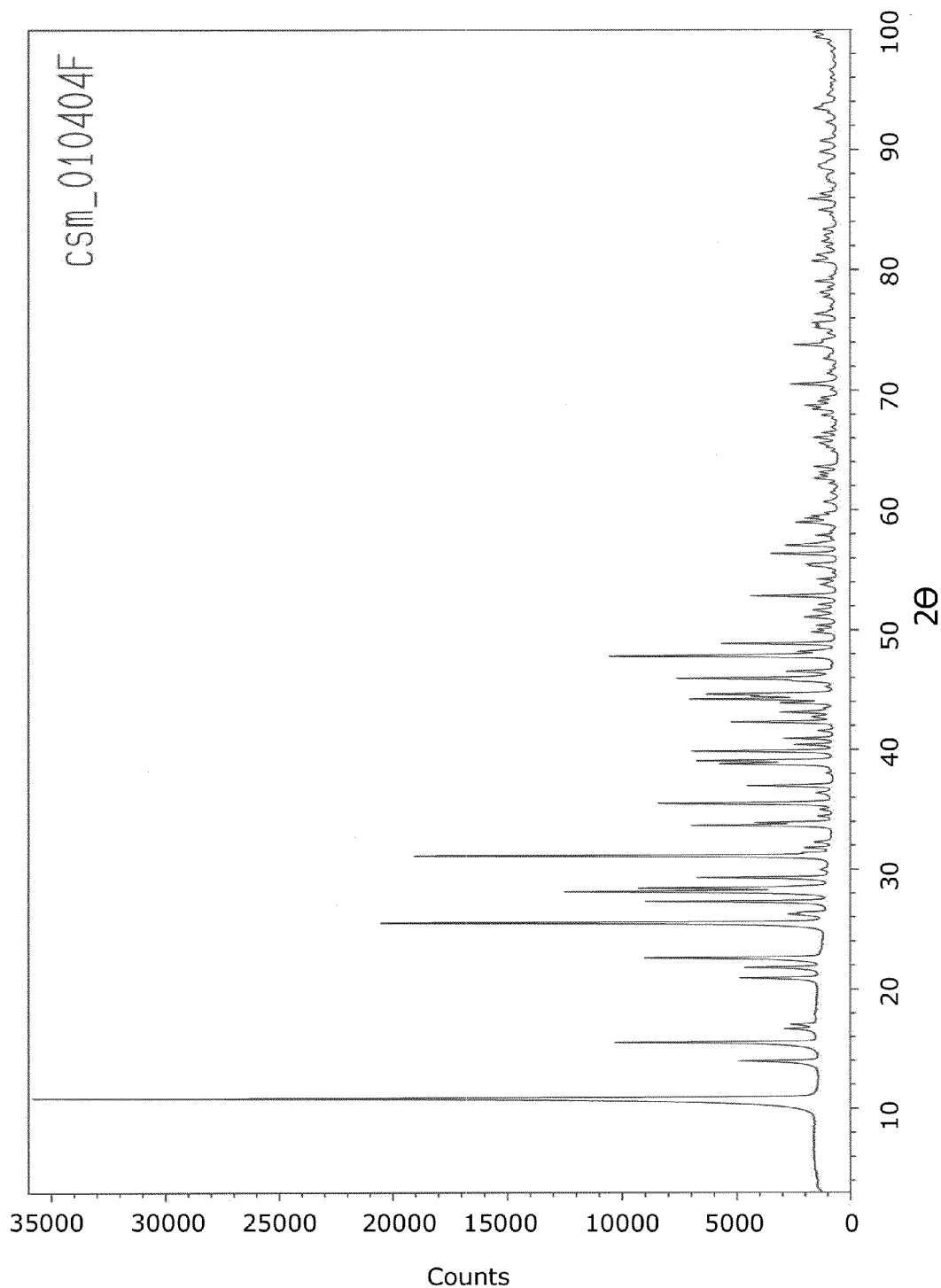
FIG. 6 is a x-ray diffractogram of crystals of strontium malonate prepared by the method as described in Example 7. The malonate salt of strontium have not previously been characterized and comprise a new crystallographic structure, but it is apparent from the stable baseline, and well defined spacing of diffraction peaks, that the crystal form of the malonate salt is homogeneous and pure.
Figure 7A:
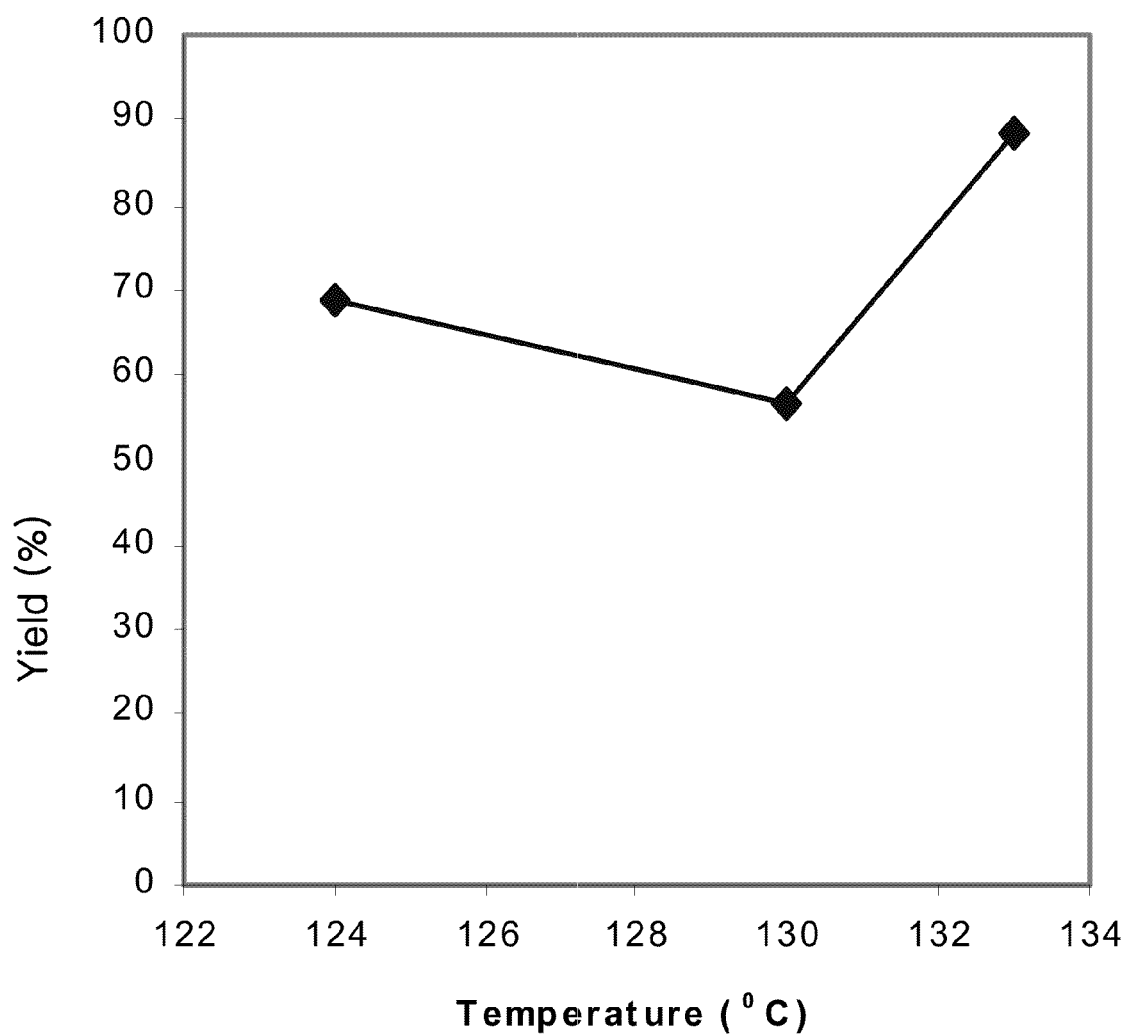
FIGS. 7A-D show the results of the optimization experiments for strontium glutamate synthesis outlined in Table 9. The influence on the yield of the synthesis of strontium glutamate was investigated by varying four parameters. (Yields above 100% indicate incomplete drying).
Figure 7B:
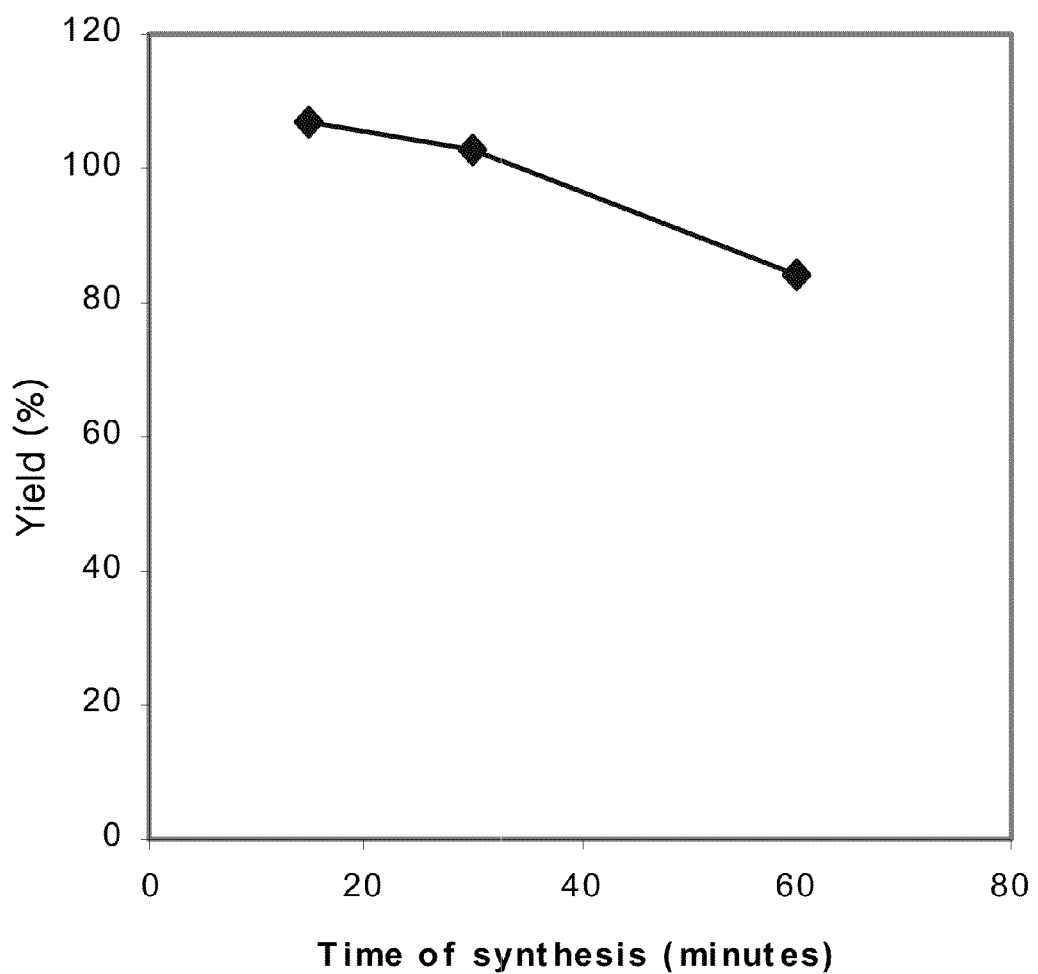
Figure 7C:
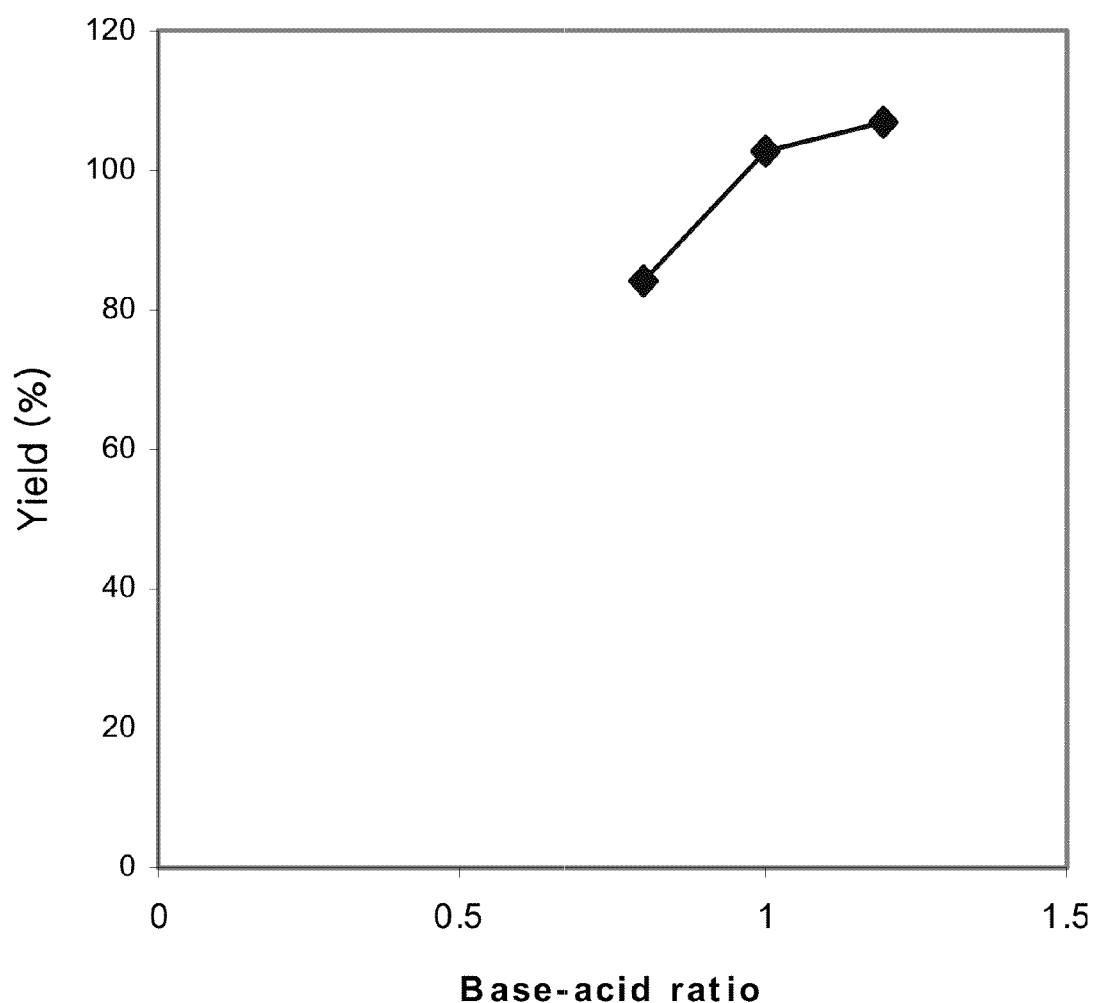
Figure 7D:
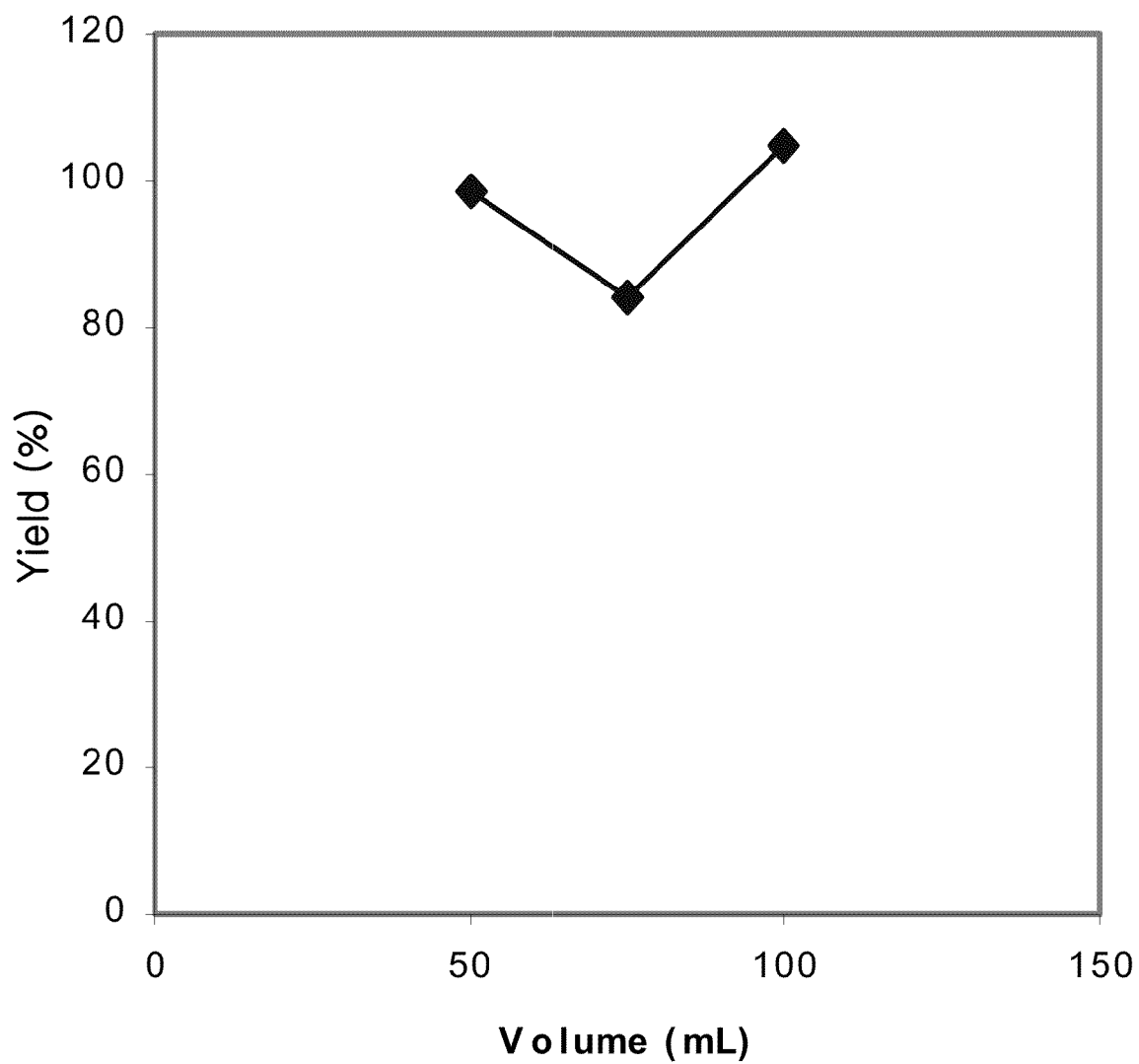

A second check of purity was performed by powder x-ray crystallography using a Huber G670 diffractometer. A characteristic diffractogram of the strontium glutamate is shown in FIG. 5. An X-ray diffractogram of strontium malonate obtained by the high temperature synthesis method disclosed in the present example is shown in FIG. 6. The double peak on the low angle side of the peak of maximum intensity observed in both FIGS. 5 and 6 is an artifact of the instrument.

Results and Discussion

In Table 9, it is observed that some of the synthesis conditions resulted in relatively low yield and in strontium glutamate of low purity as apparent from the molar % of strontium in the reaction product. The product of experiment no. 8 was produced in relatively low yield, and it did not contain the expected 25.7% of strontium, which was also confirmed by the x-ray analysis. Despite this outlier, in general, the outcome of the optimization experiments is close to the expected products. Incomplete reaction provides a product of too low content of strontium while formation of strontium carbonate during the synthesis gives a too high value of the strontium content. Conditions employed in experiments 1 and 5 gave the strontium content in best agreement with the expected value. Of notice, it is also apparent although the product of experiment no. 6 was produced in low yield; it contained an amount of strontium that corresponded to the expected value.

By studying the influence of the individual parameters on the total yield (Table 9 and FIGS. 7A-D), it becomes clear that temperature, time of autoclaving and base-acid ratio are important for the synthesis while total volume is less important. A yield higher than 100%, which is observed in experimental conditions 2, 3, 4, 5 and 7 originates from incomplete drying, but this effect is almost eliminated when the average values are considered, as in FIGS. 7A-D. Thus, the maximum yield was obtained by using a high temperature (133° C.), a short time of autoclaving (15 min.) and a surplus of strontium hydroxide. Accordingly, temperature is more important than time but it compares in importance to the base-to-acid ratio. However, great care must exerted as to not exceed the temperature of decomposition in the synthesis of other strontium salts, which for, e.g., the malonate is 132-134° C. A 10th experiment of control of optimization was performed, as to confirm the maximum yield of the optimization experiments.

Furthermore an additional experiment was performed to validate the applicability of the high temperature synthesis method for the preparation of other organic strontium salts than strontium L-glutamate. Strontium malonate was chosen, as this salt may be considered especially difficult to prepare under the high temperature conditions due to the low dissociation temperature of the malonic acid anion. However, as shown in FIG. 6, crystalline pure and well defined strontium malonate could easily be obtained. The crystal structure of the compound has not been completely resolved as it is a new structure not previously described, but the data shows that the high temperature method is likely to be applicable for many other organic strontium salts.

Further improvements of the synthesis include introduction of inert atmospheres to the synthesis environment, as well as degassing of all solutions by either nitrogen gas or by argon gas, as to reduce the formation of strontium carbonate.

Conclusion

The optimization experiments show that it is possible to synthesize strontium glutamate in high yields by elevating the temperature to values above 100° C., and by using a short time (15 min.) in the autoclave. Also, a 20% surplus of strontium-hydroxide also improves the total yield without compromising the purity of the synthesized strontium salt. A slightly more vigorous drying than silica-gel orange should be applied to the drying procedure in order to obtain completely dried product. Examples of more potent drying agents are concentrated sulphuric acid or calcium oxide, but also conventional lyophilization or other mechanic treatments may be applicable for this procedure.

Example 8

Pharmacokinetic Properties of Dicarboxylic Strontium Salts

The aim of this experiment was to assess the bioavailability of dicarboxylic strontium salts compared with strontium chloride and strontium ranelate. The bioavailability was assessed by determination of serum strontium concentration at regular intervals over a 24 hour period and calculating AUC.

The experiment was performed with female SPF Wistar rats of the strain HanTac:WH (GALAS) from Taconic M&B A/S, Ejby, DK4623 Lille Skensved, Denmark. At the start of the acclimatisation period, the rats were approximately 9 weeks old with a weight of approximately 200-250 g. The animals were housed in a room provided with filtered air at a temperature of 21° C.±3° C. and relative humidity of 55%±15% and a ventilation system providing 10 air changes per hour. The room was illuminated to give a cycle of 12 hours light and 12 hours darkness. The rats were fed a complete pelleted rodent diet "Altromin 1314" (Chr. Petersen A/S, DK-4100 Ringsted, Denmark). The rats had free access to bottles with domestic quality drinking water acidified with hydrochloric acid to pH 2.5 in order to prevent microbial growth.

The rats were randomly allocated randomly in seven groups of 9 animals treated as indicated in the table below. The groups, dose levels, animal numbers were as listed in Table 10:

TABLE 10

The 7 treatment groups of the pharmacokinetic experiment. The doses administered in the group are listed in the fist column, and salt, MW and Sr content in the middle columns.

| Dose[1] (mg/kg) | Group | Strontium salt | MW | % Sr | Dose Equivalent[1] (Amounts in mg) | Animal No's |
|---|---|---|---|---|---|---|
| Vehicle | Control | Vehicle (0.5% CMC) | — | — | — | 1-9 |
| 500 | B | Sr-ranelate (*7$H_2O$) | 639.6 | 27.4 | 500 = 137 mg $Sr^{++}$ | 10-18 |
| 416 | C | $SrCl_2$ (*6$H_2O$) | 266.6 | 32.9 | 137 mg $Sr^{++}$ = 416 | 19-27 |

TABLE 10-continued

The 7 treatment groups of the pharmacokinetic experiment. The doses administered in the group are listed in the fist column, and salt, MW and Sr content in the middle columns.

| Dose[1] (mg/kg) | Group | Strontium salt | MW | % Sr | Dose Equivalent[1] (Amounts in mg) | Animal No's |
|---|---|---|---|---|---|---|
| 533 | D | Sr-glutamate (*6H$_2$O) | 340.7 | 25.7 | 137 mg Sr$^{++}$ = 533 | 28-36 |
| 427 | E | Sr-aspartate (*3H$_2$O) | 272.7 | 32.1 | 137 mg Sr$^{++}$ = 427 | 37-45 |
| 484 | F | Sr-malenate (*6H$_2$O) | 309.7 | 28.3 | 137 mg Sr$^{++}$ = 484 | 46-54 |
| 325 | G | Sr-malonate (anhydrous) | 189.7 | 46.2 | 137 mg Sr$^{++}$ = 296 | 55-63 |

[1]Doses are adjusted to provide equimolar strontium dose as 500 mg/kg Strontium-ranelate (heptahydrate) (group B).

The test article (strontium salt) was given once by oral gavage according to the most recent body weight data. The control group was dosed with the vehicle alone (0.5% carboxy methyl cellulose, CMC). The vehicle was prepared with de-ionized water for all treatment groups including controls. The test substances (strontium salts) were solubilized/suspended in a volume corresponding to 5 ml/kg body weight. In order to keep the compounds in suspension, the formulations were kept on a magnetic stirrer before and during dosing.

Blood Samples for Toxicokinetics

On the day of treatment (Day 1), blood samples were taken from all animals. Blood samples were collected from 3 animals per group at the following time points: Pre-treatment, and 30 min, 1, 1.5, 2, 4, 8 and 24 hours post-treatment, so that three animals from each group had samples taken at time 0, 1.5 and 6 hours, 3 other rats at time 0.5, 2, 8 hours and the remaining three animals in the group had samples taken at 1, 4 and 24 hours.

Approximately 0.5-0.6 ml blood was obtained at each time point from the orbital venous plexus into plain tubes for serum. The blood was kept at room temperature for 30 to 60 minutes and until centrifugation (10 min, 1270 G, +20° C.). The serum was transferred to Nunc cryotubes (Nunc, Denmark) and frozen at −18° C. for subsequent analysis of strontium content by graphite-furnace atomic-absorption spectrometry (GF-AAS).

Graphite-Furnace Atomic-Absorption Spectrometry (GF-AAS)

Concentrated HCl was added to the serum samples to a final concentration of 0.2% HCl and the samples were then subjected to analysis using a Perkin-Elmer 2100 equipped with a hydrogen lamp for correction of the background signal. Strontium was measured at a slit with of 0.2 nm, the wavelength was 460.8 nm operated at an energy of 58 and a current of 8 mA.

Results of the Pharmacokinetic Study of Strontium Salt Absorption

In FIGS. 8A-F, the serum concentrations measured in the six groups treated with strontium salts are plotted as a function of the time after administration of the compounds. It is apparent that administration of the strontium salts results in a rapid and highly significant increase in serum strontium concentrations. When comparing the pharmacokinetic properties of different salts, it is apparent that both the highly soluble strontium chloride as well as the relatively poorly soluble strontium ranelate (see Example 3), is rapidly absorbed, reaching a maximum serum concentration after approximately 2 hours.

The di-carboxylic acids with higher solubility, and especially the strontium salts of the amino acids L-aspartate and L-glutamate reach the maximal serum concentration with a slower kinetic rate and, with maximal concentration reached after approximately 8 hours. Furthermore, the serum strontium concentration in the time interval from 0-8 hours after the administration of the test substance appears more stable, at least for some of the di-carboxylic acids such as the aspartate and malonate salts of strontium. This pattern of two distinct peaks of maximal serum concentration is also apparent in the group treated with strontium malonate. It is likely to indicate that the strontium ion is taken up by two distinct absorption mechanisms, and that the highly soluble strontium salts according to the present invention may have particular potential to exploit the biphasic nature of the strontium uptake mechanism, and thus proved an overall benefit apparent as higher bioavailability of the strontium.

Figure 8A:
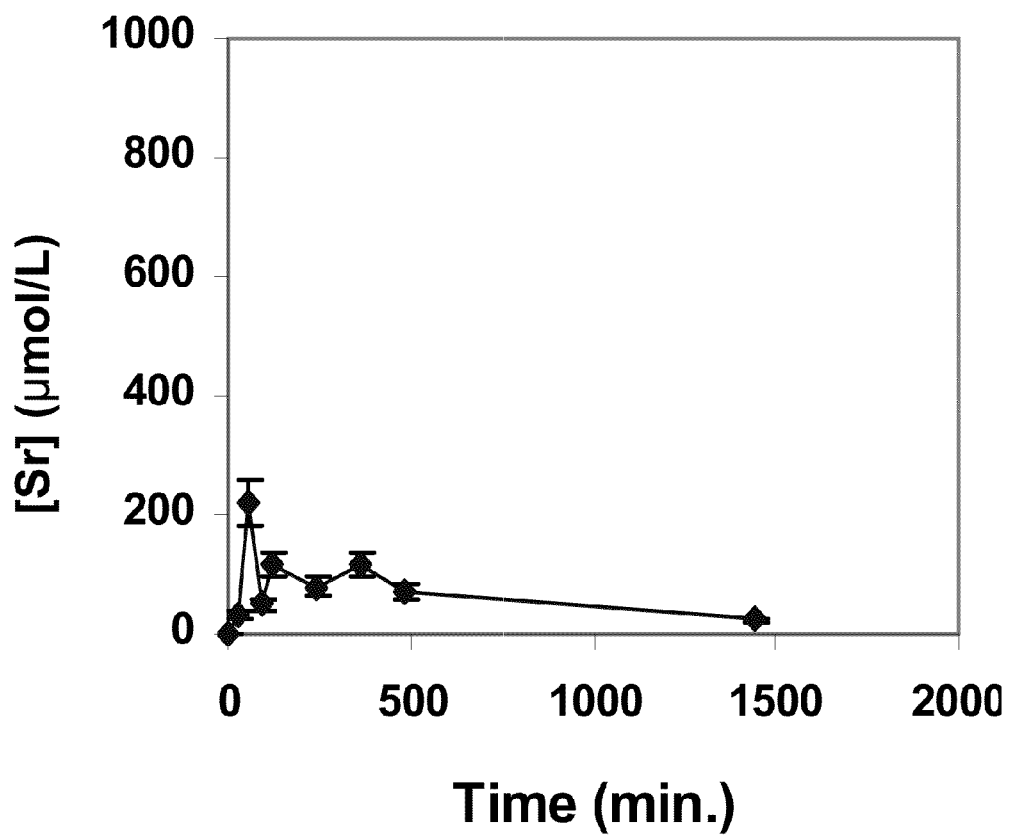
FIGS. 8A-F are plots of serum strontium concentrations measured in rats given a single dose of strontium as indicated in the upper part of each panel. The data points represent mean and standard deviation for each measuring point. Pre-dose represent corresponding samples taken from animals treated with vehicle alone.
Figure 8B:
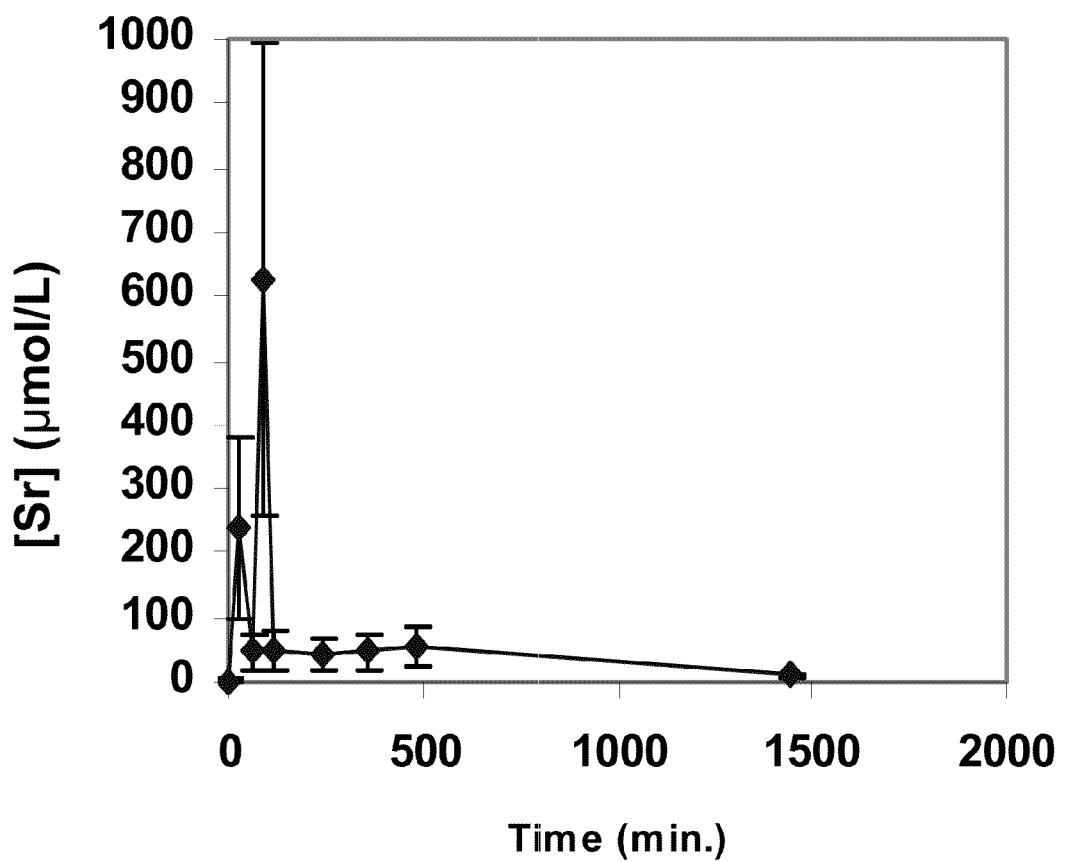
Figure 8C:
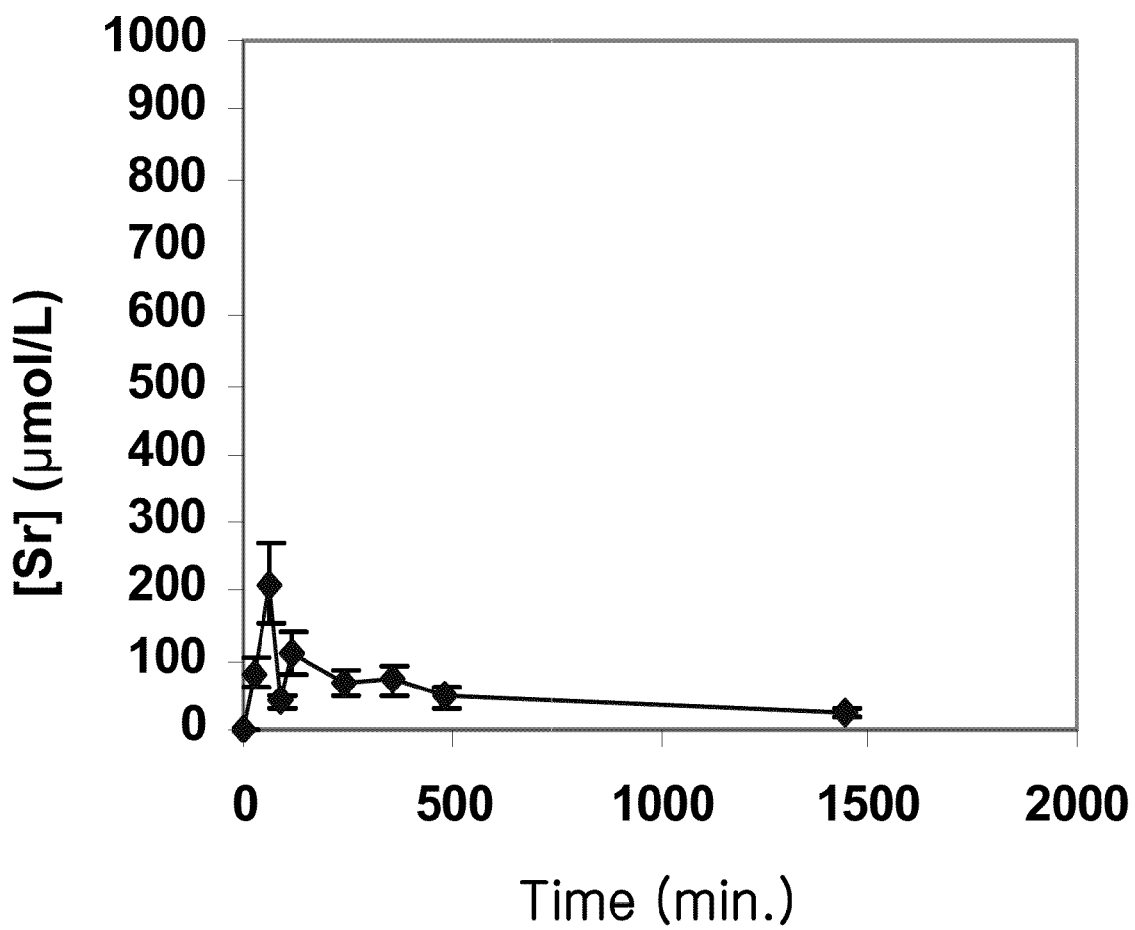
Figure 8D:
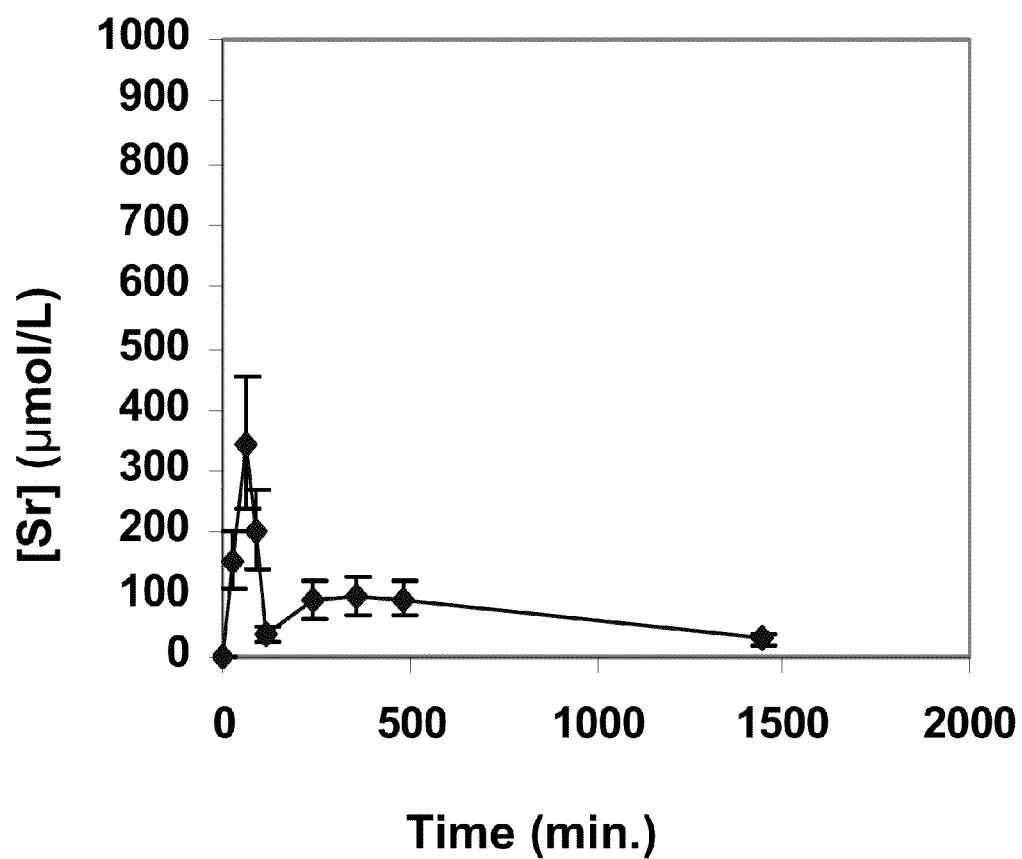
Figure 8E:
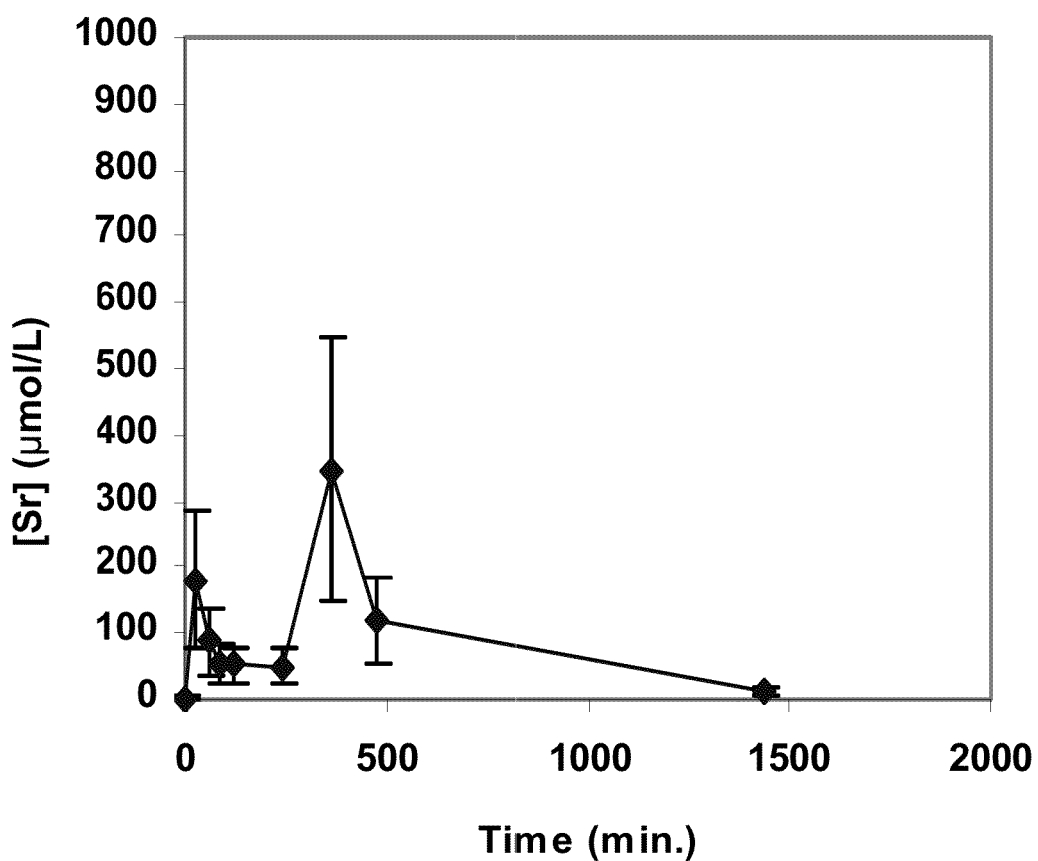
Figure 8F:
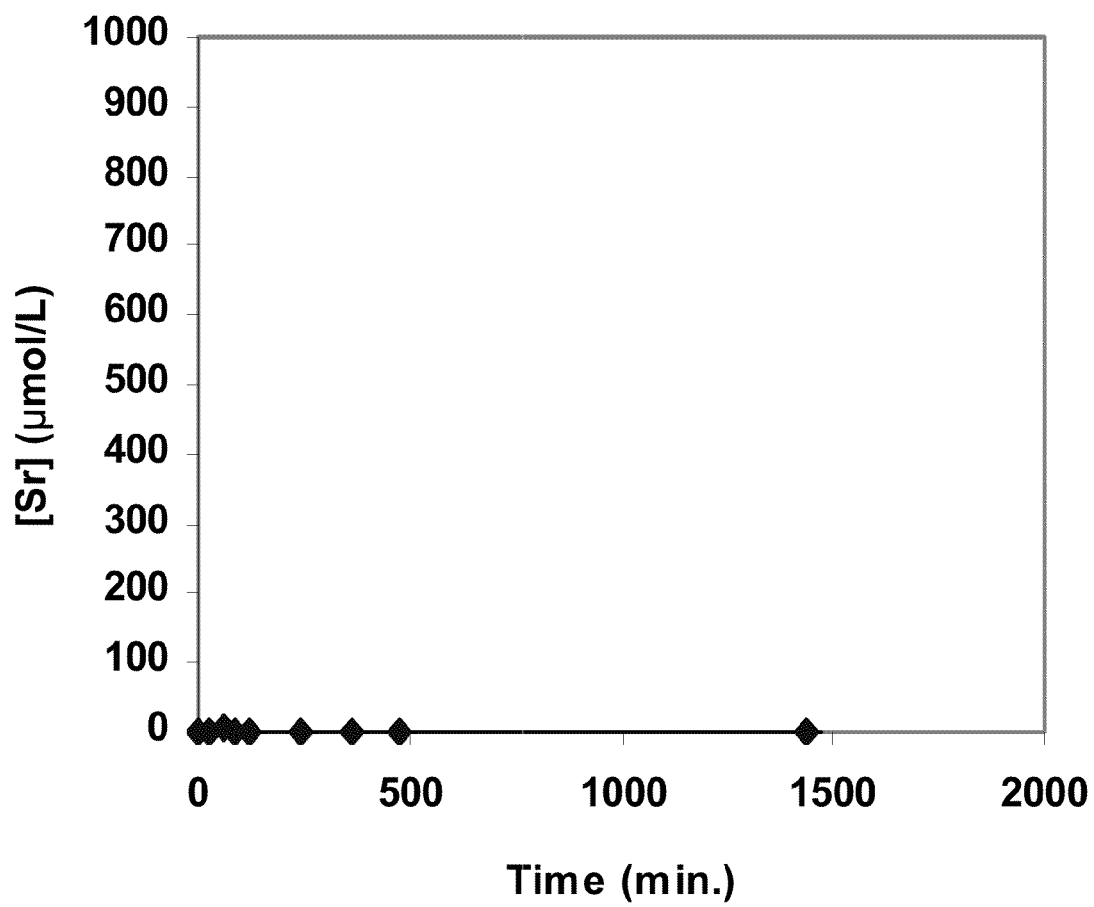
Figure 9A:
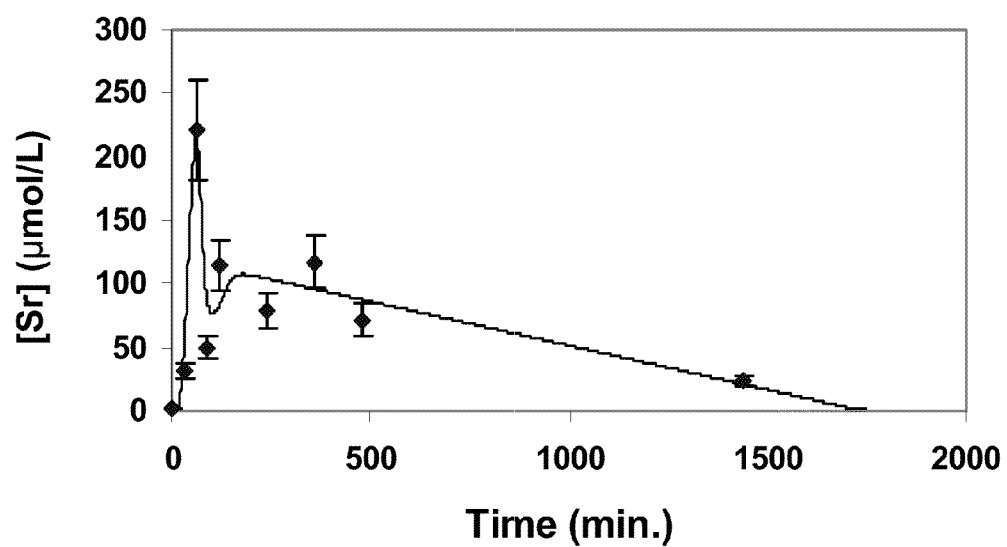
FIGS. 9A-B are plots of theoretical values (solid line) to experimental data (diamonds) of strontium with error bars superimposed. The theory fits the data excellently and the area under the curves (AUC) are calculated by the model. The strontium content always peaked after 60 min. but the second peak defined by the rate of metabolism vary between the salts. In the present examples, the Sr-α-ketogluterate is quickly metabolized while Sr-glutamate rests longer in the serum.
Figure 9B:
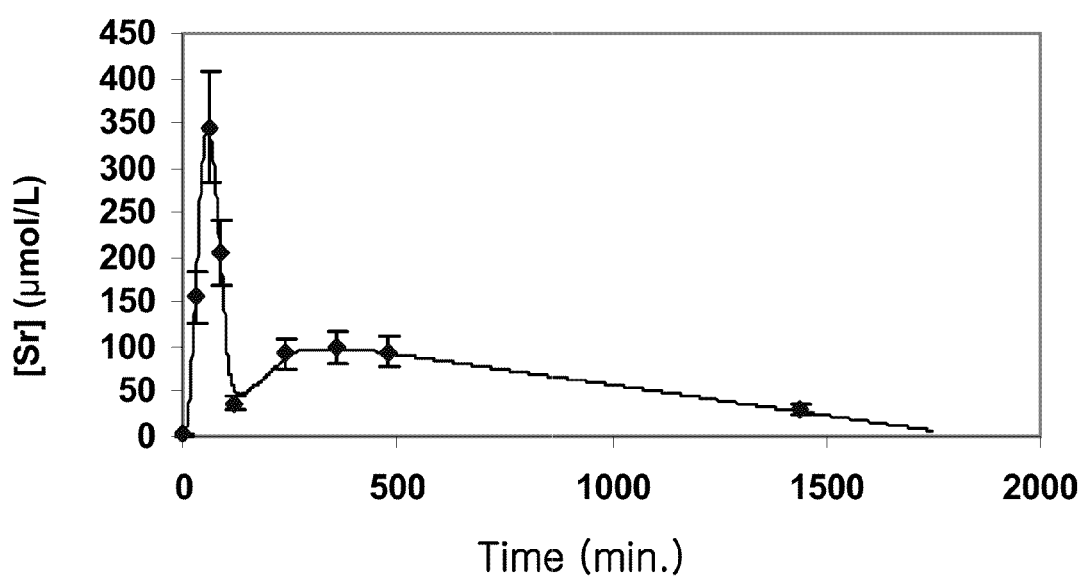

When AUC calculations were performed the general course of the curves, as evidenced by average values in FIGS. 8A-F, was best described by modeling the response/pharmacokinetic curves in a specially developed mathematical model. In the initial step, it assumes that the strontium is not metabolized but simply transferred from the stomach/upper digestive tract of the rat into epithelial cells by an active transport mechanism. Also without metabolism, the strontium ion is then transferred from the stomach/upper digestive tract where it is simultaneously released to the blood vessels. Only during the circulation of strontium through the veins, the strontium is dispersed and metabolized by the body tissue. This credible but simplified description, thus includes a two-step mechanism of absorption of ionic strontium after oral administrations of the strontium ions, identified by the two peaks in each of FIGS. 9A and 9B at t =60 min and at t =360 min. After the strontium dose was administered to the rats, a characteristic time of uptake was found as t =12 min. The maximum content of strontium in the serum was observed after approx. 30 min. The characteristic time value of 12 min. is interpreted as the duration of strontium ions being taken up by the active transport mechanism from the intestinal lumen and secreted into circulation. The time of strontium transfer between the stomach and the blood vessels is initiated almost instantly, while the time of transfer between the guts and the blood vessels proceeds at a later stage that depends on the type of salt investigated. The malonate, in particular, exhibits a peak in the uptake-versus time from the guts to the blood vessels at t =360 min., as seen in FIG. 8E. Thus, the time of body metabolism of the malonate is very long, as compared to that of the other salts. For all salts, however, the strontium content levels out after approx. 1750 min. (29 hours) and approaches the natural level corresponding to the pre-dose level.

The model calculations (not shown) were applied to the determination of the areas under the curve that are shown in Table 11. The standard deviations of the AUC values correspond to the general uncertainty on the measurements of FIGS. 8A-F, and their magnitude does not allow for a significant discrimination between the salts. The AUC values of the salts are much higher than the AUC value of the pre-dose samples.

TABLE 11

Determination of the area under the curve according (AUC) to the model calculations.

| ANION OF Sr-SALT | AUC mg/L · min | STDDEV mg/L · min |
|---|---|---|
| α-ketogluterate | 9000 | 1600 |
| Aspartate | 7000 | 1700 |
| Chloride | 7300 | 2000 |
| Glutamate | 10100 | 3100 |
| Malonate | 15000 | 8500 |
| Pre-dose | 168 | 67 |
| Average | 6800 | 5400 |

These effects of delayed uptake of strontium and serum levels in a sustained level over longer time periods observed with strontium salts with di-carboxylic organic anions may enhance the pharmacological properties of the compounds. The delayed attainment of $C_{max}$ may be an advantage for the use of the strontium compound in the treatment of diseases and conditions affecting bone metabolism. In these cases it is often an advantage to administer the compound in the evening before bedtime, as this would allow the compound to act at night, when resorption of bone is occurring at the highest rate. Furthermore, the administration before bedtime minimizes the potential interference from calcium in the normal diet, as the pharmaceutical preparation of the strontium salt would be taken after the last meal. This is in contrast to administration during the day, where the calcium content of normal meals would have the potential to interfere and reduce the uptake of strontium. The gradual increase in serum strontium concentration over 4-8 hours after administration of the compound would comply well with evening administration of the compound and appears well suited to maximize the therapeutic effect of the strontium compound on bone metabolism.

Example 9

Preparation of 300 mg Strontium Malonate Tablets

The following manufacturing procedure was followed for the preparation of approximately 10,000 tablets containing 300 mg of strontium malonate (anhydrous) and other ingredients in the proportions specified in the table below.
Pharmaceutical Composition Containing 300 mg Strontium Malonate

| Tablet formulation | |
|---|---|
| Ingredient | Amount (mg)/tablet |
| Strontium malonate (anhydrous) | 300 mg |
| Microcrystalline Cellulose Ph. Eur. | 43.5 mg |
| Polyvidone Ph. Eur. | 12 mg |
| Colloidal anhydrous silica Ph. Eur. | 2.5 mg |
| Magnesium Stearate Ph. Eur. | 2.5 mg |
| Purified water Ph. Eur. | q.s. |

Strontium malonate (3600 g) and Microcrystalline Cellulose (Avicell, 180 g) were mixed thoroughly in suitable mixing equipment. After mixing, the material was filtered through a 1 mm diameter sieve. Over a period of 2 minutes and under constant mixing, Polyvidone (144 g) and purified water (450 g) were added to the mixture. When a homogenous granulate was obtained, it was sifted through a 1.2 mm sieve and placed on trays for drying, and the trays placed in a drying cupboard at 40° C., for 2½ to 3 hours. Drying was monitored by measuring the relative humidity of the air in the drying cupboard, and drying was considered complete when the water content was between 25-40% RH. The dried granulate was passed through a 1 mm diameter sieve. Colloidal Anhydrous Silica (23 g) and remaining Microcrystalline Cellulose (Avicell, 284 g) were mixed thoroughly and sieved through a 0.7 mm diameter sieve. The granulate and the silica-cellulose mixture were blended. Magnesium Stearate (23 g) was sieved through a 0.7 mm diameter sieve and premixed with approximately 350 g of the mixture, and when a homogenous mixture was obtained, the rest of the mixture was added. The mixture was added to a compression tabletting machine, and 360 mg (containing 300 mg strontium malonate) tablets were pressed in 8 mm cylindrical tablet stamps.

Example 10

Preparation of 600 mg Strontium Malonate Tablets

The following manufacturing procedure may be used for the preparation of approximately 5000 tablets containing 600 mg of strontium malonate (anhydrous) and other ingredients in the proportions specified in the table below.
Pharmaceutical Composition Containing 600 mg Strontium Malonate

| Tablet formulation | |
|---|---|
| Ingredient | Amount (mg)/tablet |
| Strontium malonate (anhydrous) | 600 mg |
| Microcrystalline Cellulose Ph. Eur. | 87 mg |
| Polyvidone Ph. Eur. | 24 mg |
| Colloidal anhydrous silica Ph. Eur. | 5 mg |
| Magnesium Stearate Ph. Eur. | 5 mg |
| Purified water Ph. Eur. | q.s. |

Strontium malonate (3600 g) and Microcrystalline Cellulose (Avicell, 180 g) are mixed thoroughly in suitable mixing equipment. After mixing the material is filtered through a 1 mm diameter sieve. Over a period of 2 min and under constant mixing, Polyvidone (144 g) and purified water (450 g) are added to the mixture. Additional water may be added if required for obtaining a homogenous granulate. When a homogenous granulate has been obtained, it is sifted through a 1.2 mm sieve and placed on trays for drying, and the trays are placed in a drying cupboard at 40° C., for 2½-3 hours. Drying is considered complete when the water-content was between 25-40% RH. The dried granulate is passed through a 1 mm diameter sieve. Colloidal Anhydrous Silica (23 g) and remaining Microcrystalline Cellulose (Avicell, 284 g) are mixed thoroughly and sieved through a 0.7 nm diameter sieve. The granulate and the silica-cellulose mixture are blended. Magnesium Stearate (23 g) is sieved through a 0.7 mm diameter sieve and premixed with approximately 350 g of the mixture, and when a homogenous mixture has been obtained, the rest of the mixture is added. The mixture is added to a compression tabletting machine, and 721 mg (containing 600 mg strontium malonate) tablets are pressed in cylindrical oblong tablet stamps. The above-described manufacturing procedure is readily scaled up for preparation of larger batches of tablets.

Skilled artisans will recognize that the tablet size may be varied by varying the tablet stamping tools. Furthermore, variations in the strength of the tablet can be readily accommodated by modifications of the above-described compositions.

Example 11

Determination of Pharmacokinetic Properties of Strontium Malonate

The pharmacokinetic properties of the 300 mg strontium malonate tablet prepared in Example 9 were determined in a single oral dose pharmacokinetic study in humans. To enable accurate assessment of pharmacokinetic properties of the strontium malonate-containing tablets of Example 9, three dose-levels were administered to the study subjects, a 0.6 g dose of strontium malonate (2 tablets), a 1.2 g dose of strontium malonate (4 tablets) and a 2.4 g dose of strontium malonate (8 tablets). Furthermore, 2.0 g of strontium ranelate was administered from a sachet dosage form (Protelos®, Servier Laboratories Ltd.) to a separate treatment group to do a comparison of pharmacokinetic properties between the dosages of strontium malonate and strontium ranelate. An additional goal of the study was to determine the bioequivalent dose of the tablets of Example 9, containing strontium malonate, giving the same amount of absorbed strontium as the 2.0 g strontium ranelate dose present in a commercially available sachet formulated dosage form.

Placebo tablets were used in the study. These tablets were manufactured as described in Example 9, but all strontium malonate was substituted with microcrystalline cellulose (avicell). The placebo tablets were stamped in the same tablet machine as the strontium malonate tablets and had the same visual appearance.

The percentages of strontium and molecular weights of the particular salt forms of strontium malonate and strontium ranelate used to calculate the theoretical bioequivalent dose of strontium malonate to 2.0 g strontium ranelate is shown below in Table 12.

TABLE 12

| Group | Dose (mg) | Strontium salt | MW | % Sr | Dose Equivalent |
|---|---|---|---|---|---|
| 1 | 1200 | Sr-malonate (*0H$_2$O) | 189.6 | 46.2 | 1200 mg = 554 mg Sr$^{++}$ *) |
| 2 | 2000 | Sr-ranelate (*7H$_2$O) | 639.6 | 27.4 | 2000 mg = 548 mg Sr$^{++}$ |

In the study, sixty healthy male volunteers, between 18 and 40 years of age were enrolled in the pharmacokinetic study. Prior to initiation of the study, the study protocol was approved by an Independent Ethics Committee, and all procedures were performed according to Good Clinical Practice.

Trial Objectives and Purpose

The primary objective of the study was to obtain pharmacokinetic (PK) data (AUC$_{5\ weeks}$ and C$_{max}$) on the strontium malonate tablets prepared according to Example 9. Secondary objectives of the study were:

to demonstrate bio-equivalence of 2.0 g of strontium ranelate and the medium dose of 1.2 g of strontium malonate;
to estimate the dose of strontium malonate that is equivalent to 2.0 g of strontium ranelate, in terms of AUC;
to obtain data on safety parameters of strontium malonate;
to obtain data on markers of calcium balance; and
to obtain data on biochemical markers of bone turnover.

As used herein, bioequivalence (BE) is defined as follows: Two medicinal products are bioequivalent if they are pharmaceutical equivalents or pharmaceutical alternatives, and if their bioavailabilities after administration in the same molar dose are similar to such degree that their effects, with respect to both efficacy and safety, will be essentially the same (CPMC/EWP/QWP/1401/98).

In the present study, BE is assessed by AUC and C$_{max}$ which were both evaluated during the 5 week follow up period on the strontium malonate medium dose (1.2 g) and 2.0 g strontium ranelate (Protelos®). BE is demonstrated if confidence intervals of the ratio of the two interventions are lying within the 80-125% range for both AUC and C$_{max}$.

The study was performed as a semi-blinded randomized, single dose, parallel-group study, with 12 healthy volunteers enrolled for each of the 5 administration regimens.

Subjects were allocated to one of the strontium malonate arms or the placebo arm received a total of 8 identical tablets. Either:

0.6 g dose-group: 2 strontium malonate (SM) 300 mg tablets and 6 placebo tablets,
1.2 g dose-group: 4 strontium malonate (SM) 300 mg tablets and 4 placebo tablets,
2.4 g dose-group: 8 strontium malonate (SM) 300 mg tablets or
Placebo: 8 placebo tablets.

An additional study group was administered strontium ranelate (Protelos®). As Protelos® is formulated as yellowish granules for suspension in water it was decided, for pharmaceutical reasons, not to include Protelos® in the blinding.

For practical reasons, the treatment and follow up of all 60 subjects were divided in 6 separate treatment "occasions", where 10 subjects were included and treated per occasion. The subjects were randomized in blocks of 10 to one of the 5 interventions at baseline; 2 subjects for each intervention. All subjects, including the placebo group, were asked to take the study medication in a glass of 200 ml water.

Each intervention was performed as a single oral dose administration in the evening, at least six hours after the last meal, i.e., the study subjects were not to eat dinner the evening of the investigational medicinal product administration.

The study drug administration took place at 7 p.m. During the 24 h study period following the administration of the study medication, the subjects were given a meal at 8 am. and 12 a.m. and a light snack at 3 p.m.

For determination of pharmacokinetic properties of the strontium compounds the main analysis method consisted of determination of ionic strontium in serum samples from the study subjects. Blood samples were taken at regular intervals after administration of the study drug, and processed to serum for determination of strontium content by ICP-MS (inductively coupled plasma mass spectroscopy). Blood samples were withdrawn from subjects at 0 minutes, 30 minutes, 60 minutes, 90 minutes, 2 hours, 3 hours, 4 hours, 6 hours, 8 hours, 24 hours, 1 week, 3 weeks and 5 weeks after administration of the study drug.

Determination of strontium as $Sr^{++}$, in serum was performed using ICP-MS for quantitative determination of ionic strontium concentration in the formulation. Prior to analysis the formulation was diluted in 0.1 M $HNO_3$ before measurement, to obtain a suitable concentration range of the solution. A Perkin Elmer Elan 5000 system equipped with a cross-flow nebulizer was used for the ICP-MS measurements.

Results

The study medications were well tolerated in all 60 study subjects and all subjects were available for the full study period. Two subjects did not have 5 week samples available and thus, the sample cohort for the per protocol (PP) analysis were 58 compared with 60 for the full intention to treat analysis (ITT). All subjects had a well defined strontium profile curve enabling a calculation of the $AUC_{5week}$ (see FIG. 10). Some subjects reported mild symptoms, during the first 24 hour period (headache, cold-symptoms, allergies, etc.), none of which were serious or likely to be related to the study medication, and the reports of overall symptoms were evenly distributed in all treatment groups. However of note, 2 of the 12 subjects given strontium ranelate reported diarrhea, whereas this was not seen in any of the 36 subjects treated with strontium malonate, indicating that the strontium malonate may be devoid of the diarrhea side effect which is associated with strontium ranelate.

Figure 10:
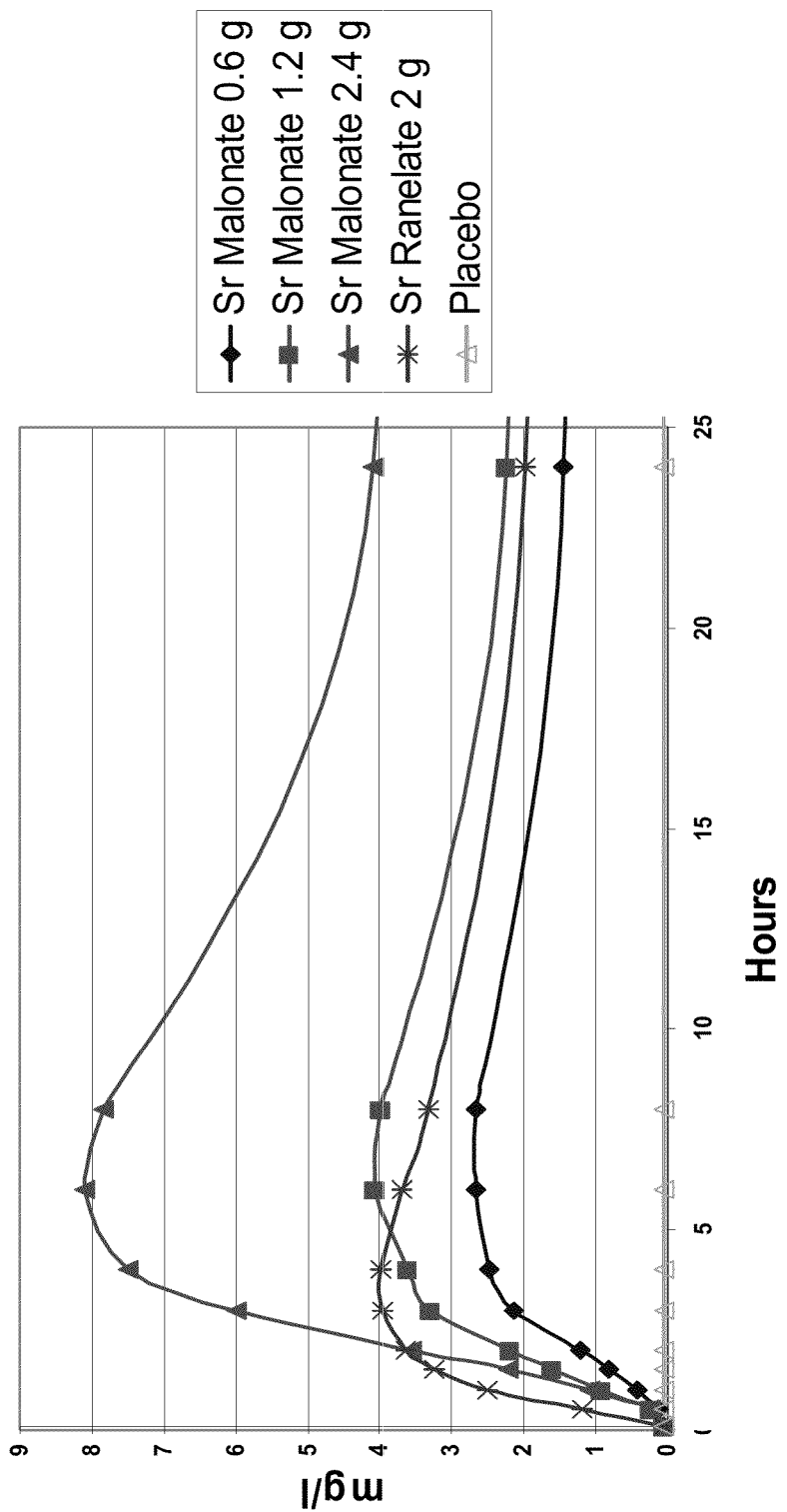
FIG. 10 is a plot of the strontium plasma concentration vs. time following single dose oral administration of strontium malonate (0.6 g, 1.2 g and 2.4 g), strontium ranelate (2.0 g) and placebo compositions in human subjects.

The pharmacokinetic properties in the three study groups treated with strontium malonate demonstrated a clear dose response in the uptake of strontium from the administered preparation of the product (FIG. 10). AUC was calculated in arbitrary units in both the ITT and the PP population (Tables 13 and 14). It is apparent from the PK graphs of circulating strontium levels depicted in FIG. 10, and from the tabular presentation in Table 13 of $AUC_{5week}$ data for each of the four treatment groups that 1.2 g strontium malonate shows higher bioavailability than the 2.0 g of strontium ranelate. The theoretical bioequivalent dose to 2 g strontium ranelate (Protelos®), was found to be 1.09 g by inverse regression. This was performed by using the following model for assessing the linear relationship between strontium levels administered to the study subjects (dose) and the resulting uptake of strontium into circulation assessed as $AUC_{5week}$:

$$AUC = \alpha \cdot Dose^\beta \Rightarrow \log(AUC) = \log(\alpha) + \beta \cdot \log(Dose)$$

The dose of strontium malonate, which in terms of AUC was bio-equivalent with 2.0 g Protelos® was estimated from the dose-response relationship established in the model above, by inverse regression. The strontium malonate estimate was based on the actual estimates of $\alpha$ and $\beta$ obtained when the values from the groups of study subjects treated with 0.6, 1.2 and 2.4 g strontium malonate was applied in the model. Using the AUC value obtained in the group treated with the 2.0 g strontium ranelate sachet formulation the bioequivalent strontium malonate dose was found to 1.09 g and a 95% confidence intervals was calculated (Fieller's theorem) to [1.073, 1.115].

Thus, the study demonstrated a significant difference in the bioavailability of strontium malonate tablets of Example 9 compared to the strontium ranelate dosage form, as similar strontium concentrations were obtained after administration of 2.0 g strontium ranelate could be obtained with a strontium malonate dose significantly below the equimolar dose of 1.2 g.

TABLE 13

Analysis of AUC - 5 Weeks (Intention to Treat Analysis, ITT) (SM = strontium malonate)

| | AUC Estimate (SE) | 90% CI | Wald test | P-value |
|---|---|---|---|---|
| SM 0.6 g | 275273 (24317) | | | |
| SM 1.2 g | 386901 (39455) | | | |
| SM 2.4 g | 654617 (63742) | | | |
| Protelos ® 2.0 g | 356347 (24434) | | | |
| Placebo | 40992 (1984) | | | |
| | Ratio (SM/Protelos ®) | | | |
| SM 0.6 g | 0.77 (0.086) | [0.63, 0.92] | 6.94 | 0.008 |
| SM 1.2 g | 1.09 (0.133) | [0.87, 1.31] | 0.41 | 0.52 |
| SM 2.4 g | 1.84 (0.219) | [1.48, 2.20] | 14.6 | 0.0001 |

TABLE 14

Analysis of AUC - 5 Weeks (SM = strontium malonate) (Per protocol analysis, PP)

| | AUC Estimate (SE) | 90% CI | Wald test | P-value |
|---|---|---|---|---|
| SM 0.6 g | 276048 (26625) | | | |
| SM 1.2 g | 412109 (33249) | | | |
| SM 2.4 g | 654617 (63742) | | | |
| Protelos ® 2.0 g | 356347 (24434) | | | |
| Placebo | 40992 (1984) | | | |
| | Ratio (strontium malonate/Protelos ®) | | | |
| SM 0.6 g | 0.77 (0.092) | [0.62, 0.93] | 6.04 | 0.014 |
| SM 1.2 g | 1.16 (0.122) | [0.96, 1.36] | 1.63 | 0.201 |
| SM 2.4 g | 1.84 (0.219) | [1.48, 2.20] | 14.6 | 0.0001 |

For $T_{max}$, it was observed that the tablets of Example 9 (containing strontium malonate) resulted in a delayed uptake compared to strontium ranelate. $T_{max}$ was 1-2 hours later in all three strontium malonate-treated groups compared to the strontium ranelate-treated groups.

Conclusions

The single dose pharmacokinetic study demonstrated that strontium was taken up in a dose dependent fashion when strontium malonate was administered as an oral tablet formulated pharmaceutical product to human subjects. The bioavailability of strontium from the tablets of Example 9 was better than from the strontium ranelate dosage form (Protelos®), as the bioequivalent dose of strontium malonate to 2.0 g strontium ranelate is 1.09 g, significantly less than the theoretically equimolar dose of 1.2 g of the composition of Example 9.

Example 12

Manufacture of Anhydrous Strontium Malonate at 95-100° C.

The present example is provided to illustrate the applicability of a high temperature synthetic method according to the invention to produce strontium malonate in kg-scale quantities.

63.2 kg of purified water was mixed with 15.75 kg of strontium hydroxide octahydrate (Riedel de Hahn, Germany) in a closed 100 L commercial scale reactor under a nitrogen atmosphere. The reactor was made of glass-lined stainless steel providing a chemically inert surface that is easily cleaned after completion of manufacture. The strontium hydroxide was dissolved at a temperature of 97.1° C., and the resulting unclear solution was transferred to a nitrogen filled pressure filter (heated 96° C.) to remove strontium carbonate. The reactor was cleaned with diluted hydrochloric acid, tap water and finally with purified water.

A 10 L polyethylene (PE) container was charged with 5.630 kg (54.1 mol) of malonic acid (Sigma, USA) and purified water (4.1 kg), and the mixture was shaken until a clear solution was obtained. The malonic acid solution was then filtered into the 100 L reactor containing the strontium hydroxide solution. This reactor was of similar design to the one used for dissolving the strontium hydroxide as described above. The PE container and the filter were washed with purified water (1.4 L) for future use. The reactor was evacuated and equilibrated with nitrogen three times before the solution was heated to a gentle reflux under a nitrogen atmosphere.

The hot strontium hydroxide solution was filtered and added into the reactor containing the strontium malonate solution at a starting temperature of 96.2° C., and the resulting mixture was continually mixed for a period of 21 minutes. At the end of the mixing period the reaction temperature was 97.9° C. After 2 hours and 51 minutes, the reaction temperature was 44.4° C. The reaction product was filtered on a pressure filter preheated to 48° C. The filter cake containing the strontium malonate was washed with purified water (13.2 kg) preheated to 45.1° C., and subsequently dried in a vacuum at 70° C. to give 9.631 kg of anhydrous strontium malonate, which corresponds to 93.9% of the theoretical yield.

Example 13

Calculation of Steady State Plasma Levels from Single Dose Pharmacokinetic Experiment in Man The modelling of the steady state level of circulating strontium was based on individual 0 hours to 5 weeks single dose strontium profiles as obtained from the single dose pharmacokinetic experiment described above in Example 11. From these profiles individual estimated 0-24 hours steady state profiles was calculated as the sum of
  a. the sample values at 0, 0.5, 1, 1.5, 2, 3, 4, 6, 8, and 24 hours on day I (data recorded directly in the trial); and
  b. corresponding terms of e.g., 1 hours on day 2, 3, 4 etc. The sum of these terms is found as the sum of an infinite series using a model for the terminal elimination. This corresponds to using the accumulation factor (1).

This modelling yields estimates of the steady state strontium levels with two assumptions:
  1. Dose linearity of strontium pharmacokinetics within the range of concentrations involved.
  2. The model for the terminal elimination is reasonably accurate.

The terminal elimination was estimated for each subject on basis of the 24 hours and the 1, 2, and 3 weeks concentrations. The one-compartment model with exponentially decreasing concentrations was used, partly because a reasonable fit was observed and partly because a more complex model could only be estimated on the available data with great uncertainty.

With t being a time point within the first 24 hours the formal estimation of the steady state concentration will be given according to the formula listed below:

$$C_{ss}(t) = C(t) + \hat{C}(t+24) + \hat{C}(t+48) + \hat{C}(t+72) + \ldots$$

Where C(t) is the measured concentration after single dose administration, and $\hat{C}(t+i\cdot 24)$ are estimated from the single dose terminal elimination model. Assuming the one-compartment model this reduces to $$C_{ss}(t) = C(t) + \frac{K\exp(-k_e t)}{1 - \exp(-k_e 24)}$$

with $k_e$ being the elimination constant and K being the proportionality constant in the terminal elimination. The parameters in the one-compartment model were estimated by linear regression on the log-transformed concentration values.

All calculations were based on baseline adjusted strontium concentrations, as the strontium concentrations in the baseline situation is not zero due to the intake of small amounts of strontium in the normal diet of the study subjects.

Results

A total of six concentration values were marginally below zero after baseline adjustment. These observations were set to 1 ng/ml to avoid problems with log-transformation. By inspecting log concentration plots (not shown) it was detected that the elimination of strontium is not well described by a one-compartment model from 24 hours and onwards. It is however assessed that for summing to infinity the one-compartment model will give reasonable estimates in this situation where a single strontium dose has been administered to the study subjects.

Figure 11:
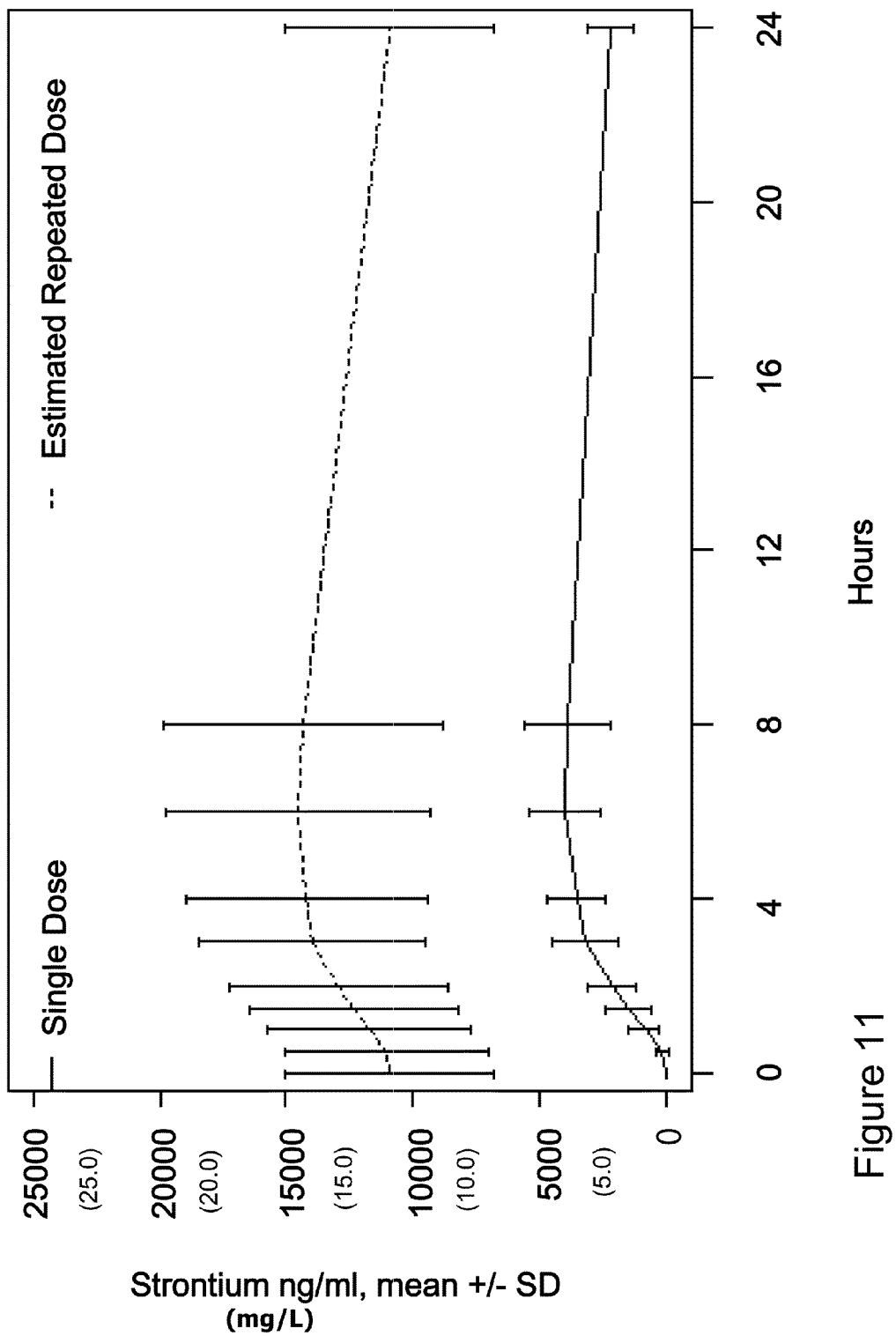
FIG. 11 is a plot of the strontium plasma concentration vs. time for single dose and estimated repeated dose PK profiles for strontium malonate (1.2 g dose) from the single dose pharmacokinetic experiment described in Example 11.

The observed 24 hours single dose concentrations are shown together with the estimated steady state steady concentrations after repeated oral dosing in FIG. 11.

The estimated mean steady state concentration ranges approximately from 11000 ng/ml to 14000 ng/ml during the time from dosing at time=00 to time=24 hours. The plot shown in FIG. 11 is based on arithmetic means and standard deviations.

The estimated mean $C_{max}$ steady state values are shown in Table 15 calculated for the four strontium treated groups of the single dose pharmacokinetic study described in Example 11. Means and confidence intervals are calculated on the log-scale and converted back to the original scale for presentation.

TABLE 15

| Treatment | Estimated Steady State Cmax (ng/ml) | | | Estimated Steady State Cmax (mg/L) | | |
|---|---|---|---|---|---|---|
| | Estimate | Lower CI | Upper CI | Estimate | Lower CI | Upper CI |
| strontium malonate 0.6 g | 9561 | 7535 | 12133 | 9.561 | 7.535 | 12.133 |
| strontium malonate 1.2 g | 14019 | 11048 | 17790 | 14.019 | 11.048 | 17.790 |
| strontium malonate 2.4 g | 23845 | 18791 | 30258 | 23.845 | 18.791 | 30.258 |
| Protelos 2.0 g | 12698 | 10006 | 16113 | 12.698 | 10.006 | 16.113 |

The dose response was evaluated and concluded linear with respect to $C_{max}$. This covered the concentration range (not baseline corrected) from 2.947 to 8.697 mg/L as assessed by the mean strontium $C_{max}$ values, and individual $C_{max}$ values from 1.027 to 16.510 mg/L. The estimated concentration values for the strontium malonate 1.2 g dose in Table 15 are within these ranges and it may be assumed that the dose linearity applies. Further, it may be concluded that the assumptions which the estimation of the steady state concentrations were based on are fulfilled up to the concentration level resulting from a strontium malonate 1.2 g dose. It is therefore finally concluded that daily oral dosing with 1.2 g strontium malonate formulated in tablets, such as the tablet formulation described in Example 9, and used in the pharmacokinetic study as described in Example 11 will lead to a maximum steady state concentration of mean 14.109 mg/L and CI from 11.048 to 17.790 mg/L.

Example 14

Dissolution and Disintegration Testing of 300 mg Strontium Malonate Tablets

We performed analysis of both dissolution and disintegration time of the 300 mg strontium malonate tablet manufactured as described in Example 9. This example provides a description of the analytical procedures used for these analysis as well as representative results from analysis of two batches of tablets.

The tablets manufactured as described in Example 9 were subjected to dissolution testing according the U.S. Pharmacopoeia (USP) method 28 in a paddle apparatus "2" as specified in the pharmacopoeia (see also the European pharmacopoeia, 5$^{th}$ edition Figure 2.9.3.1). 900 ml (±1%) 0.1 N HCl is added to the chamber. The paddle was operated at 50 RPM and the temperature adjusted to and maintained at 37±0.5° C. during the dissolution experiment. One tablet was placed in the dissolution chamber according to the Pharmacopoeia. After 30 minutes, a sample was taken of the dissolution medium from the middle of the dissolution chamber. Strontium content (as free $Sr^{2+}$ ions) in the sample of the dissolution medium was performed by means of Inductively-Coupled Plasma-Mass Spectrometry (ICP-MS) on a Perkin Elmer instrument Elan 6100. Samples were received in 10 mL tubes (Nunc), and the whole sample was transferred to a 2000 mL measuring bottle with distilled-water. Further dilution with 0.5% $HNO_3$ was performed. 10 mL of the sample was added to internal standards (Gallium, Ga, present in the two naturally occurring isotopes $^{69}$Ga and $^{71}$GA) prior to the ICP-MS analysis. The analysis of the sample on the ICP-MS apparatus was performed according the manufacturer's instructions.

Calibration was performed using a dilution of a certified reference standard from Merck (Sr 1000 mg/ml). A certified control material "TM-DWS" (a trace-element fortified reference sample derived from filtered sea-water sample from Lake Ontario provided by the Canadian National Water Research Institute) was used as control sample and is analyzed an appropriate number of times in the analytical sequence. Furthermore, a certified reference standard from Baker was used as a calibration control sample.

The ICP-MS instrument measured the intensity of $^{86}$Sr, $^{88}$Sr and Ga as net intensities (counts per second) in all solutions and the concentration in µg/L was calculated by linear regression from analysis of the calibration curve by use of internal standard method. Calibration range was 1-200 µg/L. Samples above the calibration range were reanalyzed after additional dilutions to fit the calibration range.

ICP-MS Measurement

The strontium concentration in the samples from each dissolution chamber was analyzed and the result expressed as the percent strontium in relation to the total strontium content in the tablet. Table 16 shows representative results from analysis of two batches of 300 mg strontium malonate tablets produced as described in Example 9.

TABLE 16

| Dissolution test | | Dissolution test | |
| --- | --- | --- | --- |
| Experimental run | Result | Experimental run | result |
| 1 | 99% | 1 | 87% |
| 2 | 83% | 2 | 98% |
| 3 | 87% | 3 | 94% |
| 4 | 98% | 4 | 92% |
| 5 | 90% | 5 | 71% |
| 6 | 92% | 6 | 82% |
| Average | 91.5% | Average | 87.3% |
| | (SD 6.2%) | | (SD 9.8%) |

Another important analysis of the tablets manufactured as described in Example 9 is determination of disintegration time. This analysis was performed essentially as described in the European Pharmacopoeia 5$^{th}$ ed. Section 2.9.1, test A. Briefly described the test was performed by placing 800 mL deionized water in the container whereafter the container was placed in a thermostatted water bath maintained at 37±2° C. One tablet was placed in each of the six chambers in the apparatus. The chambers were placed in the container so that there is at least 25 mm free space over the bottom of the container and at least 5 mm from the top of the chambers to the surface of the disintegration medium (deionized water). When the chambers with tablets were placed in the dissolution medium, a stop-watch is started and the tablets were monitored visually. The time until the last of the 6 tablets have disappeared was noted and this constituted the disintegration time. A tablet was considered to be disintegrated when there was no more visible traces of the tablet in the reaction chamber and/or when remnants in the chamber is devoid of any regular hard or shaped pieces. Table 17 below shows the results of disintegration testing of two batches of 300 mg strontium malonate tablets manufactured as described in Example 9.

TABLE 17

| 300 mg strontium malonate Tablet batch 1 | | 300 mg strontium malonate Tablet batch 2 | |
| --- | --- | --- | --- |
| Disintegration test | 8 min | Disintegration test | 6 min |

Results:

It is apparent the 300 mg strontium malonate tablets manufactured as described in Example 9 were able to disintegrate rapidly, with a disintegration time as determined according to current European pharmacopoeia methods of less than 10 min for two representative batches. The dissolution testing of the tablets from the same two batches was determined in 6 independent analytical runs for tablets from the same two batches. The average dissolution results showed a recovery of 91.5% and 87.3% after 30 min dissolution performed according to the U.S. Pharmacopoeia.

Combined these two results show that the 300 mg strontium malonate tablets have the ability to rapidly disintegrate and dissolve under analytical conditions designed to provide a relevant representation of the condition in the stomach after oral intake in humans. Accordingly it can be concluded that the pharmaceutical composition described in Example 9 is able to provide a rapid and reliable release of strontium malonate.

What is claimed:

1. A method for the treatment of a bone disease and/or condition resulting in a dysregulation of bone metabolism in a mammal in need thereof, the method comprising administering to the mammal a therapeutically effective amount of one or more strontium salts selected from the group consisting of strontium succinate, strontium glutamate, strontium ketoglutarate, strontium maleate, and strontium pyruvate, wherein the bone disease and/or condition resulting in a dysregulation of bone metabolism is osteoporosis or osteopenia.

2. The method of claim 1, wherein said mammal is a human.

3. The method of claim 1, wherein the one or more strontium salts are administered orally.

4. The method of claim 1, wherein the one or more strontium salts are administered in a pharmaceutical composition comprising the one or more strontium salts and one or more pharmaceutically acceptable excipients.

5. The method of claim 4, wherein the pharmaceutical composition comprises a tablet.

6. The method of claim 1, wherein the one or more strontium salts are administered at bedtime.

7. The method of claim 1, wherein the one or more strontium salts are administered once daily.

8. The method of claim 1, wherein the one or more strontium salts provide a dose from about 0.01 g to about 2 g of strontium.

9. The method of claim 1, wherein the one or more strontium salts provide a dose from about 0.1 g to about 2 g of strontium.

10. The method of claim 1, wherein the one or more strontium salts are anhydrous.

11. The method of claim 1, wherein the water solubility of the one or more strontium salts at room temperature is in a range of from about 1 g/l to about 100 g/l.

12. A method for the treatment of a bone disease and/or condition resulting in a dysregulation of bone metabolism in a subject in need thereof, the method comprising administering to said subject one or more strontium salts, wherein the one or more strontium salts provide a maximum plasma concentration of strontium from about 4 hours to about 24 hours after administration to said subject; wherein the one or more strontium salts are selected from the group consisting of strontium succinate, strontium glutamate, strontium ketoglutarate, strontium maleate, and strontium pyruvate; and wherein the bone disease and/or condition resulting in a dysregulation of bone metabolism is osteoporosis or osteopenia.

13. The method of claim 12, wherein said subject is a human.

14. The method of claim 12, wherein the one or more strontium salts are administered orally.

15. The method of claim 12, wherein the one or more strontium salts are administered in a pharmaceutical composition comprising the one or more strontium salts and one or more pharmaceutically acceptable excipients.

16. The method of claim 15, wherein the pharmaceutical composition comprises a tablet.

17. The method of claim 12, wherein the one or more strontium salts are administered at bedtime.

18. The method of claim 12, wherein the one or more strontium salts are administered once daily.

19. The method of claim 12, wherein the one or more strontium salts provide a dose from about 0.01 g to about 2 g of strontium.

20. The method of claim 12, wherein the one or more strontium salts provide a dose from about 0.1 to about 2 g of strontium.

21. The method of claim 12, wherein the one or more strontium salts provide a maximum plasma concentration of strontium from about 5 hours to about 10 hours after administration to said subject.

22. The method of claim 12, wherein the one or more strontium salts provide a maximum plasma concentration of strontium from about 4 hours to about 8 hours after administration to said subject.

23. The method of claim 12, wherein said maximum plasma concentration of strontium is at least 1.5 times higher than the plasma concentration of strontium at 2 hours after administration to said subject.

24. The method of claim 12, wherein said maximum plasma concentration of strontium is from about 0.5 mg/L to about 20 mg/L.

25. The method of claim 12, wherein said maximum plasma concentration of strontium is from about 1 mg/L to about 8 mg/L.

26. The method of claim 12, wherein the one or more strontium salts are anhydrous.

27. The method of claim 12, wherein the water solubility of the one or more strontium salts at room temperature is in a range of from about 1 g/1 to about 100 g/l.

28. A method for the treatment of a bone disease and/or condition resulting in a dysregulation of bone metabolism in a subject, the method comprising administering to said subject one or more strontium salts, wherein the one or more strontium salts provides a maximum plasma concentration of strontium from about 5.5 hours to about 24 hours after administration to said subject; wherein the one or more strontium salts are selected from the group consisting of strontium succinate, strontium glutamate, strontium ketoglutarate, strontium maleate, and strontium pyruvate; and wherein the bone disease and/or condition resulting in a dysregulation of bone metabolism is osteoporosis or osteopenia.

29. The method of claim 28, wherein said subject is a human.

30. The method of claim 28, wherein the one or more strontium salts are administered orally.

31. The method of claim 28, wherein the one or more strontium salts are administered in a pharmaceutical composition comprising the one or more strontium salts and one or more pharmaceutically acceptable excipients.

32. The method of claim 31, wherein the pharmaceutical composition comprises a tablet.

33. The method of claim 28, wherein the one or more strontium salts are administered at bedtime.

34. The method of claim 28, wherein the one or more strontium salts are administered once daily.

35. The method of claim 28, wherein the one or more strontium salts provide a dose from about 0.01 g to about 2 g of strontium.

36. The method of claim 28, wherein the one or more strontium salts provide a dose from about 0.1 to about 2 g of strontium.

37. The method of claim 28, wherein the one or more strontium salts provide a maximum plasma concentration of strontium from about 5.5 hours to about 10 hours after administration to said subject.

38. The method of claim 28, wherein said maximum plasma concentration of strontium is at least 1.5 times higher than the plasma concentration of strontium at 2 hours after administration to said subject.

39. The method of claim 28, wherein said maximum plasma concentration of strontium is from about 0.5 mg/L to about 20 mg/L.

40. The method of claim 28, wherein said maximum plasma concentration of strontium is from about 1 mg/L to about 8 mg/L.

41. The method of claim 28, wherein the one or more strontium salts are anhydrous.

42. The method of claim 28, wherein the water solubility of the one or more strontium salts at room temperature is in a range of from about 1 g/l to about 100 g/l.

43. A method for the treatment of a bone disease and/or condition resulting in a dysregulation of bone metabolism in a subject, the method comprising administering to said subject one or more strontium salts to provide a steady state plasma concentration of from about 5 mg/L to about 50 mg/L of strontium alter repeated administration through steady state conditions in said subject; wherein the one or more strontium salts are selected from the group consisting of strontium succinate, strontium glutamate, strontium ketoglutarate, strontium maleate, and strontium pyruvate; and wherein the bone disease and/or condition resulting in a dysregulation of bone metabolism is osteoporosis or osteopenia.

44. The method of claim 43, wherein said subject is a human.

45. The method of claim 43, wherein the one or more strontium salts are administered orally.

46. The method of claim 43, wherein the one or more strontium salts are administered in a pharmaceutical composition comprising the one or more strontium salts and one or more pharmaceutically acceptable excipients.

47. The method of claim 46, wherein the pharmaceutical composition comprises a tablet.

48. The method of claim 43, wherein the one or more strontium salts are administered at bedtime.

49. The method of claim 43, wherein the one or more strontium salts are administered once daily.

50. The method of claim 43, wherein the one or more strontium salts provide a dose from about 0.01 g to about 2 g of strontium.

51. The method of claim 43, where the one or more strontium salts provide a dose from about 0.1 to about 2 g of strontium.

52. The method of claim 43, wherein the steady state plasma concentration provided in said subject is from about 8 mg/L to about 20 mg/L of strontium.

53. The method of claim 43, wherein the one or more strontium salts are anhydrous.

54. The method of claim 43, wherein the water solubility of the one or more strontium salts at room temperature is in a range of from about 1 g/l to about 100 g/l.

55. The method of claim 1, wherein the one or more strontium salts comprise strontium succinate.

56. The method of claim 12, wherein the one or more strontium salts comprise strontium succinate.

57. The method of claim 28, wherein the one or more strontium salts comprise strontium succinate.

58. The method of claim 43, wherein the one or more strontium salts comprise strontium succinate.

* * * * *